(12) United States Patent
Rubinstein et al.

(10) Patent No.: US 6,447,778 B1
(45) Date of Patent: *Sep. 10, 2002

(54) PEPTIDE COMPOSITIONS FOR THE TREATMENT OF HIV INFECTION

(75) Inventors: Arye Rubinstein, Monsey-Wesley Hills, NY (US); Barry R. Bloom, Hastings on Hudson, NY (US); Yair Devash, Princeton Junction, NJ (US); Stanley J. Cryz, Berne (CH)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/599,286

(22) Filed: Jun. 22, 2000

Related U.S. Application Data

(63) Continuation of application No. 08/946,525, filed on Oct. 7, 1997, now Pat. No. 6,139,843, which is a continuation-in-part of application No. 08/785,696, filed on Jan. 17, 1997, now abandoned, which is a continuation of application No. 08/655,376, filed on May 30, 1996, now abandoned, which is a continuation of application No. 08/200,744, filed on Feb. 23, 1994, now abandoned, which is a continuation-in-part of application No. 07/837,781, filed on Feb. 14, 1992, now abandoned, which is a continuation-in-part of application No. 07/681,624, filed on Apr. 2, 1991, now abandoned.

(51) Int. Cl.[7] .............................................. A61K 38/04
(52) U.S. Cl. ................................ 424/188.1; 424/193.1; 424/194.1; 424/208.1
(58) Field of Search ........................... 424/208.1, 188.1, 424/184.1, 193.1, 194.1, 207.1, 196.11, 204.1; 530/324, 325, 327, 826

*Primary Examiner*—Jeffrey Stucker
(74) *Attorney, Agent, or Firm*—Amster, Rothstein & Ebenstein

(57) ABSTRACT

The present invention provides for peptide conjugate compositions, methods of using the peptide conjugate compositions, and pharmaceutical compositions comprising the peptide conjugate compositions. The peptide conjugate compositions comprise peptides with amino acid sequences similar to the gp120 principal neutralizing domain (PND) of HIV, gp41, and Nef (p27) of HIV and carriers which enhance immunogenicity. The peptide conjugate compositions of the present invention may comprise a multivalent cocktail of several different peptide conjugates. Also provided by present invention is a method for reducing the level of HIV titers in a mammal by administering to the mammal a peptide composition of the present invention in an amount effective to reduce the level of HIV titers. The peptide conjugate compositions of the present invention induce prolonged antibody response in serum, a high level of antibody in the mucosa, and the production of cytotoxic lymphocytes. The peptide conjugate compositions of the present invention also elicit neutralizing antibodies and decrease viral loads in a subject.

3 Claims, 26 Drawing Sheets

-○- Negative Control Serum
-●- Before Immunization
-△- 3 months
-▲- 6 months
-□- 12months -○- Negative Control Serum
-●- Before Immunization
-△- 3 months
-▲- 6 months
-□- 12months

- ○ Negative Control Serum
- ● Before Immunization
- △ 3 months
- ▲ 6 months
- □ 12 months

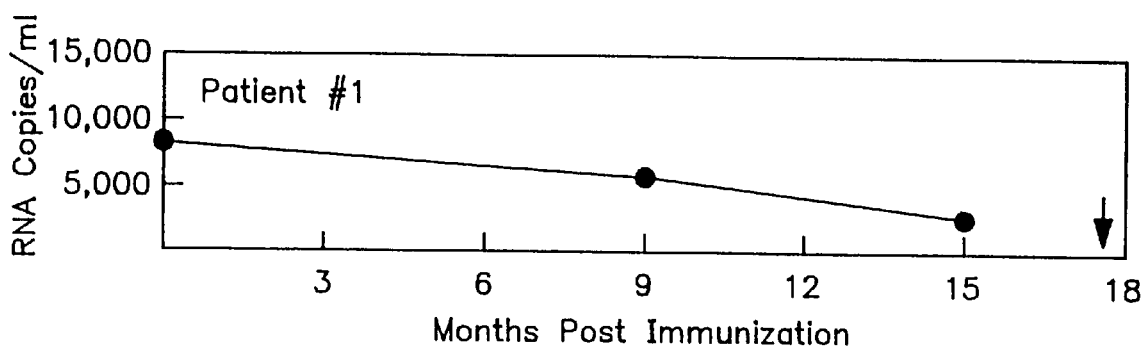
FIG. 15A
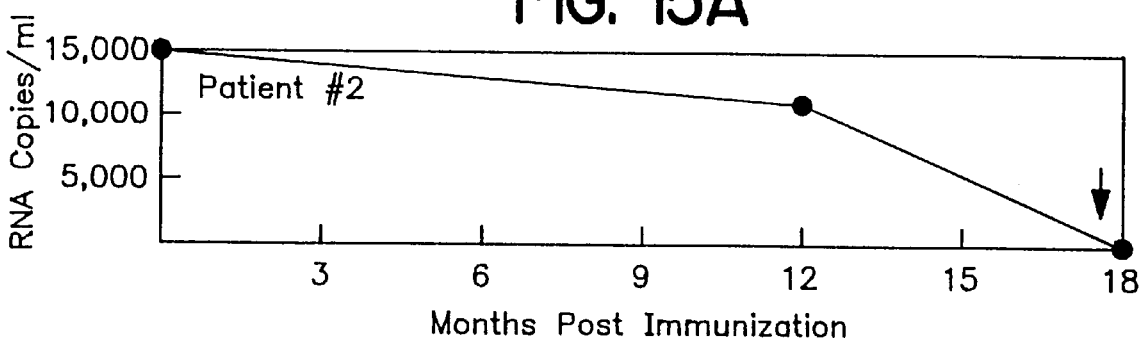
FIG. 15B
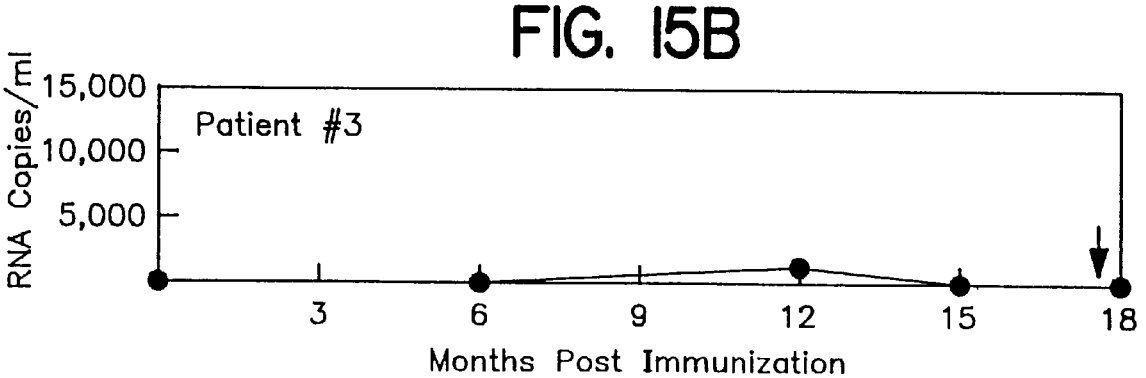
FIG. 15C
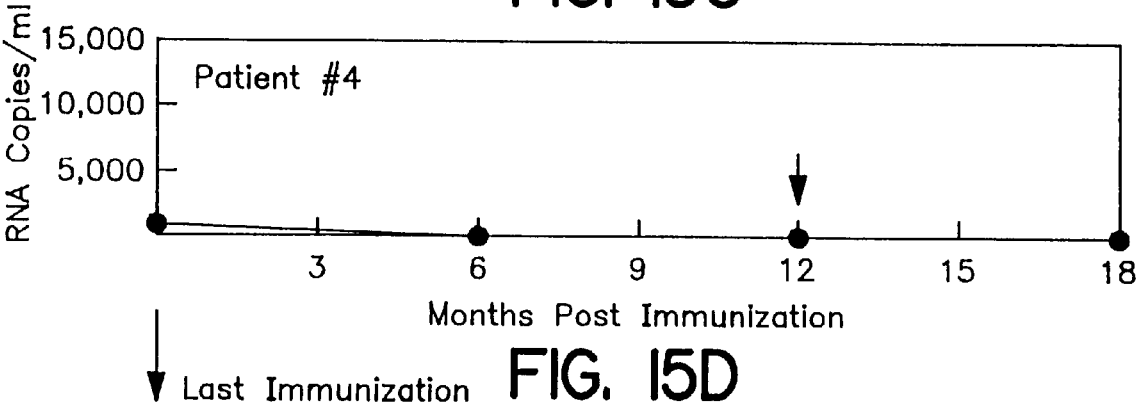
↓ Last Immunization  FIG. 15D

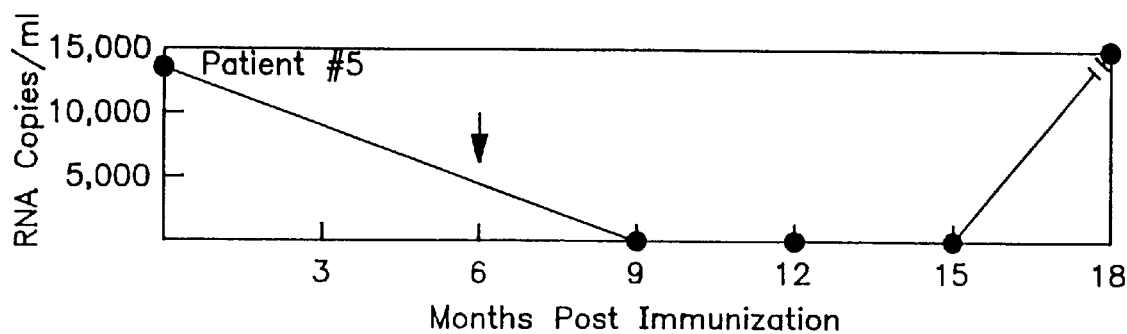
FIG. 15E
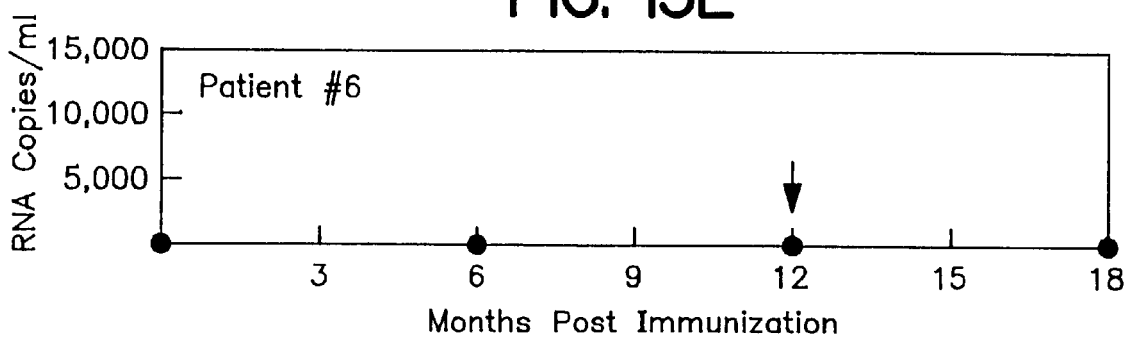
FIG. 15F
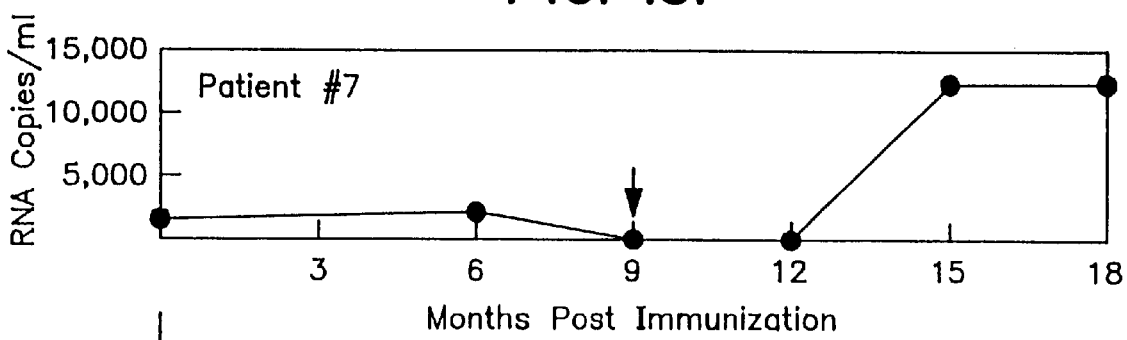
↓ Last Immunization  FIG. 15G

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 13
      (B) TYPE: amino acid
      (C) STRANDEDNESS: single
      (D) TOPOLOGY: linear (ii) MOLECULE TYPE: <Unknown>
      (A) DESCRIPTION: peptide (iii) HYPOTHETICAL: No (xi) SEQUENCE DESCRIPTION: SEQ ID NO: 1:

```
Lys Arg Ile His Ile Gly Pro Gly Arg Ala Phe Tyr Thr
1               5                   10
```

(2) INFORMATION FOR SEQ ID NO: 2:

(i) SEQUENCE CHARACTERISTICS:
        (A) LENGTH: 9
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 2:

```
Ile Thr Ile Gly Pro Gly Arg Ala Cys
1               5
```

(2) INFORMATION FOR SEQ ID NO: 3:

(i) SEQUENCE CHARACTERISTICS:
        (A) LENGTH: 9
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 3:

```
Ile Ala Ile Gly Pro Gly Arg Ala Cys
1               5
```

(2) INFORMATION FOR SEQ ID NO: 4:

(i) SEQUENCE CHARACTERISTICS:
        (A) LENGTH: 9
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 4:

```
Ile His Ile Gly Pro Gly Arg Ala Cys
1               5
```

(2) INFORMATION FOR SEQ ID NO: 5:

(i) SEQUENCE CHARACTERISTICS:
        (A) LENGTH: 19
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 5:

```
Gly Pro Gly Arg Ala Phe Gly Pro Gly Arg
1               5                   10
```

```
Ala Phe Gly Pro Gly Arg Ala Phe Cys
            15
```

(2) INFORMATION FOR SEQ ID NO: 6:

(i) SEQUENCE CHARACTERISTICS:
        (A) LENGTH: 13
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 6:

```
Arg Ser Ile His Ile Gly Pro Gly Arg Ala Phe Tyr Ala
1               5                   10
```

(2) INFORMATION FOR SEQ ID NO: 7:

(i) SEQUENCE CHARACTERISTICS:
        (A) LENGTH: 13
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 7:

```
Lys Ser Ile Thr Lys Gly Pro Gly Arg Val Ile Tyr Ala
1               5                   10
```

(2) INFORMATION FOR SEQ ID NO: 8:

(i) SEQUENCE CHARACTERISTICS:
        (A) LENGTH: 13
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 8:

```
Lys Gly Ile Ala Ile Gly Pro Gly Arg Thr Leu Tyr Ala
1               5                   10
```

(2) INFORMATION FOR SEQ ID NO: 9:

(i) SEQUENCE CHARACTERISTICS:
        (A) LENGTH: 13
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 9:

```
Ser Arg Val Thr Leu Gly Pro Gly Arg Val Trp Tyr Thr
1               5                   10
```

(2) INFORMATION FOR SEQ ID NO: 10:

(i) SEQUENCE CHARACTERISTICS:
        (A) LENGTH: 7
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 10:

Leu Leu Glu Asp Lys Trp Ala
1               5

(2) INFORMATION FOR SEQ ID NO: 11:

(i) SEQUENCE CHARACTERISTICS:
        (A) LENGTH: 6
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 11:

Arg Pro Met Thr Tyr Lys
1               5

(2) INFORMATION FOR SEQ ID NO: 12:

(i) SEQUENCE CHARACTERISTICS:
        (A) LENGTH: 6
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 12:

Gly Gly Lys Trp Ser Lys
1               5

(2) INFORMATION FOR SEQ ID NO: 13:

(i) SEQUENCE CHARACTERISTICS:
        (A) LENGTH: 7
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 13:

Pro Gly Pro Gly Ile Arg Tyr
1               5

(2) INFORMATION FOR SEQ ID NO: 14:

-continued

```
    (i) SEQUENCE CHARACTERISTICS:
        (A) LENGTH: 8
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 14:

Gly Pro Gly Ile Gly Pro Gly Val
1               5

(2) INFORMATION FOR SEQ ID NO: 15:

(i) SEQUENCE CHARACTERISTICS:
        (A) LENGTH: 10
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 15:

Ile His Ile Gly Pro Gly Arg Ala Phe Tyr
1               5                   10

(2) INFORMATION FOR SEQ ID NO: 16:

(i) SEQUENCE CHARACTERISTICS:
        (A) LENGTH: 6
        (B) TYPE: amino acid
        (C) STRANDEDNESS: single
        (D) TOPOLOGY: linear (ii) MOLECULE TYPE: <Unknown>
        (A) DESCRIPTION: peptide (iii) HYPOTHETICAL: No (xi) SEQUENCE DESCRIPTION: SEQ ID NO: 16:

Gly Pro Gly Arg Ala Phe
1               5
```

PEPTIDE COMPOSITIONS FOR THE TREATMENT OF HIV INFECTION

CROSS REFERENCE TO RELATED APPLICATIONS

This application is a continuation of U.S. patent application Ser. No. 08/946,525, filed Oct. 7, 1997, now U.S. Pat. No. 6,139,843, which is continuation-in-part of U.S. patent application Ser. No. 08/785,696 filed on Jan. 17, 1997, now abandoned, which is a continuation of U.S. patent application Ser. No. 08/655,376, filed May 30, 1996, now abandoned, which is a continuation of U.S. patent application Ser. No. 08/200,744, filed Feb. 23, 1994, now abandoned, which is a continuation-in-part of U.S. patent application Ser. No. 07/837,781 filed Feb. 14, 1992, now abandoned, which is a continuation-in-part of U.S. patent application Ser. No. 07/681,624 filed Apr. 2, 1991, now abandoned, the contents of each of which are hereby incorporated by reference in their entirety.

STATEMENT OF GOVERNMENT INTEREST

This invention was made with government support under NIH Grant No. P30 AI27741. As such, the government has certain rights in this invention.

BACKGROUND OF THE INVENTION

There have been recent advances in the use of retrovirus-derived vaccines for the treatment of HIV. Specifically, a formalin-inactivated whole HIV vaccine has been developed which has conferred protection in Macaques. Immunization with vaccines potentiated with albumin has resulted in the protection from clinical disease in eight out of nine monkeys challenged with infectious, doses of HIV. Notably, protection could be achieved even in cases where entry of viruses is not prevented, suggesting that it may not be necessary to completely block infection in order to have a successful vaccine.

Whole killed HIV vaccines have also been beneficial in the treatment of chimpanzees who were previously infected by HIV. These chimpanzees appear to have cleared the HIV infection in their blood streams following the vaccinations. Post-exposure immunization in humans has also been studied. These tests suggest that immunization may be used to protect humans from HIV infections, and also to treat humans who have already been infected with the virus. However, whole virus vaccines may contain infectious particles. As a result, it may be safer to use essential components of the virus to confer protection. Epitopes of the virus are one example of a safer, essential component of the virus. More recent studies have confirmed that partial protection from infection can be achieved also by gp120 and gp160 derived vaccines. (Desrosiers, R. C. et al. *Proc. Nat'l Acad. Sci. USA*, 86:6353 (1989), Kestler, et al. *Science,* 248:1109 (1990); Murphey-Corb, M. *Science,* 246:1293 (1989)).

It has long been recognized that peptide epitopes of amino acids conjugated to immunogenic carriers can elicit high levels of high affinity antipeptide antibodies. (See Talwar, G. P., Bloom, B. et al., "Biological and Clinical Aspects of Reproduction", *Exceptor Med. Series* 394:2224–2232 (1987), in which the beta chain of human chorionic gonadotropin was conjugated to tetanus toxoid to produce an antifertility vaccine.)

The carriers to which peptides are conjugated in this invention have all been used as immunogenic carriers in animals, and some have been used in humans. By way of example, the purified protein derivative (PPD) of tuberculin from *Mycobacterium tuberculosis,* which is the preferred carrier of the invention, is a unique immunologic reagent, because virtually everyone in the world with a functional immune response who has been exposed to BCG or *M. tuberculosis* infections will have a T-cell mediated, delayed-type hypersensitivity response to minute amounts of PPD. Tuberculin-PPD conjugates have been utilized in the past. Mice pre-sensitized or "primed" with BCG can produce high levels of antibodies to peptide or carbohydrate epitopes conjugated to PPD. Of particular interest are studies on the NANP repeating epitope of the *P. falciparum* circumsporozoite antigen, which is immunogenic in only two strains of mice. Conjugating the NANP repeating peptide to PPD elicits the production of antibody titers greater than 1:1000 in genetically non-responder strains to the NANP epitope. This degree of response is comparable to that seen in responder strains given the peptide conjugate in complete Freund's adjuvant. (See Lussow et al., "Use of Tuberculin Purified Protein Derivative-Asn-Ala-Asn-Pro Conjugate in Bacillus Calmette-Guerin Primed Mice Overcomes H-2 Restriction of the Antibody Response and Avoids the Need for Adjuvants," *Proc. Nat'l Acad. Sci. USA* 87 (1990)).

*Pseudomonas aeruginosa* exotoxin A (toxin A) has been used effectively as a carrier in conjugate vaccines. Conjugates made with this carrier have higher immunogenicity, especially when coupled with the recombinant protein R32 to create an immune response against the sporozoite stage of *Plasmodium falciparum. Pseudomonas aeruginosa* exotoxin A may be purified from the supernatant of fermentor-grown cultures of *Pseudomonas aeruginosa* PA 103. Toxin A has been classified as a superantigen based upon results in animals. Toxin A can be completely and irreversibly detoxified by covalent coupling to adipic acid dihydrazide (ADH), a 4 carbon spacer molecule. This step destroys the ADPR-transferase activity of the toxin molecule, hence rendering it nontoxic. The non-reacted hydrazide group can be used to covalendy couple haptens to toxin A.

To date, the following haptens have been coupled to toxin A by the inventors by the use of ADH and carbodiimide as a coupling agent: (1) small molecular weight polysaccharides from *P. aeruginosa* and *Escherichia coli;* (2) the immunodominant (NANP)$^3$ repeat from *Plasmodium falciparum* circumsporozoite; and (3) a recombinant protein, termed R32LR, which contains multiple NANP and NVDP repeats from *P. falciparum.*

Approximately 5,000 subjects have been immunized by the inventors with toxin A-containing vaccines produced by the inventors. As much as 400 mg of toxin A have been administered per dose, with multiple (3) doses given to subjects. These vaccines have been very well tolerated. Mild to moderate, transient local reaction occur in 0.25% of vaccines. Systemic reactions occur in 0.1–2%. Abnormal blood chemistries have not been associated with these vaccines.

Keyhole Limpet Hemocyanin (KLH) is a high molecular weight protein which is purified from megathura crenulata. KLH has many available primary amines from lysine residues which facilitate protein conjugation. KLH is highly immunogenic, and because of its availability of primary amines, is ideal for protein conjugation.

Tetanus and diphtheria toxoids have also been used successfully as protein carriers. Diphtheria toxoid has been used with a synthetic 31 amino acid N-terminal peptide. Both tetanus toxoid and diphtheria toxoid have proved to be effective carriers in humans for the poorly immunogenic carbohydrate antigen of *Hemophilus influenza b.*

The recombinant core antigen of hepatitis B has the capability of self-assembling into 27 millimeter particles which are highly immunogenic in experimental animals. These HBV core particles may be conjugated directly with peptides, using recombinant DNA technology. Fusion proteins can be produced between the HBV core antigen and defined sequence peptides with high epitope density, which lead to high titer antibodies, as well as to long lasting neutralizing antiviral immunity. Hepatitis B core antigens and self-assembled HBc-HIV peptide fusion protein may be used as protein carriers.

It has been established that the major antigenic component of the mycobacterial cell wall is a protein which consists of a polypeptide monomer of between 10 and 16 Kd, the amino terminal sequence of which reveals that it is related to the GroES heat-shock protein present in many bacteria. It has been indicated that the major antigenic component of mycobacteria recognized by CD4+ T-cells is associated with the cell wall. BCG cell wall (purified) may be used as a protein carrier. BCG may also be used to prime animals or humans prior to vaccination. BCG priming enhances the humoral and cellular responses induced by vaccination.

Currently, the only adjuvant licensed for use in man is alumina. In the present invention, alumina may be used with the conjugates which include the carriers *Pseudomonas aeruginosa* exotoxin A, KLH, and tetanus and diphtheria toxoids. Aluminum-based gels such as $Al(OH)_3$ and $AlPO_4$, as well as liposomes may be used as adjuvants with the carrier *Pseudomonas aeruginosa* exotoxin A in the present invention. PPD conjugates can be given in saline with no further adjuvants to tuberculin-positive subjects. For the BCG cell wall and HBc antigen conjugates, it is likely that adjuvants would be required. Ribi adjuvant containing trehalose dimycolate and 2% squalene may be used as an adjuvant. Alternatively, if studies on the long-term safety of incomplete Freund's adjuvant or ISCOM's adjuvant indicate their safety and efficacy in humans, these adjuvants may be used. Microencapsulation technology using polyactide/polyglycolide biodegradable polymers may also be used as an adjuvant.

Because a significant amount of HIV-1 transmission occurs from cell to cell (see McCune, "HIV-1: The Infective Process in vivo", *Cell,* Vol. 64, pp. 351–363 (1991)), neutralizing antibodies alone cannot prevent clinical infection. Furthermore, since the majority of HIV-1 transmission occurs via the mucosal route, effective mucosal immunity is necessary for protection from HIV-1 infection. The effectiveness of an HIV-1 vaccine depends upon its capacity to induce HIV-1 specific cell mediated immunity and humoral immunity in both serum and in the mucosa.

To date, no preventive vaccine has been reported which induces humoral, cellular and mucosal immune response. Hence, it is desirable to develop a vaccine which induces antibody (serum and mucosal) as well as PND-specific T cell (CTL) response after immunization therewith.

Current results with post-infection HIV-1 recombinant gp120 and gp160 (Salk J, et al. *Science* 1993; 260: 1270–72; Redfield R R, et al. *N Engl J Med* 1991; 324: 1667–84; Valentine F T, et al. *J Infect Dis* 1996; 173: 1336–46; Eron J J, et al. Lancet. 1996; 348: 1547–51; Haynes B F Lancet. 1996; 348:933–37; Haynes B F *Lancet* 1996; 348: 1531–2) vaccines are discouraging. (Redfield R R, et al. *N Engl J Med* 1991; 324: 1667–84; Valentine F T, et al. *J Infect Dis* 1996; 173: 1336–46; Eron J J, et al. *Lancet* 1996; 348: 1547–51). In light of the enormous turnover of HIV-1 virions and CD4 cells (Saag M S, et al. *Nat Med* 1996; 625–29; Mellors J W, et al. *Ann Intern Med* 1995; 122: 573–79; Ho Dd, et al. *Nature* 1995; 373: 123–126; Fauci A S *Nature* 1996; 384: 529–33) it was suggested that the prospect of ever inducing a more effective anti-HIV-1 immunity was slim in an immune system that is already working overtime. (Haynes B F *Lancet* 1996; 348:933–37; Haynes B F *Lancet* 1996; 348: 1531–2; Haynes B F, et al. *Science* 1996; 271: 324–8).

In contrast to this bleak outlook are observations of immune responses in long term non-progressors that are absent or decreased in rapid progressors (Haynes B F *Lancet* 1996; 348:933–37; Haynes B F *Lancet* 1996; 348: 1531–2; Haynes B F, *Science* 1996; 271: 324–8) and recent studies in infants have indicated the existence of abortive infections. (Bryson Y J, *N Engl J Med* 1995; 332: 833–8; Roques P A, *AIDS* 1995; 9: F19–26.) The development of our vaccine was based on studies showing a correlation between high affinity antibodies to gp120 or to the $V_3$ loop and reduced maternofetal HIV-1 transmission. (Goedert J J, *Lancet* 1989; ii: 1351–53; Rubinstein A, et al. *AIDS* 1995; 9: 243–51). The $V_3$ loop is known to participate in vital viral properties such as cell tropism and cell fusion. Antibodies to the $V_3$ loop decline with disease progression, while antibodies to whole gp160 remain stable. (Fenouillet E, *Clin Exp Immunol* 1995; 99: 419–24). Guinea pig immune sera against a BCG vector secreting the $V_3$-Primary Neutralizing. Domain (PND) blocked HIV-1 infection in SCID/hu mice (Honda M, et al. *Proc Natl Acad Sci USA* 1995; 92: 10693–97) and a monoclonal antibody to the $V_3$ loop protected chimps against HIV-1 infection. (Emini E A, et al. *Nature* (London) 1992; 355: 728–3018).

Thus, there remains a need for the discovery and development of peptide carrier conjugate vaccines capable of inducing prolonged antibody immune response. There is an additional need for vaccines which are capable of inducing a serum humoral immune response, mucosal humoral immune response and the production of cytotoxic lymphocytes. In addition, there is a great need for the discovery and development of an effective method of treatment and prevention of HIV infection which will reduce the viral load in a subject, thereby preventing or limiting the progression of the disease.

BRIEF DESCRIPTION OF THE DRAWINGS

FIGS. 3B and 3C also represents the results of competition between peptides 282 (FIG. 3B) and MN with peptide 284 (IAIGPGRAC) (SEQ ID NO:3) (FIG. 3C) in mouse 284—4. Both peptides 282 and MN competed effectively.

FIG. 9A shows the results using the KRIHIGPGRAFYT (SEQ ID NO:1) peptide; FIG. 9B the GPGRAFGPGRAFGPGRAFC peptide (SEQ ID NO:5); FIG. 9C the IYIGPGRAC (SEQ ID NO:3) peptide; FIG. 9D the IHIGPGRAC (SEQ ID NO:4) peptide; and FIG. 9E the IAIGPGRAC (SEQ ID NO:3) peptide.

FIG. 10A represents the results using the KRIHIGPGRAFYT (SEQ ID NO:1) plate; FIG. 10B the GPGRAFGPGRAFGPGRAFC (SEQ ID NO:5) plate; FIG. 10C the IYIGPGRAC (SEQ ID NO:2) plate; FIG. 10D the IHIGPGRAC (SEQ ID NO:4) plate; and FIG. 10E the IAIGPGRAC (SEQ ID NO:3) plate.

FIG. 12A represents the results of immunization of patient #1; FIG. 12B of patient #2; FIG. 12C of patient #3, FIG. 12D of patient #4; FIG. 12E of patient #5; FIG. 12F of patient #6; and FIG. 12G of patient #7.

FIG. 14A represents the results of immunization of patient #1; FIG. 14B of patient #2; FIG. 14C of patient #3, FIG. 14D of patient #4; FIG. 14E of patient #5; FIG. 14F of patient #6; and FIG. 14G of patient #7.

FIGS. 15A–15G set forth the effect of PPD-pentapeptide-PND immunization on viral load (NASBA assay) RNA copies/ml. FIG. 15A represents the results of immunization of patient #1; FIG. 15B of patient #2; FIG. 15C of patient #3, FIG. 15D of patient #4; FIG. 15E of patient #5; FIG. 15F of patient #6; and FIG. 15G of patient #7.

SUMMARY OF THE INVENTION

Figure 1:
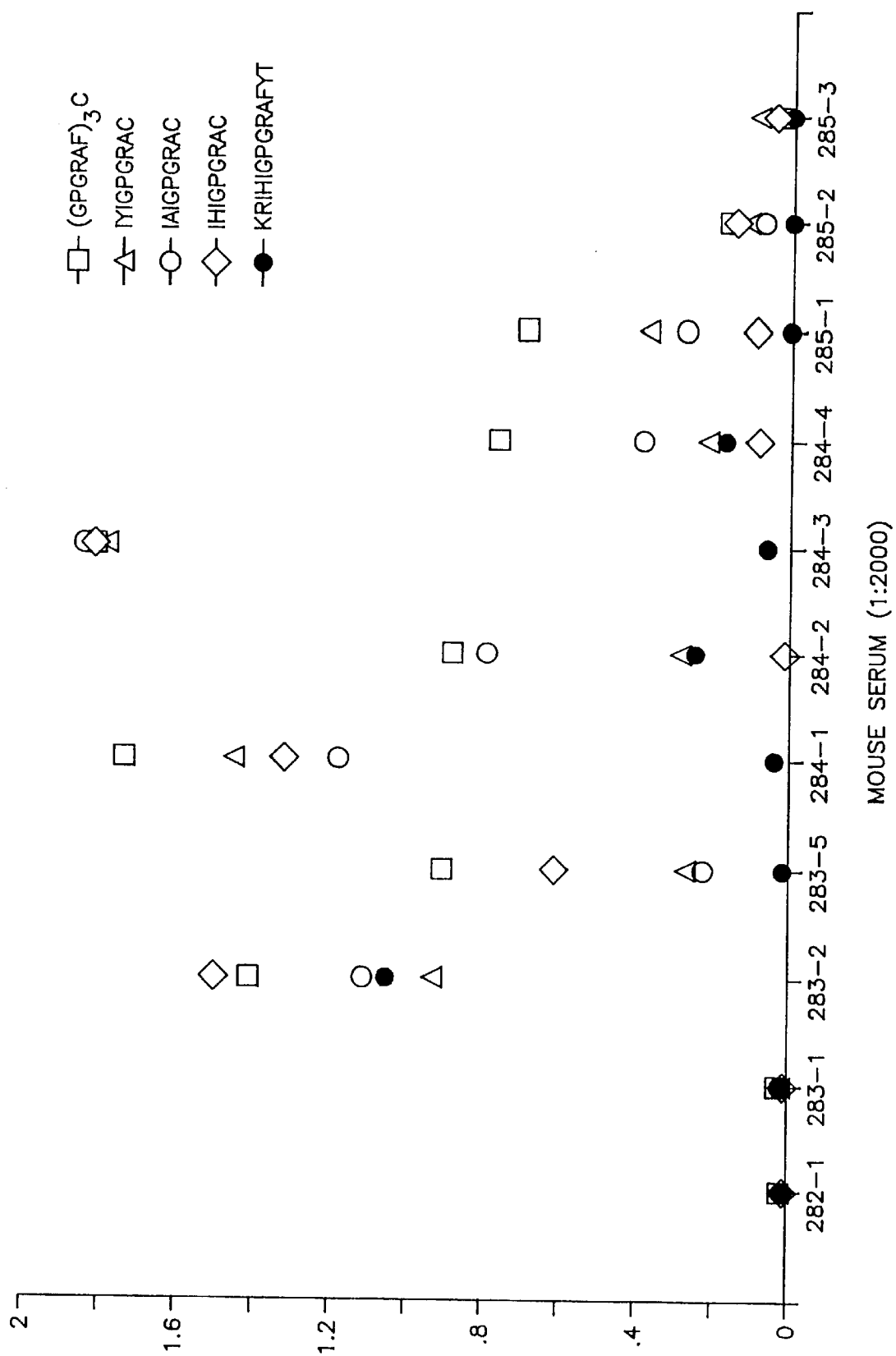
FIG. 1 represents the immunoreactivity of mice vaccinated with conjugates of KLH and five different peptides: 282 (GPGRAFGPGRAFGPGRAFC) (SEQ ID NO:5), 283 (IYIGPGRAC) (SEQ ID NO:2), 284 (IAIGPGRAC) (SEQ ID NO:3), 285 (IHIGPGRAC) (SEQ ID NO:4) and MN (KRIHIGPGRAFYT) (SEQ ID NO:1).
Figure 2:
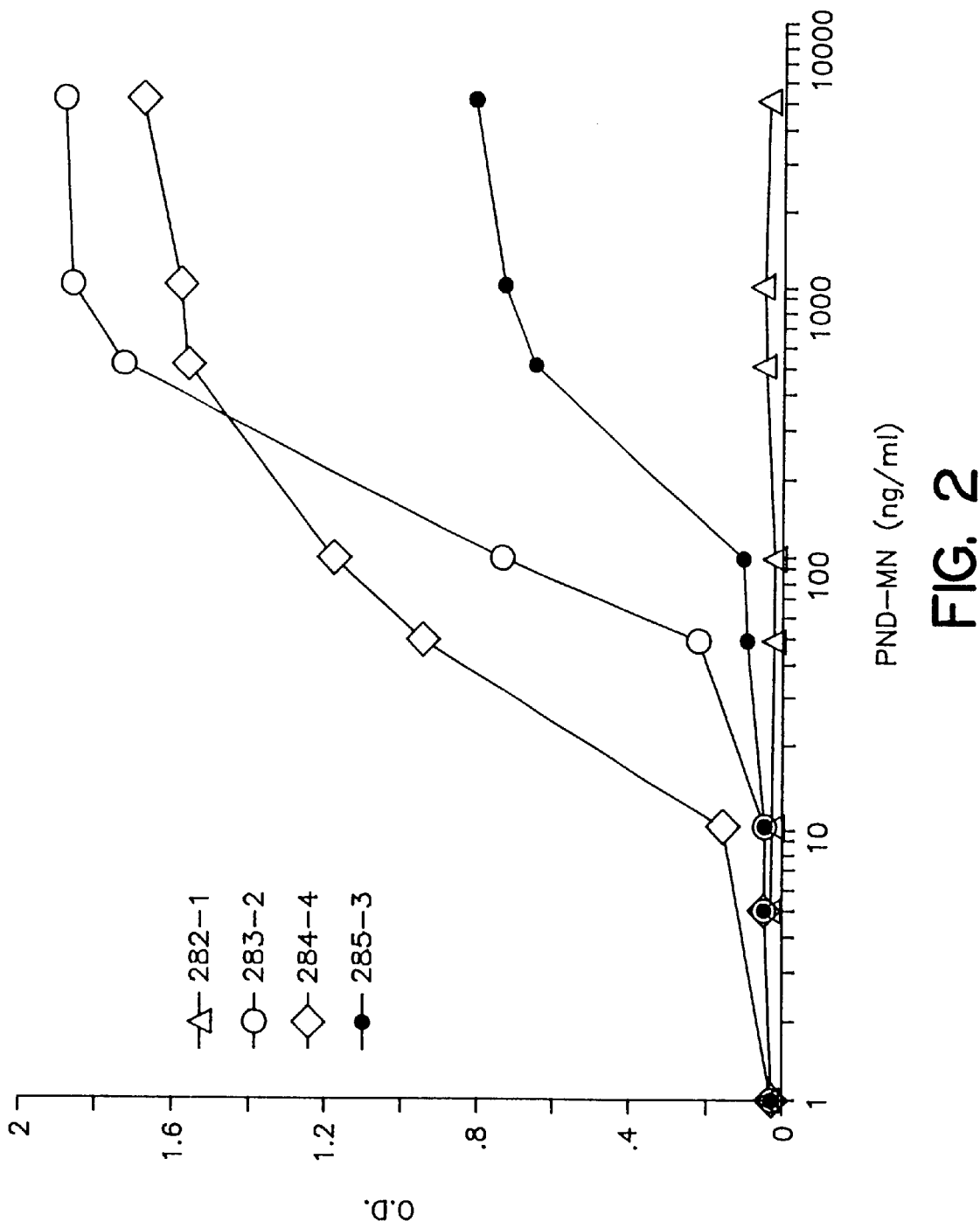
FIG. 2 represents the affinity/avidity of mice with the highest titers of antibody to conjugates of KLH and peptides 282 (GPGRAFGPGRAFGPGRAFC) (SEQ ID NO:5), 283 (IYIGPGRAC) (SEQ ID NO:2), 284 (IAIGPGRAC) (SEQ ID NO:3) and 285 (IHIGPGRAC) (SEQ ID NO:4).
Figure 3A:
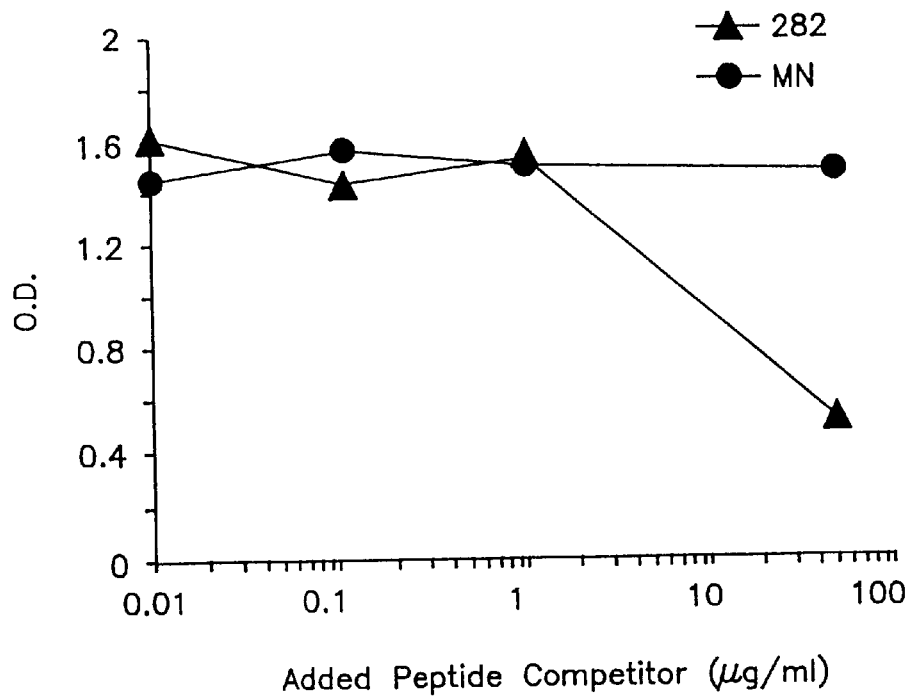
FIGS. 3A–3C represent the results of competition between peptides 282 (GPGRAFGPGRAFGPGRAFC) (SEQ ID NO:5) and MN (KRIHIGPGRAFYT) (SEQ ID NO:1) with peptide 283 (IYIGPGRAC) (SEQ ID NO:2) in mouse 283–5 (FIG. 3A). Peptide 282 competed effectively, and peptide MN did not.
Figure 3B:
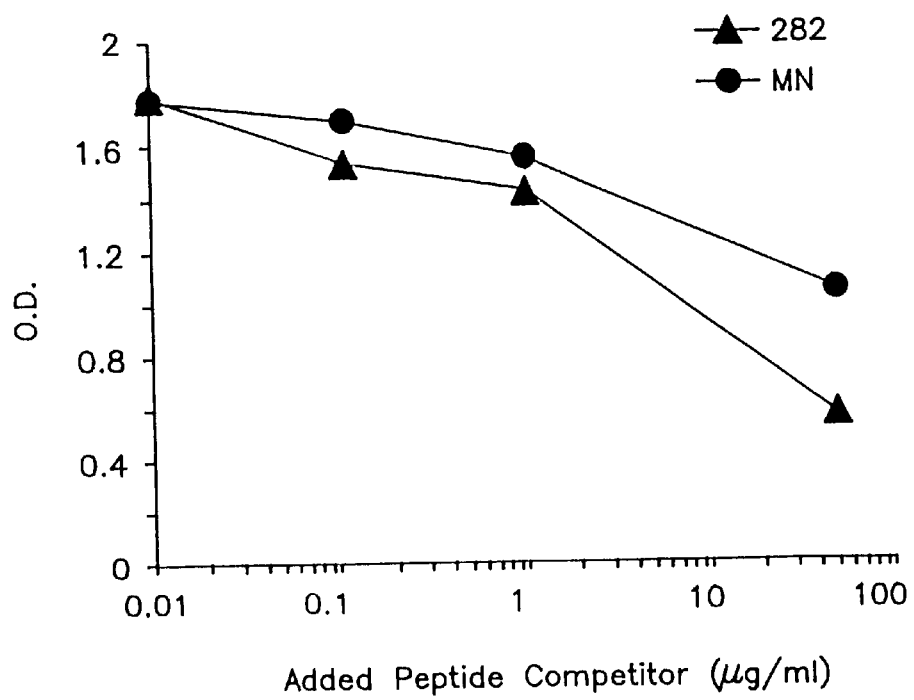
Figure 3C:
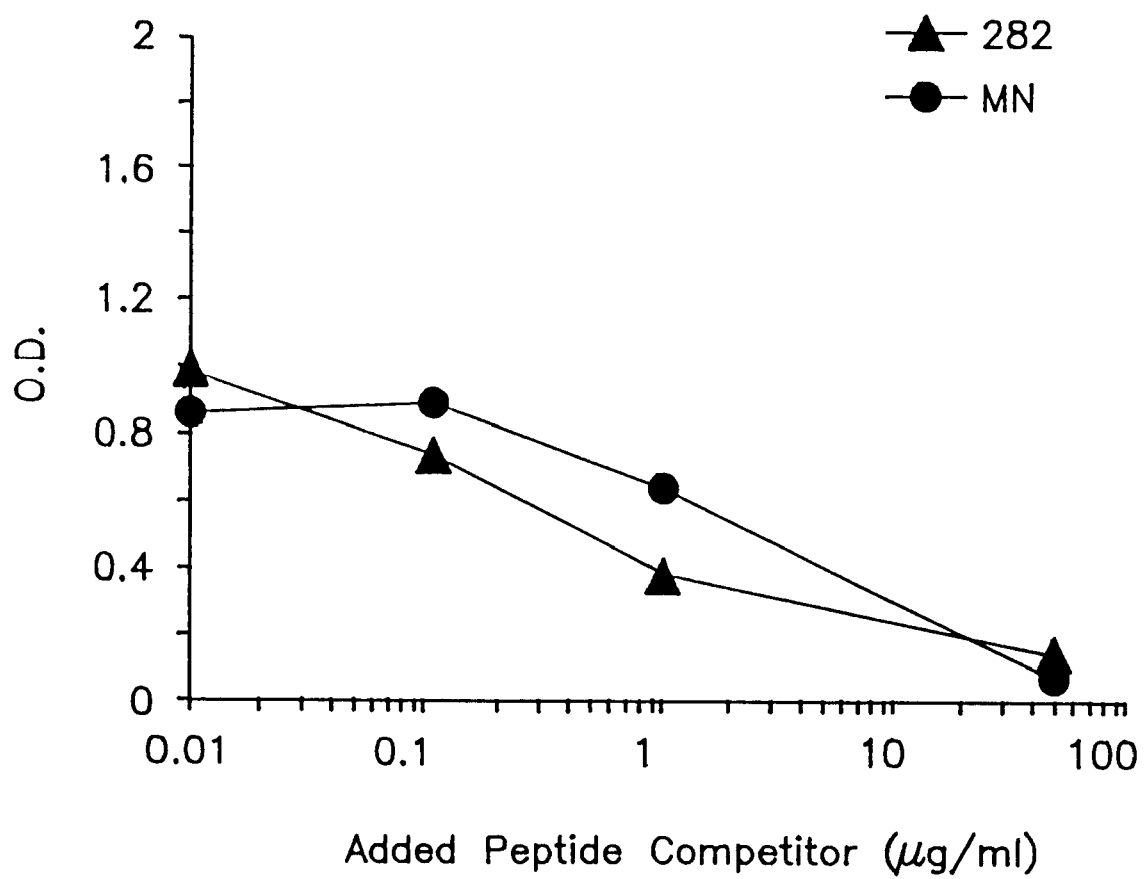

The present invention provides for peptide conjugate compositions which comprise peptides with amino acid sequences similar to the gp120 principal neutralizing domain (PND) of HIV, gp41, and Nef (p27) of HIV and carriers which enhance immunogenicity, such conjugates to be used in compositions for the treatment and prevention of HIV infection. The peptide conjugate compositions of the present invention may comprise either a single peptide conjugate alone or a cocktail of several different peptide conjugates.

The present invention further provides a method for reducing the level of HIV titers in a mammal by administering to the mammal a peptide composition of the present invention in an amount effective to reduce the level of HIV titers. The peptide conjugate compositions of the present invention induce prolonged antibody response in serum, a high level of antibody in the mucosa, and the production of cytotoxic lymphocytes. The peptide conjugate compositions of the present invention also elicit neutralizing antibodies and decrease viral loads in a subject.

DETAILED DESCRIPTION OF THE INVENTION

The present invention provides for peptide conjugate compositions to be used in the treatment and transmission prevention of HIV. The peptide conjugate compositions of the present invention are made by conjugating peptides with amino acid sequences similar to specific regions of HIV and carriers so as to form peptide conjugates.

The peptide conjugate compositions of the present invention not only induce the production of high affinity/avidity antibodies in the serum, but induce the production of such antibodies for extensive periods of time, and also induce the production of antibodies in the mucose. The peptide conjugate compositions of the present invention also induce cell mediated immune response by inducing the production and proliferation of cytotoxic lymphocytes. Further, the peptide conjugate compositions of the present invention induce in subjects an increase or emergence of neutralizing antibodies to primary HIV isolates and autologous HIV isolates, and reduce HIV viral load in these subjects.

The present invention provides a method for reducing the level of HIV titers in a mammal by administering to the mammal a peptide composition in an amount effective to reduce the level of HIV titers. The peptide composition is administered to the subject prior to, or subsequent to, HIV infection. The peptide composition comprises at least one peptide coupled to an immunogenic carrier, wherein said peptide is selected from the group consisting of KRIHIGPGRAFYT (SEQ ID NO:1), RSIHIGPGRAFYA (SEQ ID NO:6), KSITKGPGRVIYA (SEQ ID NO:7), KGIAIGPGRTLYA (SEQ ID NO:8), SRVTLGPGRVWYT (SEQ ID NO:9), and HIV strain variants thereof. The peptide composition may comprise at least two of the above peptides coupled to an immunogenic carrier. In a preferred embodiment of the invention, the peptide composition comprises at least five of the above peptides coupled to an immunogenic carrier. The peptide composition may further comprise at least one peptide selected from the group consisting of LLELDKWA (SEQ ID NO:10), RPMTYK (SEQ ID NO:11), GGKWSK (SEQ ID NO:12), PGPGIRY (SEQ ID NO:13), GPGIGPGV (SEQ ID NO: 14), and HIV strain variants thereof.

Also provide by the present invention are pharmaceutical composition comprising a peptide composition comprising at least one of the following peptides coupled to an immunogenic carrier: KRIHIGPGRAFYT (SEQ ID NO:1), RSIHIGPGRAFYA (SEQ ID NO:6), KSITKGPGRVIYA (SEQ ID NO:7), KGIAIGPGRTLYA (SEQ ID NO:8), SRVTLGPGRVWYT (SEQ ID NO:9), LLELDKWA (SEQ ID NO:10), RPMTYK (SEQ ID NO:11), GGKWSK (SEQ ID NO:12), PGPGIRY (SEQ ID NO:13), GPGIGPGV (SEQ ID NO: 14), and HIV strain variants thereof. The pharmaceutical composition may fturther comprise at least one peptide selected from the group consisting of LLELDKWA (SEQ ID NO:10), RPMTYK (SEQ ID NO:11), GGKWSK (SEQ ID NO:12), PGPGIRY (SEQ ID NO:13), GPGIGPGV (SEQ ID NO: 14), and HIV strain variants thereof. The peptide composition preferably is present in the pharmaceutical composition in an amount effective to reduce HIV titers in a mammal that the pharmaceutical composition is administered to.

HIV strain variants of the peptides of the present invention are herein defined as peptides corresponding to the peptides of the present invention which are obtained from other strains of HIV. These peptides may vary from the peptides of the present invention by 1–3 amino acids at either or both the carboxy and amino terminal ends of the peptide.

Carriers which may be used for conjugation with the peptides of this invention include purified protein derivative (PPD) of tuberculin from M. tuberculosis, Pseudomonas aeruginosa exotoxin A (toxin A), keyhole limpet hemocyanin (KLH), filamentous hemagglutinin (FHA) of bordetella pertussis, tetanus toxoid, diphtheria toxoid, hepatitis B core antigen, T helper cell (Th) epitopes of tetanus toxoid (TT) and Bacillus Calmette-Guerin (BCG) cell wall. The preferred carriers of this invention are PPD and toxin A. In addition, an adjuvant, such as aluimina, Ribi, Freund's, Iscom's or microencapsulation technology adjuvant may be used with these carriers.

Other carriers which may be used for conjugation with peptides of this invention are the recombinant 10 kDa, 19 kDa and 30–32 kDa proteins from M. leprae and from M. tuberculosis, or any combination of these proteins. The 10 kDa, 19 kDa and 30–32 kDa proteins are antigens recognized by most M. tuberculosis and M. leprae-reactive human T cell lines and cell wall reactive cell clones. The 10 kDa protein is 44% homologous to the heat-shock protein (HSP-Groes) of E. coli. The 19 kDa protein has a lipidation signal in it, and was shown to stimulate IL-2 production (Dr. Barry Bloom, unpublished data).

The carriers may be coupled to the peptides of the present invention using techniques know to one skilled in the art. In a preferred embodiment of the invention, PPD is coupled to a peptide of the present invention using glutaraldehyde. Using this method allows for random conformational and linear presentations of the peptides and can therefore be recognized by a broader range of MHC-I and MHC-II molecules. The coupling method also allows for intracellular processing of the peptide in the cytosol to promote MHC-I responses. In a preferred embodiment of the invention, each peptide in a multiple, multivalent peptide mixture is coupled separately to PPD and a mixture of all the coupled peptides is then prepared. This method of conjugation also increases the ratio of peptide to PPD and reduces the delayed type hypersensitivity skin response (DTHR) to PPD, allowing for the use of much higher PPD doses intradermally without local adverse effects. In a preferred embodiment of the invention, 2–5TU are used for skin testing with PPD, and 12–25TU is used for the vaccination and is injected into one site.

Proliferative responses of PBNC to the 10 kDa antigen from M. tuberculosis are similar to those induced by whole M. tuberculosis, and greater than those elicited by other proteins from M. tuberculosis culture filtrates. 10 kDa antigens are identical to those defined for BCG-a. The 10 kDa antigen elicits IFN production by PBMC of healthy tuberculin reactors and by plural fluid mononuclear cells. In addition, T cell clones reactive to the 10 kDa protein from M. leprae also recognize epitopes that are cross-reactive with the antigen of M. tuberculosis. Further, the 10 kDa protein elicits strong delayed-type hypersensitivity reactions (DTHR) in guinea pigs sensitized to M. leprae and to BCG.

Purified 32 kDa protein from filtrates of M. tuberculosis and BCG is also believed important for protective immunity. T cell derived lymphokines, such as interferon, play an essential role in the control of disease. It has been shown that all tuberculoid leprosy patients with benign disease course and controls have a marked parallelism of responsiveness towards whole M. leprae and purified antigen 85, which is the major secreted 30–32 kDa protein antigen from M. bovis BCG. This responsiveness is comprised of T cell proliferation and IFN production. The inventors have discovered that BTHR to the carrier PPD is stronger than that to 10 kDa M. tuberculosis and 10 kDa M. leprae proteins. However, the lymphoproliferative response to IFN secretion in sensitized animals and subjects appear to be at least identical between crude PPD and clone- expressed gene products of M. tuberculosis. Hence, the coupling of 10 kDa to the peptides of this invention may allow for improved protective in vivo responses to HIV as well as reduced unpleasant DTHR skin reactions in vaccines.

The inventors immunized BCG-primed guinea pigs at monthly intervals with 10 kDa M. leprae- and 10 kDa M. tuberculosis-PND conjugates. The vaccines were given at doses of 25 mg and 125 mg, respectively. The guinea pigs demonstrated a delayed type skin reactivity to the peptides. In addition, there was an in vitro lymphocyte antigenic response to the peptides with which the animals were immunized. Hence, a cell-mediated immune response may be acquired using 10 kDa M. leprae and 10 kDa M. tuberculosis proteins conjugated to PND.

In order to prepare the peptides of this invention, it is necessary to determine which strains of HIV infect the subjects to be treated, and which peptides of each strain would most effectively induce the production of high affinity/avidity neutralizing and/or protective HIV-specific antibodies. There are many different strains of HIV, and different strains are prevalent in different geographic areas. Therefore, the peptides in the vaccines of this invention may be geographically specific. For example, the MN strain of HIV has a high degree of prevalence in the United States. Therefore, peptides from the MN strain of HIV are effective in conjugates used to vaccinate subjects in the United States. These particular peptides and conjugates may not be effective in different geographic areas where other HIV strains are prevalent, and may have to be adjusted according to the most prevalent strains evolving in certain geographic areas. Another example is that in the United States, high affinity/avidity neutralizing and/or protective HIV-specific antibodies against the gp120 PND of the MN strain of HIV have been associated with protection. from materno-fetal HIV transmission. Therefore, peptides from the MN strain of HIV may be used in conjugates to prevent materno-fetal transmission of HIV in the United States.

Peptides which may be employed in the vaccines of this invention include, for example, those obtained from the gp120 PND of HIV. The peptides selected may include amino acids 116–131, 307–319 and 470–490 of gp120 of MN-HIV. The most effective sequences to induce the production of high affinity/avidity neutralizing and/or protective HIV-specific antibodies, which are the preferred peptide sequences for the conjugates of this invention, are as follows:

SEQ. ID. NO. 1 KRIHIGPGRAFYT
SEQ. ID. NO. 2 IYIGPGRAC
SEQ. ID. NO. 3 IAIGPGRAC
SEQ. ID. NO. 4 IHIGPGRAC
SEQ. ID. NO. 5 GPGRAFGPGRAFGPGRAFC
SEQ. ID. NO. 6 RSIHIGPGRAFYA
SEQ. ID. NO. 7 KSITKGPGRVIYA
SEQ. ID. NO. 8 KGIAIGPGRTLYA
SEQ. ID. NO. 9 SRVTLGPGRVWYT

Other peptides which may be used in the vaccines of this invention may be from the gp160 of HIV-1. Epitopes of HIV-1 gp160 have been shown to be recognized by T cells of HIV-1 infected subjects. See Clerici et al., "Interleukin-2 Production Used to Detect Antigenic Peptide Recognition By T-Helper Lymphocytes From A symptomatic HIV-Seropositive Individuals", *Nature,* Vol. 339, pages 383–386 (1989). In addition, epitopes of HIV-1 gp160 are involved in affecting the course of HIV-1 infection. Since the carrier PPD recruits T cell help, the coupling of peptides to PPD whose sequences correspond to an HIV-1 T cell epitope would result in a vaccine that is a powerful inducer of T cell response to the HIV-1 T cell epitope. Therefore, epitopes such as T1, described by Clerici et al., and HIV-1 cytotoxic T lymphocyte (CTL) epitopes present on reverse transcriptase may be used in the vaccines of this invention. (See Hosmalin et al., "An Epitope of HIV-1 Reverse Transcriptase Recognized by Both Mouse and Human CTL", *Proc. Natl. Acad Sci,* USA, Vol. 87, page 2344 (1990)). Further, these peptides, or other peptides with similar properties, may be coupled to PPD and included with the MN-PND-PPD cocktail vaccine.

Other peptides which may be used in the vaccines of the present invention include V3 loop peptides, which are linear peptides from amino acids 307–319 associated with the $V_3$ loop region. These peptides may, for example, represent THAI-I, THAI-II, MN RF, NY-5, CDC-42 and ARV: 2.

Another peptide that may be used in the vaccines of the present. invention is a gp41 peptide, for example, the 6 amino acid peptide ELDKWA shown by Katinger to be the target of a cross-neutralizing monoclonal antibody may be used in a modified form. This peptide sequence by itself was found by many investigators to be non-immunogenic. The inventors have discovered that the addition to two LL (LLEDKWA) (SEQ ID NO:10) in a repetitive motif of 16 amino acids is surprisingly highly immunogenic.

Other peptides which may be employed in the vaccines of the present invention are Nef peptides. The selection of Nef epitopes is based on the conserved features of Nef sequences, on their functional properties (Nixon, D. F., et al. *AIDS* 5:1049, 1991; Cheingsong-Popov, R., et al. *AIDS Res. & Human Retrov.* 6:1099, 1990; Schneider, et al. *AIDS Res. & Human Retrov.* 1:37, 1991; Siakkou, H., et al. *Arch. Virol* 128:81, 1993; Culmann, B., et al. *J. Immunol.* 146:1560, 1991; Yu, G., et al. *Virology* 187:46, 1991; Shugars, D. C., et al. *J. Virol.* 67:4639–4650, 1993; Venet, A., et al. *AIDS Res. & Human Retrov.* S41, 1993; Robertson, M. N., et al. *AIDS Res. & Hunman Retrov.* 9:1217–23, 1993) and on sequences found missing in patients with "non-virulent" HIV-1 disease (long-term non-progressors). Sequences known to induce both humoral and CTL responses (Cheingsong-Popov, R., et al. *AIDS Res. & Human Retrov.* 6:1099, 1990; Schneider, et al. *AIDS Res. & Human Retrov.* 1:37, 1991; Siakkou, H., et al. *Arch. Virol* 128:81, 1993; Culmann, B., et al. *J. Immunol.* 146:1560, 1991; Robertson, M. N., et al. *AIDS Res. & Human Retrov.* 9:1217–23, 1993) are selected. Other peptides that may be employed include, for example:

a. RPMTYK (SEQ ID NO: 11)—a highly conserved recognition site for phosphorylation by protein kinase C:
b. GGKWSK (SEQ ID NO:12) —a nearly invariant myristilation site which lies on the external surface of the folded nef protein.
c. PGPGIRY (SEQ ID NO:13) and GPGIGPGV (SEQ ID NO: 14) located at positions 13–138, a highly conserved region predictive of a beta turn (Shugars, D. C., et al. *J. Virol.* 67:4639–4650, 1993).

Because soluble peptides are poor immunogens due to their lack of T cell and B-cell reactive epitopes and their low molecular weight, the peptides of this invention are conjugated with different carriers to enhance immunogenicity. The methods by which these peptides are conjugated with the carriers include disulfide linkages through a C terminal peptide cysteine linkage, coupling with glutaraldehyde solution for two hours, coupling with tyrosine, or coupling with water soluble carbodiimide.

Where the carrier is PPD, PPD-negative subjects should be primed with BCG prior to conjugate vaccination. In order to determine whether a subject is PPD-negative or PPD-positive, either proliferative response testing or skin testing may be performed. For proliferative response testing, if a subject exhibits proliferative responses in vitro to peripheral blood lymphocytes to PPD, that subject is PPD-responsive. For skin testing, a subject should be exposed to intradermal 5 TU and, if negative, to 20 TU of PPD. If a subject is PPD-positive, there is no need to prime with BCG. If a subject is considered PPD-negative, that subject should receive a BCG immunization four to six weeks prior to conjugate vaccination. After BCG immunization, PPD testing should again be performed. If the results of the PPD test are positive, then the conjugate vaccine is administered to the subject.

If subjects are HIV-negative and PPD-negative, there are no limitations on BCG priming. However, if subjects are HIV-positive and PPD-negative, they may be primed with BCG only if they are still asymptotic and/or their CD4 T-cell counts exceed 200. Subjects who are HIV-positive, PPD-negative and exhibit advanced symptoms should not be primed with BCG. In addition, it is recommended that the standard British or Japanese BCG vaccines be used for priming, since these vaccines rarely induce adverse reactions in subjects.

The peptide-carrier conjugates of this invention may be administered in vaccine form, suppository form, intradermally, subcutaneously, orally, or by any other suitable route. The vaccines may be administered in any suitable form including liquid form, or in timed-release, pulse-release or slow-release mechanisms, such as virosomes. Virosomes encase viral-specific antigens in their systems and then react strongly with macrophages. Such virosomes may comprise 1–10 mg of PND peptide coupled to PPD or influenza hemagglutinin (HA), or PND in a free state associated with but not covalendy coupled with PPD or HA, 1–10 mg of HA isolated from a human strain of influenza virus, 0.1–1 mg neuraminidase (NA) isolated from a human strain of influenza virus, 0.25–0.75 mg kephalin and 100–140 mg lecithin.

The vaccines of this invention should be administered in dosage concentrations and regimens which induce high affinity/avidity antibody response. This approach is in contrast to accepted vaccination practices wherein the general goal is to elicit a higher total antibody response without specific regard to affinity/avidity of the antibody produced. Accepted vaccination practices are usually designed so as to incorporate a comparatively large amount of antigen and a dosing scheme to elicit maximal antibody titers over the shortest period of time. In contrast, the dosage and regimen schedules of the present invention allow for a limiting amount of antigen and an extended vaccination schedule so as to select for the induction of high affinity/avidity and/or neutralizing antibodies.

The vaccines of the present invention may be administered at a single site, or at multiple sites. Where the carrier to be employed in the vaccine is PPD, the preferred concentration of PPD is 2 IU–100 IU per human dose, and the preferred dosage range of the peptide is 0.1–2.5 mg. When skin testing is employed, 2–5 TU are used. The preferred ratio of peptide to PPD is in the range of 0.1:1–2:1. Where the carrier to be used in the vaccine is toxin A, the preferred dose range of peptide is in the range of 1–50 mg per human dose, and the preferred molar range of peptide to toxin A is in the range of 2:1–20:1.

Generally, small doses of vaccine antigen given at an appropriate schedule will selectively be taken up and hence stimulate immune lymphocytes expressing high affinity/avidity antibodies on their cell's surface. This is particularly true after a subject is primed with a given antigen either by natural exposure or by prior vaccination. Following primary immunization, only a comparatively small subset of primed lymphocytes will have high affinity/avidity antibodies expressed on their cell's surfaces. By subsequently immunizing with a small dose of vaccine antigen as a booster, the limiting antigen will preferentially be taken up by high affinity/avidity cells surface antibodies which will result in the expansion of such cells with the result being a preferential induction of high affinity/avidity antibodies. Multiple closely-spaced doses, especially with a large amount of antigen, can induce suppressor T cells which down-regulate the immune response, especially to a booster dose of vaccine. To circumvent this problem, a series of primary immunizations (2–3 doses of vaccines spaced 2–4 weeks apart) should be given to prime the immune system. A booster dose of vaccine is not given until at least 3–4 months have elapsed since the first dose of vaccine was given. In this manner, the population of suppressor T cells rising via primary immunization will have declined. Therefore, the preferred immunization schedule is a dose of vaccine given on days 0, 28 and 84. Subsequent booster doses can be given at 84–160 day intervals to maintain immunity.

The vaccines of this invention may comprise either a single peptide carrier conjugate or a cocktail of several different peptide carrier conjugates. In addition, it is possible to broaden neutralization activity by first immunizing with one peptide, for example MNPND (KRIHIGPGRAFYT) (SEQ ID NO:1) and then boosting at a later date with a different peptide conjugated to a carrier (for example, (GPGRAF)(SEQ ID NO:16) 3C conjugated to PPD). By doing this, a stronger antibody response against the GPGRAF (SEQ ID NO:16) epitope is induced, and since there is cross-neutralization, a broader neutralization range is obtained.

Either a single vaccination or multiple vaccinations of subjects with the peptide carrier conjugates may be used to induce the production of high affinity/avidity neutralizing and/or protective HIV-specific antibodies. The preferred dose range is 50–500 mg of peptide per conjugate. At a later date, antibody-containing fluid is extracted from the vaccinated subjects. The antibody-containing fluid is then assessed in an assay. The assay is an antigen-limited ELISA which selects for high affinity/avidity neutralizing and/or protective HIV-specific antibodies.

In order to produce this assay, microplate wells are covered with the antigen which the antibodies are reactive to, such as MN-PND, or another PND antigen derived from other seroprevalent HIV strains, in a decreasing coating concentration series as follows:

Row A—500 ng/ml
Row B—100 ng/ml
Row C—50 ng/ml
Row D—10 ng/ml
Row E—5 ng/ml
Row F—1 ng/ml
Row G—0.5 ng/ml
Row H—0 ng/ml

Where the vaccine comprises a cocktail of different peptides conjugated to carriers, all of the wells in the plate are covered with all of the peptides in the vaccine in order to determine whether there was induction of high affinity/avidity neutralizing and/or protective HIV-specific antibody production. If such antibodies were produced, a second ELISA is performed, wherein each row of the plate is covered with a separate peptide from the cocktail.

Next, antibody-containing fluid is removed from the vaccinated subjects, diluted with antibody-containing fluid diluent to a ratio of about 1:21 (sample: diluent) and added to the series of wells. The antibody-containing fluid diluent comprises a formulation of additives in a buffered solution containing thimerosal. An example of such antibody-containing fluid diluent is 0.1–0.5% casein in PBS containing 0.05% Tween-20 (pH 7.4), 0.001 % rhodamine and thimerosal. Any antibody-containing fluid may be used. Examples of antibody-containing fluid are serum, plasma, cerebral fluids and mucosal fluids. A negative control, such as anti-HIV negative human serum, and a positive control, such as anti-HIV positive human serum or anti HIV-MN-PND monoclonal antibody should also be added to wells in the ELISA plate. The plate should then be covered and incubated for about 60 minutes at about 37° C.

After incubation, the plate should be washed 5–6 times using diluted plate wash solution (phosphate buffered saline, pH 7.4 with 0.05% Tween-20 diluted with deionized water containing chloracetamide at 1:10). Use of an automatic plate washer is recommended. After washing, 100 ml per well of anti-human conjugate such as peroxidase-conjugated (goat) Fab1 anti-human IgG, anti-human IgA or anti-human secretory component (SC), diluted to 1:100,000 in conjugate diluent is added to the wells. Any conjugate diluent may be used. The conjugate diluent may comprise, for example, a formulation of additives in a buffered solution which is typically added to antibody conjugate solutions by those skilled in the art. Subsequently, the wells are incubated for 60 minutes at 37° C. and washed 5–6 times using the diluted plate wash solution. (Again, use of an automatic plate washer is recommended.)

After washing, 200 ml of substrate such as O-phenylenediamine (o-PD) tablets, diluted (to 1 tablet per 12 ml of diluent) with hydrogen peroxide in a citrate buffer is added per well. The wells are then incubated in the dark for 30 minutes at room temperature. The reaction is then stopped by adding 50 ml per well of 4N sulfuric acid. The plate may then be read in a microplate spectrophotometer at an absorbance of 492 nm. (Use of a 620 nm reference filter is recommended.)

For the controls, the human negative control values should average around 0.050. The cutoff should be around 0.100. The human positive control should filter out at least to the fifth well (5 ng/ml).

For the antibody-containing fluid, if the absorbance value is greater than the cutoff in the fourth row or less, the antibody. in the fluid is low affinity. If the absorbance value is greater than the cutoff in the fifth row or more (5 ng/ml), the antibody is medium affinity. If the absorbance value is greater than the cutoff in the fifth row or more (less than or equal to 5 ng/ml), the antibody is high affinity. A displacement assay may then be set up to ascertain the high affinity antibodies.

The affinity of the elicited antibodies (in vivo and in vitro) may be further assessed using the PHARMACIA BIACORI System, which is a biosensor-based technology (Biospecific Interaction Analysis, (BIA) which assesses biomolecular interactions to the picomolar range without the need for labels (radioactive or fluorescent). BIA measures the KA and kDa of molecules bound to a surface with molecules in free solutions. By reflecting a beam of light on a miniature sensing surface, it is possible to obtain quantitative kinetic data about antigen/antibody binding (association-dissociation constraints).

Another method of determining whether antibodies are high affinity/avidity is the use of an immunoassay wherein an indirect ELISA is prepared by coating a solid phase with one or more synthetic peptides derived from one or more different HIV strains, wherein each peptide comprises an antigen including HIV PND. On the solid phase, a series of assays can be prepared wherein each peptide is coated at varying concentrations,. from the nanomole to the femtomole range. The immobilized peptide is then contacted with sera from the subjects vaccinated with the conjugates of this invention. Bound antibodies are detected by the addition of an enzyme labeled or gold labeled anti-species conjugate. The color generated is proportional to the concentration of high affinity/avidity antibodies. Suboptimal or rate-limiting antibody coating concentrations are used to. select out neutralizing antibodies so that the ELISA results are correlated with the result of virus neutralization.

The solid phase ELISA can also utilize a secondary antibody against human secretory component or IgA. This assay can then rapidly detect protective antibodies in mucosal secretions such as saliva or cervicovaginal fluid, or serum IgA antibodies. Since IgA does not cross the placenta, the presence of such antibodies in spinal cord blood allows for the early detection of fetal HIV infection.

In order to achieve maximal assay sensitivity, antigen-coating concentrations to be applied to the solid phase ELISA should represent the minimal antigen concentration which is on the upper plateau, i.e., maximum assay response. This area represents the maximal separation of specific from non-specific signals. Coating concentrations in the low end of the titration curve represent an insensitive assay since a large proportion of an individual's immune response would be missed.

As discussed above, suboptimal antigen concentrations may be utilized to eliminate weak antigen-antibody interactions. For example, it is generally understood that the coating of solid surfaces by antigens involve titrating the antigen for reactivity using a standard antiserum. Such titrations typically yield a sigmoidal-shaped curve of assay response. At high antigen coating concentrations which saturate the solid phase, a maximal assay response will occur. This is seen as a "plateau", a region of the titration curve which shows little change in the amount of antibody detected regardless of the change in the amount of antigen. As antigen concentrations are lowered to non-saturating or "suboptimal" levels, assay responses decrease proportionally. Hence, an antigen-coating concentration which represents the minimal antigen concentration which is on the upper plateau should be utilized in the solid phase ELISA of this invention.

The conjugate vaccines which have induced the production of high affinity/avidity neutralizing and/or protective HIV-specific antibodies, such antibodies being selected for by the ELISA, are "copied". The "copies" are then used in the treatment and transmission prevention of HIV.

EXAMPLE I

Immunization of Mice with Conjugates of Peptides Coupled to Carriers KLH, PPD, Avidin and Tetanus Mice were immunized with peptide KRIHIGPGRAFYT (SEQ ID NO:1) (MN peptide or MN-PND) coupled to different carriers. Five mice were immunized with the MN peptide coupled to Keyhole Limpet Hemocyanin (KLH) as described in *Methods Enzyol.,* 70:159 (1980). The mice were bled and antibody titers directed against MN-PND were determined by an ELISA specific for MN-PND. Serum at a 1:1400 dilution obtained from mice immunized with the KLH-MN-PND conjugate had optical densities of 3.85 (K0), 0.598 (K1), 1.762 (K2), 0.282 (K3), and 0.356 (K4) with a background of less than 0.1. Four months later, the mice were boosted with KLH-MN-PND and then the sera was assayed for reactivity. This data is outlined in Table 1. All of the mice immunized had high titers and high affinity antibodies to MN-PND. Mouse K4 was sacrificed. Its spleen was harvested and used to develop monoclonal antibodies to MN-PND. Monoclonal antibodies recognizing MN-PND were generated, some of which were neutralizing.

TABLE 1

Reactivity of mice immunized with MN-PND coupled to KLH

| MN-PND | CONTROL | | KO | | KI | | K2 | | K3 | | K4 |
|---|---|---|---|---|---|---|---|---|---|---|---|
| (ng/ml) | 4/11/90 | 4/20/90 | 4/11/90 | 4/20/90 | 4/11/90 | 4/20/90 | 4/11/90 | 4/20/90 | 4/11/90 | 4/20/90 | 4/11/90 |
| 10000 | 0.06 | 0.058 | 0.099 | 2.277 | 0.604 | 2.26 | 0.145 | 0.89 | 0.096 | 2.714 | 0.166 |
| 5000 | 0.054 | 0.056 | 0.151 | 1.946 | 0.173 | 2.098 | 0.076 | 0.279 | 0.075 | 1.704 | 0.108 |
| 1000 | 0.093 | 0.056 | 0.073 | 1.096 | 0.1312 | 1.79 | 0.125 | 0.405 | 0.075 | 2.054 | 0.165 |
| 500 | 0.094 | 0.056 | 0.073 | 1.231 | 0.105 | 1.23 | 0.111 | 0.268 | 0.101 | 1.729 | 0.135 |
| 100 | 0.055 | 0.053 | 0.07 | 0.229 | 0.069 | 0.423 | 0.084 | 0.149 | 0.091 | 1.018 | 0.118 |
| 50 | 0.062 | 0.057 | 0.112 | 0.477 | 0.108 | 0.389 | 0.107 | 0.254 | 0.094 | 0.748 | 0.144 |
| 10 | 0.059 | 0.059 | 0.083 | 0.14 | 0.094 | 0.239 | 0.45 | 0.093 | 0.105 | 0.578 | 0.136 |
| 1 | 0.061 | 0.057 | 0.074 | 0.11 | 0.091 | 0.091 | 0.171 | 0.099 | 0.078 | 0.261 | 0.161 |

EXAMPLE II

Immunization of Guinea Pigs with Conjugates of Peptides Coupled to Carrier Toxin A Production of PND-Toxin A Conjugate. One gram of solid carbodiimide was added to 100 mg of toxin A derivatized with adipic acid dehydrazide (TA-ADH, 5.9 mg/ml in phosphate buffered saline, pH 7.4; PBS). The pH was adjusted to 4.8 by the addition of 0.3N HCl. To this mixture 50 mg of MN-PND peptide in 2.5 ml of pyrogen-free water was slowly added under constant stirring. The mixture was stirred for 3 hours at ambient temperature. The mixture was filter sterilized using a 0.45 mm filter unit and passed through a Sephadex G75 column to separate the conjugate from reactants. The conjugate-containing fraction which eluted in the void volume was concentrated, dialyzed against PBS and filter sterilized. The conjugate was diluted to 200 mg total protein/ml in PBS and absorbed into $Al(OH)_3$.

Immunization Studies. Three guinea pigs were vaccinated intramuscularly on days 0 and 14 with 50 mg of absorbed conjugate. Serum samples were obtained on days 0, 14 and 28. An anti-MN-PND peptide ELISA was performed by coating plates with MN-PND peptide, reacting wells with serial dilutions of antisera, and after washing, reacting plates with an anti-guinea pig IgG antibody. As shown in Table 2 below, this conjugate did not stimulate an anti-MN-PND antibody response.

TABLE 2

| Day | mean ELISA titer |
|---|---|
| 0 | 1,4 |
| 14 | 1,8 |
| 28 | 1,0 |

EXAMPLE III

Immunization of Mice and Guinea Pigs with Conjugates of Peptides Coupled to Carrier Toxin A Mice and guinea pigs were immunized with MN-PND coupled to *Pseudomonas aeruginosa* exotoxin A (toxin A) with a ratio of peptide to carrier of 3:1. In addition, the MN-PND lacked a tyrosine residue next to the carboxy terminus. The animals were immunized on days 0 and 14. Sera was obtained at days 0, 14, and 28. The doses used were 5 and 25 mg in the guinea pigs and 2 and 10 mg in the mice. The immunizations were given as either conjugate alone or in alum. None of the sera obtained from these immunizations had any reactivity to MN-PND. This was probably due to either the immunogenicity of toxin A, coupling problems or the dosage used. Table 3, below, shows the ability of sera from guinea pigs immunized with MN-PND-toxin A+PPD to neutralize the MN strain of HIV. The animals were immunized at days 0 and 14. Vales are for sera collected on day 28.

TABLE 3

| | GUINEA PIG SERA | | | |
|---|---|---|---|---|
| Serum Dilution | 1:25 | 1:50 | 1:100 | 1:200 |
| HIV-MN Control | 115,030 | 130,400 | 126,400 | 135,030 |
| Control Serum | 84,890 | 86,690 | 85,860 | 90,630 |
| 82 14 1:20 titer | 940 (98.9%) | 1,123 (98.8%) | 1,891 (97.8%) | 2,171 (97.7%) |
| 82 17 1:20 titer | 3,990 (95.3%) | 80,700 (7.0%) | 85,590 (0.4%) | 90,610 (0.1%) |
| 82 18 1:200 titer | 866 (99.0%) | 1,079 (98.8%) | 1,067 (96.8%) | 1,538 (98.4%) |
| 82 19 | 2,999 (96.5%) | 5,098 (94.2%) | 13,110 (77.8%) | 28,070 (69.1%) |
| 82 20 | 2,589 (97.0%) | 2,847 (96.8%) | 2,804 (96.8%) | 5,111 (91.4%) |

Percentage calculated on Control Serum

EXAMPLE IV
Immunization of Guinea Pigs with Conjugates of Peptides Coupled to Carrier PPD Preparation of PPD-MN-PND Conjugate. 4 mg of MN-PND in 400 ml of sterile distilled $H_2O$ was mixed with 4 ml of sterile PPD-RT23 (1 mg/ml). Carrier PPD-RT23 was obtained from Statens Serum Institute, Copenhagen, Denmark. Carrier PPD-298 was obtained from Connaught Laboratories, Willowdale, Toronto. PPD-298-H2O signifies that the conjugation of the PND-MN peptide and the PPD-298 carrier was performed in water. PPD-298-PBS signifies that the conjugation of the PND-MN peptide and the PPD-298 carrier was performed in PBS. 45 ml of 0.2% glutaraldehyde was then added to the PPD-MN-PND solution, mixed by vortexing and incubated in the dark at 22° C. for 30 min. An additional 20 ml of 0.2% glutaraldehyde was added and the solution was incubated for 90 min. The solution appeared opalescent at this time. The reaction mixture was transferred aseptically into a sterile dialysis tubing and dialyzed against 1 liter of sterile PBS at 4° C. for 24 hours. The concentration of PPD was calculated by dividing the total amount of PPD added to the reaction mixture by the final volume of the sample after dialysis. An aliquot of the conjugate was diluted in sterile pyrogen-free PBS to 20 mg of PPD per ml (0.1000 E/ml) for determining the sterility and general safety of the vaccine preparation according to the guidelines of European Pharmacopeia. The remainder of the sample was kept in undiluted form at 4° C.

Given the heterogeneous nature of PPD, it was not possible to accurately determine the ratio of PPD: MN-PND conjugate by amino acid analysis. Therefore, incorporation of $^{125}I$ MN-PND peptide into PPD in the presence of glutaraldehyde was determined.

A MN-PND (10 mg in 0.2 ml $H_2O$) solution was prepared. A $^{125}I$ (1 mCi diluted with 10 ml of 0.1 N NaOH) solution was prepared. Ten (10) ml of $^{125}I$ solution was added to 0.2 ml MN-PND solution. To this 80 ml chloramine T (2 mg/ml in 0.1 M $NaPO_4$, pH 7.2) was added. The solution was mixed for 1 minute at room temperature and immediately applied to a Sephadex G-10 column equilibrated in PBS, pH 7.4. Fractions (30 sec) were collected. The radioactivity per fraction was determined and the peak fractions collected and pooled. The total MN-PND peptide present in the pool was calculated by Lowry using the Folin reagent. A concentration of 3.23 mg/ml was yielded. The total 125I MN-PND was 68,348 CPM/mg MN-PND.

Estimation of the $^{125}I$ MN-PND incorporation into PPD was determined as follows: To 2 ml PBS, pH 7.4, were added 2 mg PPD together with 2 mg $^{125}I$ MN-PND. Coupling was performed by the addition of glutaraldehyde. After coupling, the conjugate was extensively dialyzed against PBS, pH 7.4. The conjugate was removed from the dialysis tubing. A total of 710,000 CPM/2 mg PPD was incorporated, corresponding to 1.29 mg MN-PND. Total incorporation of the MN-PND peptide was roughly 59% (710,000 CPM of total 1,200,000 CPM added). Therefore, 2 mg of PPD contained 1.29 mg of MN-PND, assuming total recovery of PPD. The ratio of PPD to MN-PND was 1:0.645. (A human dose of 50 IU of PPD would contain approximately 0.645 mg of MN-PND.)

Immunogenicity of PPD-MN-PND Conjugate in Guinea Pigs. Groups of 5 guinea pigs were primed with $10^6$ CFU of BCG or saline. The animals were then immunized with 10 or 50 mg of PPD-MN-PND conjugate in 0.1 ml PBS 14 and 28 days after priming. The animals were bled at 14, 28 and 42 days after priming. The sera was then assayed in an MN-PND ELISA to determine immunogenicity of the PPD-MN-PND conjugate.

Protocol for MN-PND HIV ELISA. Dynatech polystyrene plates were coated with 100 ml of a 1.0 mg/ml of MN-PND (in carbonate buffer, pH 9.6) at 22° C. overnight. The solution was removed and then blocked with 100 ml of a 1 mg/ml solution of Bovine Serum Albumin (BSA) in PBS (pH 7.4) for 1 hour at 22° C. A 100 ml of 2-fold serial dilutions of sera in PBS-tween (ph 7.4) starting at 1:20 were dispensed into each well and the plates incubated for 3 hours. The plates were washed 3 times with 300 ml of PBS-TWEEN. 100 ml of peroxidase-conjugated rabbit anti-guinea pig IgG (1:2500 in PBS TWEEN, Nordic Immunology, Tilburg, The Netherlands) was added to each well and the plates were incubated for 2 hours. The plates were washed three times in PBS-TWEEN and 100 ml of p-nitrophenyl phosphate (Merck) was added to the wells. The plates were then incubated for 60 minutes at 22° C. The absorbance at 405 nm was measured using a Dynatech MR5000 Microtiter Plate Reader (Dynatech, Switzerland). The serum dilution at the linear part of the titration curve (between 0.15 and 0.6) was multiplied by the reciprocal corresponding dilution of the serum and expressed as ELISA units.

As shown in Table 4 below, priming of the guinea pigs with BCG and subsequent immunization with the PPD-MN-PND conjugate induced the production of high affinity/avidity neutralizing and/or protective HIV-specific antibodies. The antibody titers of the guinea pigs primed with BCG were much higher than the titers of the guinea pigs not primed with BCG, indicating that priming with BCG prior to conjugate immunization causes the immune system to respond better to conjugate immunization, thereby more effectively inducing the production of high affinity/avidity neutralizing and/or protective HIV-specific antibodies. The antibody titers of the guinea pigs not primed with BCG (group d) were not statistically higher than guinea pigs not immunized with the PPD-MN-PND conjugate vaccine (group a).

TABLE 4

Immunogenicity of PND-MN-PPD Conjugates in BCG Primed and Unprimed Guinea Pigs

| Vaccine | Dose (μg) | Geometric Mean Elisa unit (range) |
|---|---|---|
| — | — | 1.6 (1.2–2.7)[a] |
| PPD-MN-PND | 10 | 2.4 (2.14–2.78)[d] |
| PPD-MN-PND | 50 | 6.0 (5.68–6.12)[d] |
| PPD-MN-PND | 10 | 121.1 (5.40–462.1)[b] |
| PPD-MN-PND | 50 | 14.1 (5.56–25.68)[c] |
| RT23 | 10 | 21.0 (6.7–70.8)[b] |
| RT23 | 50 | 180.5 (49.4–692.5)[b] |
| PPD-298-H20 | 10 | 31.1 (4.9–181.9)[b] |
| PPD-298-H20 | 50 | 142.2 (31.0–393.0)[c] |
| PPD-298-PBS | 10 | 22.8 (6.3–232.0)[c] |
| PPD-298-PBS | 50 | 63.2 (9.6–858.9)[c] |

[a]Geometric Mean Elisa units of Pre immune sera from 4 guinea pigs.
[b]Geometric Mean Elisa units of post immune sera from 4 guinea pigs.
[c]Geometric Mean Elisa units of post immune sera from 3 guinea pigs.
[d]Guinea pigs not primed with BCG.

EXAMPLE V

Immunization of Guinea Pigs and Mice with Conjugates of Peptides Coupled to Carrier PPD Guinea pigs and mice were immunized with MN-PND coupled to 2 types of PPD. Some of the PPD-immunized animals were first primed with BCG. Table 5 shows the immunoreactivity of the animals to MN-PND. Table 6 shows the titration of serum reactivity to MN-PND. Table 7 shows the affinity to MN-PND as measured by antigen-limited ELISA. Samples were assayed for neutralization activity. Results obtained indicated that neither of the sera had neutralizing activity to MN-HIV.

TABLE 5

Reactivity of Mice and Guinea Pigs immunized with MN-PPD coupled to PPD

| | GUINEA PIG | | | | MICE | | |
|---|---|---|---|---|---|---|---|
| | SAMPLE | DAY | O.D. | | SAMPLE | DAY | O.D. |
| | | 0 | 0 | 0.15 | | 1/2/3/4 | 0 | 0.01 |
| | | 0 | 0 | 0.119 | | | | |
| MN-PND-PPD 10 ug | 7281 | 28 | 0.14 | MD-PND-PPD 2 ug | GROUP #1 | 28 | 0.026 |
| | 7282 | 28 | 0.62 | | GROUP #1 | 28 | 0.018 |
| | 7284 | 28 | 0.312 | | GROUP #1 | 28 | 0.023 |
| | 7285 | 28 | 0.43 | MN-PND-PPD 10 ug | GROUP #2 | 28 | 0.026 |
| MN-PND-PPD 50 ug | 7286 | 28 | 2.4 | | GROUP #2 | 28 | 0.02 |
| | 7287 | 28 | 2.9 | | GROUP #2 | 28 | 0.043 |
| | 7288 | 28 | 1.448 | | GROUP #2 | 28 | 0.02 |
| BCG/MN-PND-PPD 10 ug | 7291 | 42 | 3.6 | BCG/MN-PND-PPD 2 ug | GROUP #3 | 28 | 0.026 |
| | 7292 | 28 | 0.27 | | GROUP #3 | 42 | 0.075 |
| | 7293 | 42 | 3.6 | | GROUP #3 | 42 | 0.469 |
| | 7294 | 42 | 3.1 | | GROUP #3 | 42 | 1.7 |
| | 7295 | 42 | 3.3 | | GROUP #3 | 42 | 2.4 |
| BCG/MN-PND-PPD 50 ug | 7296 | 42 | 3.39 | BCG/MN-PND-PPD 10 ug | GROUP #4 | 28 | 0.098 |
| | 7298 | 42 | 3.5 | | GROUP #4 | 42 | 1.3 |
| | 7299 | | 0.275 | | GROUP #4 | 42 | 2.1 |
| | 7300 | 42 | 3.96 | | | | |

TABLE 6

Titration of guinea pig anti-MN-PND Serum

| DILUTION | SAMPLE | DAY | 1:20 | 1:100 | 1:500 | 1:1000 | 1:2500 |
|---|---|---|---|---|---|---|---|
| | 0 | 0 | 0.15 | 0.07 | 0.05 | 0.05 | 0.04 |
| MN-PND-PPD 50 ug | 7286 | 28 | 2.40 | 0.36 | 0.09 | 0.07 | 0.05 |
| | 7287 | 28 | 2.90 | 0.40 | 0.12 | 0.09 | 0.07 |
| | 7288 | 28 | 1.45 | 0.17 | 0.07 | 0.08 | 0.06 |
| BCG/MN-PND-PPD 10 ug | 7291 | 42 | 3.60 | 3.71 | 3.67 | 3.30 | 1.61 |
| | 7292 | 28 | 0.27 | | | | |
| | 7293 | 42 | 3.60 | 0.52 | 0.12 | 0.08 | 0.07 |
| | 7294 | 42 | 3.10 | 1.30 | 0.27 | 0.18 | 0.13 |
| | 7295 | 42 | 3.10 | 1.50 | 0.03 | 0.18 | 0.13 |
| BCG/MN-PND-PPD 50 ug | 7296 | 42 | 3.39 | 1.17 | 0.27 | 0.15 | 0.10 |
| | 7298 | 42 | 3.50 | 0.24 | 0.09 | 0.06 | 0.04 |
| | 7299 | | 0.28 | | | | |
| | 7300 | 42 | 3.96 | 3.76 | 3.81 | 2.48 | 0.95 |

TABLE 7

Antigen limited MN-PND ELISA of guinea pig samples

| | | | IMMUNIZATION | | | | | | | | |
|---|---|---|---|---|---|---|---|---|---|---|---|
| MN-PND | | | HN-PND-PPD 50 ug | | | BCG/HIV-PPD-PND 10 ug | | | | BCG/MN-PND-PPD 50 ug | |
| (ng/well) | SAMPLE | 0 | 7286 | 7287 | 7288 | 7291 | 7293 | 7294 | 7295 | 7296 | 7298 | 7300 |
| 500 | | 0.21 | 2.13 | 2.84 | 0.98 | 3.95 | 3.64 | 3.99 | 3.99 | 3.49 | 3.50 | 3.84 |
| 100 | | 0.32 | 2.47 | 2.89 | 1.08 | 3.50 | 3.30 | 3.53 | 3.59 | 3.60 | 3.21 | 3.75 |
| 50 | | 0.31 | 1.97 | 2.49 | 0.77 | 3.96 | 3.08 | 3.53 | 3.46 | 3.41 | 2.18 | 3.82 |
| 10 | | 0.22 | 0.86 | 0.63 | 0.50 | 3.96 | 1.35 | 1.16 | 2.60 | 0.82 | 0.52 | 3.01 |
| 5 | | 0.26 | 0.15 | 0.37 | 0.36 | 3.53 | 0.46 | 0.56 | 1.59 | 0.44 | 0.29 | 1.28 |
| 1 | | 0.21 | 0.18 | 0.26 | 0.30 | 0.73 | 0.31 | 0.25 | 0.29 | 0.25 | 0.24 | 0.24 |
| 0.5 | | 0.18 | 0.16 | 0.23 | 0.24 | 0.72 | 0.33 | 0.21 | 0.24 | 0.23 | 0.22 | 0.22 |

EXAMPLE VI

Immunization of Humans with Conjugates of Peptides Coupled to Carrier PPD

Based on the immunogenicity of the PPD-MN-PND conjugates in guinea pigs illustrated in EXAMPLE V, five PPD-positive humans were immunized with this conjugate. The reactivity of sera from the 5 human volunteers was assayed one month after immunization with PPD-MN-PND. No significant IgG or IgM to MN-PND was detected. The sera was again assayed two months after immunization. Table 8 shows the results of the assay.

TABLE 8

Reactivity of human volunteers to MN-PPD-PND
2 months after immunization

|  | Specific Absorbance (410 nm) | | |
| --- | --- | --- | --- |
| Negative Control | 0.067 | 0.054 | 0.063 |
| Negative Control | 0.099 | 0.059 | 0.096 |
| Positive Control | 0.3 | 0.434 | 0.357 |
| Volunteer #1 | 0.229 | 0.463 | 0.388 |
| Volunteer #2 | 0.054 | 0.068 | 0.068 |
| Volunteer #3 | 0.096 | 0.114 | 0.105 |
| Volunteer #4 | 0.055 | 0.065 | 0.071 |
| Volunteer #5 | 0.049 | 0.055 | 0.076 |

The volunteers were immunized a second time. Serum samples were obtained about 14 days and 28 days after each immunization and prior to immunization. As shown in Table 9 below, after the second immunization, one subject was a very strong responder, one was a "borderline" responder and 2 were non-responders.

TABLE 9

Assay for reactivity to MN-PND was performed
in triplicate on the samples obtained 44 days
after immunization.

| Sample #1 | .370 ± .057 |
| --- | --- |
| Sample #2 | .063 ± .038 |
| Sample #3 | .105 ± .004 |
| Sample #4 | .063 ± .004 |
| Positive | .363 ± .031 |
| Negative #1 | .084 ± .010 |
| Negative #2 | .061 ± .003 |

Sample #1 is significantly different from negative controls ($p < .001$) and sample #3 may be significantly different from negative control ($p < .05$).

The volunteers were immunized a third time. After the third immunization with the PPD-MN-PND conjugate, the serum of one volunteer had a high titer of high affinity/avidity HIV-specific antibodies. Upon exposure to MN-PND, the lymphocytes responded in vitro by proliferation and secretion of interleukin-2. This shows that an entire immune response was induced. B-cell humoral immunity response was induced, as evidenced by the production of antibodies. T-cell immunity response was also induced, as shown by the proliferation of T-cells upon exposure to the conjugate, and as shown by the secretion of interleukin-2, which is a mediator of the immune response. The other three serum samples showed no significant immunological response. The fact that high affinity/avidity HIV-specific antibodies are found more frequently in HIV infected asymptomatic subjects indicates that such antibodies are protective.

EXAMPLE VII

Synthesis of Peptides and Immunization of Mice with Conjugates of Synthesized Peptides Coupled to Carrier KLH In addition to MN-PND, four other peptides were synthesized. These peptides are 282 (GPGRAFGPGRAFGPGRAFC) (SEQ ID NO:5), 283 (IYIGPGRAC) (SEQ ID NO:2), 284 (IAIGPGRAC)(SEQ ID NO:3) and 285 (IHIGPGRAC) (SEQ ID NO:4). These peptides were coupled to KLH as described above. Five mice were immunized with each peptide conjugate and boosted 2 months later. Serum was obtained. FIG. 1 shows the reactivity to each of the peptides. FIG. 2 shows the affinity/avidity of the mice with the highest titers of antibody. There was variable immunogenicity of the peptides. 284 was the most highly immunogenic, and 285 was not immunogenic at all. Some mice immunized with 283 and 284 had very low reactivity to MN-PND. This was not just an ELISA artifact as evidenced by the fact that when peptide 282 was incubated with serum from mouse 283-5 prior to performing the ELISA, peptide 282 bound to (competed with) the antibodies in the mouse serum, whereas the MN peptide did not compete with the mouse serum antibodies when incubated therewith. In contrast, peptides 282 and MN both were able to compete with (bind to) the antibodies in the serum of mouse 284-4 (see FIG. 3).

EXAMPLE VIII

Immunoreactivity of Humans to Synthesized Peptides

Based on the observation of the differential immunogenicity of the PND peptides, sera from 20 HIV-positive subjects was assessed for reactivity with the five indicated peptides. (See Table 10). Eight samples reacted with at least 4 out of 5 peptides, one sample. with 3 out of 5, one sample with 2 out of 5 peptides, and six samples with only 1 out of 5 peptides. One sample was negative, and three samples had high backgrounds. Of eight subjects who had high affinity antibodies to MN-PND, two subjects had high affinity antibodies to 282. In addition, of the eight subjects who had high affinity antibodies to MN-PND, 5 recognized 5out of 5 peptides, one recognized 4 out of 5 peptides, 1 recognized 3 out of 5 peptides and 1 recognized 1 out of 5 peptides. This indicates that within the group of subjects with high affinity/avidity antibodies to MN-PND, there exist subgroups, some of which may be more protective against HIV. In addition this may have clinical prognostic significance which will affect the inclusion of peptides in a multivalent vaccine.

TABLE 10

| SAMPLE | PEPTIDE | Reactivity | Affinity/Avidity +/− | CONCENTRATION (ng/ml) (ng/ml) 5000 | 1000 | 500 | 100 | 50 | 10 | 5 | 0 |
|---|---|---|---|---|---|---|---|---|---|---|---|
| Negative | KRIHIGPGRAFYT (SEQ ID NO: 1) | | | 0.014 | | | | | | | |
| | " | | | 0.018 | | | | | | | |
| | (GPGRAF)(SEQ ID NO: 16) 3C | | | 0.02 | | | | | | | |
| | " | | | 0.035 | | | | | | | |
| | IYIGPGRAC (SEQ ID NO: 2) | | | 0.03 | | | | | | | |
| | " | | | 0.018 | | | | | | | |
| | IAIGPGRAC (SEQ ID NO: 3) | | | 0.025 | | | | | | | |
| | " | | | 0.021 | | | | | | | |
| | IHIGPGRAC (SEQ ID NO: 4) | | | 0.033 | | | | | | | |
| | " | | | 0.019 | | | | | | | |
| 2207 | KRIHIGPGRAFYT | + | | 2.949 | 3.089 | 2.909 | 2.426 | 1.828 | 0.857 | 0.608 | 0.469 |
| | (GPGRAF)3C | + | | 1.544 | 0.579 | 1.123 | 0.607 | 0.861 | 0.486 | 0.617 | 0.775 |

TABLE 10-continued

|  |  | Affinity/Avidity |  |  | CONCENTRATION (ng/ml) |  |  |  |  |  |  |  |
|---|---|---|---|---|---|---|---|---|---|---|---|---|---|
| SAMPLE | PEPTIDE | Reactivity | +/− | (ng/ml) | 5000 | 1000 | 500 | 100 | 50 | 10 | 5 | 0 |
|  | IYIGPGRAC | + |  |  | 2.884 | 2.444 | 2.544 | 0.422 | 0.787 | 0.496 | 0.776 | 0.711 |
|  | IAIGPGRAC | + |  |  | 3.039 | 2.78 | 1.985 | 0.484 | 0.894 | 0.677 | 0.832 | 0.965 |
|  | IHIGPGRAC | + |  |  | 3.126 | 2.981 | 2.789 | 0.773 | 1.047 | 0.634 | 1.115 | 1.083 |
| 2434 | KRIHIGPGRAFYT | + |  |  | 1.808 | 1.517 | 0.828 | 0.298 | 0.3 | 0.272 | 0.178 | 0.324 |
|  | (GPGRAF)3C | + |  |  | 3.392 | 2.979 | 2.857 | 2.03 | 1.899 | 0.097 | 0.842 | 1.14 |
|  | IYIGPGRAC | + |  |  | 1.661 | 1.425 | 1.32 | 0.184 | 0.746 | 0.358 | 0.628 | 0.96 |
|  | IAIGPGRAC | + |  |  | 3.128 | 2.872 | 2.028 | 0.41 | 0.677 | 0.355 | 0.32 | 0.859 |
|  | IHIGPGRAC | + |  |  | 2.136 | 1.913 | 1.512 | 0.55 | 0.367 | 0.334 | 0.632 | 0.453 |
| 2477 | KRIHIGPGRAFYT | + | + | 50 | 2.709 | 2.415 | 2.606 | 1.365 | 0.715 | 0.158 | 0.103 | 0.095 |
|  | (GPGRAF)3C | + | + | 50 | 3.2 | 2.137 | 2.212 | 0.323 | 0.385 | 0.041 | 0.074 | 0.152 |
|  | IYIGPGRAC | + | − | 1000 | 0.776 | 0.688 | 0.1 | 0.055 | 0.021 | 0.027 | 0.053 | 0.091 |
|  | IAIGPGRAC | + | − | 500 | 2.366 | 0.856 | 0.983 | 0.053 | 0.091 | 0.023 | 0.046 | 0.136 |
|  | IHIGPGRAC | + | − | 500 | 1.169 | 1.454 | 1.415 | 0.138 | 0.115 | 0.022 | 0.045 | 0.155 |
| 2529 | KRIHIGPGRAFYT | + | + | 50 | 1.668 | 1.326 | 1.284 | 0.358 | 0.223 | 0.059 | 0.061 | 0.084 |
|  | (GPGRAF)3C | + | − | 500 | 2.29 | 1.23 | 0.666 | 0.038 | 0.049 | 0.04 | 0.052 | 0.108 |
|  | IYIGPGRAC | + | − | 1000 | 0.789 | 0.303 | 0.169 | 0.038 | 0.051 | 0.031 | 0.047 | 0.079 |
|  | IAIGPGRAC | + | − | 1000 | 2.243 | 0.432 | 0.124 | 0.014 | 0.04 | 0.036 | 0.047 | 0.073 |
|  | IHIGPGRAC | + | − | 500 | 1.214 | 2.023 | 1.35 | 0.073 | 0.063 | 0.055 | 0.046 | 0.092 |
| 2234 | KRIHIGPGRAFYT | + | + | 10 | 3.049 | 2.932 | 2.547 | 1.705 | 1.334 | 0.204 | 0.111 | 0.075 |
|  | (GPGRAF)3C | + | − | 500 | 0.564 | 0.482 | 0.303 | 0.038 | 0.039 | 0.028 | 0.05 | 0.042 |
|  | IYIGPGRAC | + | − | 5000 | 0.218 | 0.118 | 0.091 | 0.027 | 0.029 | 0.026 | 0.039 | 0.039 |
|  | IAIGPGRAC | + | − | 1000 | 2.34 | 0.389 | 0.116 | 0.016 | 0.044 | 0.036 | 0.03 | 0.049 |
|  | IHIGPGRAC | + | − | 500 | 2.361 | 0.525 | 1.042 | 0.023 | 0.049 | 0.033 | 0.048 | 0.057 |
| 2488 | KRIHIGPGRAFYT | + | + | 1 | 2.983 | 3.131 | 3.012 | 2.367 | 1.777 | 0.531 | 0.307 | 0.241 |
|  | (GPGRAF)3C | + | + | 50 | 1.282 | 0.983 | 0.91 | 0.536 | 0.43 | 0.088 | 0.131 | 0.144 |
|  | IYIGPGRAC | + | − | 1000 | 0.269 | 0.226 | 0.155 | 0.092 | 0.052 | 0.079 | 0.095 | 0.126 |
|  | IAIGPGRAC | + | − | 500 | 1.204 | 0.254 | 0.223 | 0.072 | 0.028 | 0.063 | 0.054 | 0.123 |
|  | IHIGPGRAC | + | − | 500 | 2.968 | 2.829 | 2.338 | 0.135 | 0.129 | 0.077 | 0.1 | 0.115 |
| 2535 | KRIHIGPGRAFYT | + | − | 500 | 0.584 | 0.26 | 0.237 | 0.162 | 0.124 | 0.08 | 0.182 | 0.075 |
|  | (GPGRAF)3C | + | − | 500 | 2.244 | 1.274 | 0.685 | 0.071 | 0.079 | 0.076 | 0.075 | 0.082 |
|  | IYIGPGRAC | − | − | — | 0.115 | 0.091 | 0.077 | 0.07 | 0.07 | 0.06 | 0.086 | 0.099 |
|  | IAIGPGRAC | + | − | 5000 | 0.347 | 0.119 | 0.162 | 0.063 | 0.085 | 0.067 | 0.087 | 0.097 |
|  | IHIGPGRAC | + | − | 500 | 2.244 | 1.943 | 1.339 | 0.141 | 0.1 | 0.144 | 0.08 | 0.094 |
| 2126 | KRIHIGPGRAFYT | + | + | 10 | 2.136 | 1.877 | 1.627 | 0.603 | 0.485 | 0.308 | 0.177 | 0.135 |
|  | (GPGRAF)3C | + | − | 500 | 0.673 | 0.517 | 0.333 | 0.055 | 0.108 | 0.054 | 0.096 | 0.091 |
|  | IYIGPGRAC | + | − | 500 | 2.633 | 2.049 | 1.857 | 0.077 | 0.14 | 0.037 | 0.089 | 0.053 |
|  | IAIGPGRAC | + | − | 5000 | 0.266 | 0.132 | 0.099 | 0.026 | 0.03 | 0.025 | 0.041 | 0.09 |
|  | IHIGPGRAC | + | − | 500 | 2.964 | 2.612 | 2.099 | 0.106 | 0.125 | 0.049 | 0.099 | 0.02 |
| 2146 | KRIHIGPGRAFYT | + | − | 100 | 0.3 | 0.238 | 0.221 | 0.251 | 0.188 | 0.092 | 0.051 | 0.06 |
|  | (GPGRAF)3C | ? | ? | ? | 0.055 | 0.096 | 0.072 | 0.22 | 0.333 | 0.281 | 0.349 | 0.574 |
|  | IYIGPGRAC | ? | ? | ? | 0.469 | 0.423 | 0.435 | 0.201 | 0.275 | 0.258 | 0.28 | 0.489 |
|  | IAIGPGRAC | ? | ? | ? | 0.525 | 0.255 | 0.278 | 0.24 | 0.296 | 0.231 | 0.279 | 0.405 |
|  | IHIGPGRAC | ? | ? | ? | 1.002 | 0.806 | 0.683 | 0.295 | 0.45 | 0.301 | 0.442 | 0.7 |
| 2115 | KRIHIGPGRAFYT | + | − | 100 | 1.325 | 1.367 | 1.263 | 0.374 | 0.235 | 0.135 | 0.063 | 0.224 |
|  | (GPGRAF)3C | + | − | 5000 | 0.254 | 0.13 | 0.11 | 0.071 | 0.042 | 0.084 | 0.092 | 0.135 |
|  | IYIGPGRAC | + | − | 5000 | 0.237 | 0.16 | 0.254 | 0.037 | 0.042 | 0.045 | 0.046 | 0.07 |
|  | IAIGPGRAC | + | − | 5000 | 0.783 | 0.143 | 0.11 | 0.06 | 0.065 | 0.062 | 0.091 | 0.12 |
|  | IHIGPGRAC | + | − | 5000 | 0.346 | 0.187 | 0.166 | 0.058 | 0.07 | 0.058 | 0.081 | 0.168 |
| 2270 | KRIHIGPGRAFYT | + | − | 5000 | 0.339 | 0.137 | 0.104 | 0.044 | 0.044 | 0.045 | 0.038 | 0.074 |
|  | (GPGRAF)3C | + | − | 500 | 0.7 | 0.528 | 0.34 | 0.04 | 0.043 | 0.035 | 0.034 | 0.065 |
|  | IYIGPGRAC | − | − | — | 0.096 | 0.074 | 0.052 | 0.022 | 0.026 | 0.026 | 0.026 | 0.033 |
|  | IAIGPGRAC | − | − | — | 0.089 | 0.096 | 0.12 | 0.056 | 0.071 | 0.043 | 0.075 | 0.073 |
|  | IHIGPGRAC | − | − | — | 0.062 | 0.071 | 0.076 | 0.061 | 0.08 | 0.053 | 0.08 | 0.101 |
| 2125 | KRIHIGPGRAFYT | + | + | 10 | 2.683 | 2.704 | 2.652 | 1.748 | 1.416 | 0.244 | 0.124 | 0.063 |
|  | (GPGRAF)3C | + | - | 500 | 1.904 | 0.947 | 0.905 | 0.046 | 0.045 | 0.049 | 0.071 | 0.107 |
|  | IYIGPGRAC | − | − | — | 0.07 | 0.071 | 0.079 | 0.043 | 0.067 | 0.036 | 0.068 | 0.069 |
|  | AIAGPGRAC | + | − | 5000 | 0.266 | 0.132 | 0.099 | 0.026 | 0.03 | 0.025 | 0.041 | 0.039 |
|  | IHIGPGRAC | + | − | 5000 | 0.291 | 0.185 | 0.097 | 0.028 | 0.038 | 0.031 | 0.034 | 0.031 |
| 2335 | KRIHIGPGRAFYT | + | + | 10 | 1.839 | 1.194 | 2.062 | 1.533 | 1.186 | 0.313 | 0.174 | 0.1 |
|  | (GPGRAF)3C | + | − | 1000 | 0.426 | 0.349 | 0.183 | 0.032 | 0.05 | 0.021 | 0.068 | 0.126 |
|  | IYIGPGRAC | − | − | — | 0.148 | 0.073 | 0.031 | 0.022 | 0.047 | 0.026 | 0.055 | 0.098 |
|  | IAIGPGRAC | − | − | — | 0.184 | 0.123 | 0.129 | 0.043 | 0.034 | 0.034 | 0.043 | 0.098 |
|  | IHIGPGRAC | + | − | 5000 | 0.209 | 0.102 | 0.149 | 0.03 | 0.047 | 0.042 | 0.056 | 0.088 |
| 2232 | KRIHIGPGRAFYT | + | + | 50 | 1.148 | 1.083 | 0.979 | 0.537 | 0.281 | 0.078 | 0.065 | 0.075 |
|  | (GPGRAF)3C | − | − | — | 0.12 | 0.064 | 0.053 | 0.03 | 0.041 | 0.025 | 0.037 | 0.047 |
|  | IYIGPGRAC | − | − | — | 0.044 | 0.046 | 0.024 | 0.019 | 0.028 | 0.017 | 0.026 | 0.047 |
|  | IAIGPGRAC | − | − | — | 0.063 | 0.055 | 0.043 | 0.021 | 0.034 | 0.027 | 0.033 | 0.059 |
|  | IHIGPGRAC | − | − | — | 0.158 | 0.033 | 0.048 | 0.027 | 0.035 | 0.027 | 0.035 | 0.045 |
| 2436 | KRIHIGPGRAFYT | + | − | 500 | 1.306 | 0.98 | 0.579 | 0.093 | 0.057 | 0.025 | 0.026 | 0.022 |
|  | (GPGRAF)3C | − | − | — | 0.05 | 0.025 | 0.029 | 0.039 | 0.032 | 0.015 | 0.018 | 0.022 |
|  | IYIGPGRAC | − | − | — | 0.023 | 0.034 | 0.017 | 0.015 | 0.016 | 0.012 | 0.02 | 0.019 |
|  | IAIGPGRAC | − | − | — | 0.033 | 0.019 | 0.021 | 0.023 | 0.016 | 0.024 | 0.026 | 0.018 |
|  | IHIGPGRAC | − | − | — | 0.084 | 0.051 | 0.031 | 0.018 | 0.015 | 0.016 | 0.02 | 0.023 |
| 2205 | KRIHIGPGRAFYT | − | − | — | 0.094 | 0.049 | 0.064 | 0.042 | 0.055 | 0.051 | 0.055 | 0.071 |
|  | (GPGRAF)3C | + | − | 500 | 1.037 | 0.475 | 0.223 | 0.046 | 0.042 | 0.054 | 0.043 | 0.059 |

TABLE 10-continued

| SAMPLE | PEPTIDE | Affinity/Avidity Reactivity | +/− | (ng/ml) | CONCENTRATION (ng/ml) | | | | | | | |
|---|---|---|---|---|---|---|---|---|---|---|---|---|
| | | | | | 5000 | 1000 | 500 | 100 | 50 | 10 | 5 | 0 |
| | IYIGPGRAC | − | − | — | 0.113 | 0.067 | 0.065 | 0.042 | 0.045 | 0.04 | 0.041 | 0.046 |
| | IAIGPGRAC | − | − | — | 0.111 | 0.034 | 0.058 | 0.042 | 0.044 | 0.053 | 0.057 | 0.051 |
| | IHIGPGRAC | − | − | — | 0.143 | 0.105 | 0.072 | 0.023 | 0.043 | 0.042 | 0.049 | 0.063 |
| 2236 | KRIHIGPGRAFYT | − | − | — | 0.035 | 0.026 | 0.025 | 0.028 | 0.032 | 0.024 | 0.028 | 0.032 |
| | (GPGRAF)3C | − | − | — | 0.141 | 0.079 | 0.057 | 0.016 | 0.021 | 0.019 | 0.025 | 0.038 |
| | IYIGPGRAC | − | − | — | 0.043 | 0.031 | 0.032 | 0.017 | 0.017 | 0.021 | 0.016 | 0.02 |
| | IAIGPGRAC | + | − | 1000 | 2.335 | 0.914 | 0.137 | 0.018 | 0.021 | 0.023 | 0.032 | 0.033 |
| | IHIGPGRAC | − | − | — | 0.095 | 0.049 | 0.04 | 0.019 | 0.023 | 0.024 | 0.033 | 0.04 |
| 2128 | KRIHIGPGRAFYT | − | − | — | 0.173 | 0.158 | 0.113 | 0.066 | 0.058 | 0.056 | 0.051 | 0.057 |
| | (GPGRAF)3C | − | − | — | 0.196 | 0.119 | 0.08 | 0.029 | 0.035 | 0.031 | 0.043 | 0.045 |
| | IYIGPGRAC | − | − | — | 0.125 | 0.087 | 0.072 | 0.026 | 0.026 | 0.021 | 0.026 | 0.049 |
| | IAIGPGRAC | − | − | — | 0.078 | 0.034 | 0.044 | 0.025 | 0.034 | 0.027 | 0.019 | 0.049 |
| | IHIGPGRAC | + | − | 500 | 1.824 | 1.262 | 1.456 | 0.059 | 0.073 | 0.026 | 0.036 | 0.071 |
| 2332 | KRIHIGPGRAFYT | − | − | — | 0.043 | 0.04 | 0.029 | 0.034 | 0.031 | 0.028 | 0.025 | 0.028 |
| | (GPGRAF)3C | − | − | — | 0.087 | 0.048 | 0.04 | 0.021 | 0.026 | 0.022 | 0.028 | 0.051 |
| | IYIGPGRAC | − | − | — | 0.024 | 0.026 | 0.031 | 0.022 | 0.023 | 0.021 | 0.025 | 0.034 |
| | IAIGPGRAC | − | − | — | 0.03 | 0.04 | 0.041 | 0.027 | 0.024 | 0.025 | 0.033 | 0.038 |
| | IHIGPGRAC | − | − | — | 0.036 | 0.039 | 0.032 | 0.026 | 0.027 | 0.021 | 0.026 | 0.048 |
| 2437 | KRIHIGPGRAFYT | − | − | — | 0.059 | 0.052 | 0.117 | 0.121 | 0.036 | 0.036 | 0.125 | 0.098 |
| | (GPGRAF)3C | + | − | 1000 | 0.261 | 0.138 | 0.115 | 0.049 | 0.042 | 0.035 | 0.045 | 0.066 |
| | IYIGPGRAC | − | − | — | 0.032 | 0.09 | 0.077 | 0.036 | 0.044 | 0.035 | 0.054 | 0.07 |
| | IAIGPGRAC | − | − | — | 0.057 | 0.043 | 0.046 | 0.036 | 0.062 | 0.047 | 0.053 | 0.078 |
| | IHIGPGRAC | − | − | — | 0.103 | 0.087 | 0.075 | 0.042 | 0.051 | 0.04 | 0.05 | 0.07 |

As shown in Table 11, Sample #2234 bound to MN-PND when incubated with MN-PND prior to ELISA, but not with peptide 282. Peptide 282 comprises (GPGRAF) (SEQ ID NO:16) 3C, and the MN peptide contains GPGRAF (SEQ ID NO:16) enclosed by two flanking sequences (KRIHIGPGRAFYT) (SEQ ID NO:1). This implies that the bulk of reactivity to MN-PND is to the flanking sequences. The inability of Sample #2232 to bind to peptide 282 implies that there is only reactivity to flanking sequences and not to GPGRAF. Sample #2434 is difficult to interpret because of high background. Sample #2270 has strong reactivity with peptide 282 in a conjugate, but no reactivity with soluble peptide 282. This suggests the possibility that adhered peptide 282 may express an epitope recognized by the sera that is not present in soluble peptide 282. Another possibility is that there is a discordance between affinity measured by the antigen-limited ELISA and that measured by competition.

TABLE 11

| SAMPLE | PEPTIDE | plate | CONCENTRATION (ng/ml) | | | | | | | | |
|---|---|---|---|---|---|---|---|---|---|---|---|
| | | | 5000 | 1000 | 500 | 100 | 50 | 10 | 5 | 1 | 0 |
| 2234 | 0 | MN | 1.803 | 2.597 | 2.201 | 1.416 | 0.679 | 0.118 | 0.091 | 0.048 | |
| | MN | | 0.28 | 0.437 | 0.335 | 0.061 | 0.056 | 0.036 | 0.047 | 0.031 | |
| | 282 | | 1.887 | 2.191 | 1.96 | 1.51 | 0.795 | 0.139 | 0.109 | 0.046 | |
| | 0 | 282 | 0.704 | 0.567 | 0.469 | 0.182 | 0.163 | 0.077 | 0.086 | | 0.085 |
| | 282 | | 0.222 | 0.152 | 0.106 | 0.058 | 0.05 | 0.091 | 0.04 | | 0.07 |
| | MN | | 0.116 | 0.057 | 0.125 | 0.069 | 0.068 | 0.058 | 0.074 | | 0.073 |
| 2232 | 0 | MN | 1.352 | 1.36 | 1.159 | 0.788 | 0.434 | 0.114 | 0.092 | 0.088 | |
| | MN | | 0.952 | 0.927 | 0.727 | 0.286 | 0.15 | 0.069 | 0.068 | 0.089 | |
| | 282 | | 1.507 | 1.45 | 1.309 | 0.824 | 0.433 | 0.267 | 0.08 | 0.1 | |
| | 0 | 282 | 0.131 | 1.104 | 0.106 | 0.085 | 0.097 | 0.086 | 0.074 | | 0.053 |
| | 282 | | 0.124 | 0.103 | 0.103 | 0.083 | 0.108 | 0.093 | 0.074 | | 0.084 |
| | MN | | 0.114 | 0.083 | 0.097 | 0.107 | 0.091 | 0.099 | 0.098 | | 0.09 |
| 2434 | 0 | MN | 1.14 | 0.584 | 0.669 | 0.173 | 0.254 | 0.311 | 0.202 | 0.282 | |
| | MN | | 1.029 | 0.926 | 0.488 | 0.294 | 0.745 | 0.408 | 0.341 | 0.392 | |
| | 282 | | 0.644 | 0.598 | 0.35 | 0.234 | 0.266 | 0.332 | 0.287 | 0.372 | |
| | 0 | 282 | 3.133 | 3.144 | 2.959 | 1.544 | 0.699 | 0.693 | 0.611 | | 0.361 |
| | 282 | | 3.238 | 3.117 | 2.356 | 0.666 | 0.405 | 0.654 | 0.598 | | 0.556 |
| | MN | | 3.375 | 3.317 | 3.052 | 1.626 | 1.021 | 0.754 | 0.55 | | 0.588 |
| 2270 | 0 | MN | 0.07 | 0.095 | 0.066 | 0.044 | 0.056 | 0.071 | 0.071 | 0.051 | |
| | MN | | 0.097 | 0.076 | 0.105 | 0.055 | 0.05 | 0.089 | 0.058 | 0.097 | |
| | 282 | | 0.103 | 0.105 | 0.087 | 0.051 | 0.066 | 0.086 | 0.059 | 0.093 | |
| | 0 | 282 | 1.506 | 0.778 | 0.141 | 0.05 | 0.087 | 0.083 | 0.082 | | 0.073 |
| | 282 | | 1.458 | 0.809 | 0.163 | 0.07 | 0.088 | 0.073 | 0.081 | | 0.068 |
| | MN | | 1.313 | 0.838 | 0.159 | 0.088 | 0.069 | 0.079 | 0.077 | | 0.066 |

EXAMPLE IX
Immunization of Humans with Conjugates of MN-PND Coupled to Carrier PPD Twenty four subjects 23–63 years of age were tested to determine if they were PPD-positive by Mantoux skin testing for immune response at 2 IE dosage. Those who were skin test positive were not further tested by Mantoux. Those who were skin test negative were further Mantoux tested at 10 IE dosage. A total of 12 subjects were classified as PPD-positive. All twenty-four subjects were also tested by a third generation ELISA test (Abbott Envacor) to confirm that they were not HIV antibody positive. After Mantoux and HIV testing, twenty-three of the twenty-four subjects were intradermally immunized with 40–50 IU conjugates of the MN peptide (KRIHIGPGRAFYT) (SEQ ID NO:1) covalently coupled to the carrier PPD. These immunizations were performed at days 0, 14 and 28 on all twenty-three subjects. A fourth immunization (booster dose) was performed on all of the PPD-positive subjects more than three months but less than five months after day 0. Blood was drawn between and after the immunizations to determine whether the subjects produced anti-MN peptide antibody, whether this antibody possessed high affinity/avidity or was able to neutralize HIV. Table 12 shows the dates of birth of each subject, the results of Mantoux and HIV testing for each subject, and provides the immunization dates and blood withdrawal dates for the subjects.

TABLE 12

Progress Control

| Date of Birth | Mantoux 2 IE/Result | Labor-/ HIV-Test | Mantoux 10 IE/Result | Immunization #1 Day 0 | | Immunization #2 Day 14 | | Immunization #3 Day 28 | |
|---|---|---|---|---|---|---|---|---|---|
| | | | | Date | Dose | Date | Dose | Date | Dose |
| 08.24.46 | 01.27.92 neg | 01.30.92 | — | drop out | | | | | |
| 05.11.46 | 01.27.92 neg | 01.30.92 | — | 02.05.92 | 2 × 25 IE | 02.19.92 | 2 × 20 IE | 03.04.92 | 2 × 20 IE |
| 11.13.54 | 01.27.92 pos | 01.30.92 | — | 02.10.92 | 2 × 25 IE | 02.24.92 | 2 × 20 IE | 03.09.92 | 2 × 20 IE |
| 08.12.27 | 01.27.92 pos | 01.30.92 | — | 02.07.92 | 2 × 25 IE | 02.21.92 | 2 × 20 IE | 03.06.92 | 2 × 20 IE |
| 10.13.50 | 01.27.92 neg | 01.30.92 | 01.30.92 neg | 02.05.92 | 1 × 100 IE | 02.19.92 | 1 × 100 IE | 03.04.92 | 1 × 100 IE |
| 02.02.33 | 01.27.92 neg | 01.30.92 | 01.30.92 neg | 02.05.92 | 1 × 100 IE | 02.19.92 | 1 × 100 IE | 03.04.92 | 1 × 100 IE |
| 11.06.35 | 01.27.92 neg | 01.30.92 | — | 02.07.92 | 2 × 25 IE | 02.20.92 | 2 × 20 IE | 03.05.92 | 2 × 20 IE |
| 10.05.66 | 01.31.92 neg | 01.30.92 | 02.93.92 pos | 02.07.92 | 2 × 25 IE | 02.21.92 | 2 × 20 IE | 03.06.92 | 2 × 20 IE |
| 03.20.37 | 01.27.92 pos | 01.30.92 | — | 02.07.92 | 2 × 25 IE | 02.21.92 | 2 × 20 IE | 03.06.92 | 2 × 20 IE |
| 04.28.71 | 01.27.92 neg | 01.30.92 | — | 02.05.92 | 2 × 25 IE | 02.19.92 | 2 × 20 IE | 03.04.92 | 2 × 20 IE |
| 10.17.51 | 01.27.92 pos | 01.30.92 | — | 02.07.92 | 2 × 25 IE | 02.21.92 | 2 × 20 IE | 03.06.92 | 2 × 20 IE |
| 03.28.56 | 01.27.92 neg | 01.30.92 | — | drop out | | | | | |
| 03.10.50 | 01.31.92 neg | 01.31.92 | 02.03.92 neg | 02.07.92 | 1 × 100 IE | 02.24.92 | 1 × 100 IE | 03.06.92 | 1 × 100 IE |
| 10.09.48 | 01.28.92 neg | 01.31.92 | — | 02.05.92 | 2 × 25 IE | 02.19.92 | 2 × 20 IE | 03.04.92 | 2 × 20 IE |
| 02.09.31 | 01.28.92 pos | 01.31.92 | — | 02.07.92 | 2 × 25 IE | 02.21.92 | 2 × 20 IE | 03.06.92 | 2 × 20 IE |
| 10.07.58 | 01.28.92 neg | 01.31.92 | 01.30.92 neg | 02.05.92 | 1 × 100 IE | 02.19.92 | 1 × 100 IE | 03.04.92 | 1 × 100 IE |
| 12.30.28 | 01.28.92 neg | 01.31.92 | — | 02.07.92 | 2 × 25 IE | 02.21.92 | 2 × 20 IE | 03.06.92 | 2 × 20 IE |
| 04.21.30 | 01.28.92 neg | 01.31.92 | — | 02.07.92 | 2 × 25 IE | 02.21.92 | 2 × 20 IE | 03.06.92 | 2 × 20 IE |
| 09.15.41 | 01.28.92 pos | 01.31.92 | — | 02.07.92 | 2 × 25 IE | 02.24.92 | 2 × 20 IE | 03.09.92 | 2 × 20 IE |
| 01.20.42 | 01.28.92 pos | 01.31.92 | — | 02.07.92 | 2 × 25 IE | 02.21.92 | 2 × 20 IE | 03.06.92 | 2 × 20 IE |
| 01.16.47 | 01.28.92 pos | 01.31.92 | — | 02.07.92 | 2 × 25 IE | 02.21.92 | 2 × 20 IE | 03.06.92 | 2 × 20 IE |
| 05.09.51 | 01.28.92 neg | 01.31.92 | 01.30.92 pos | 02.05.92 | 2 × 25 IE | 02.19.92 | 2 × 20 IE | 03.04.92 | 2 × 20 IE |
| 01.15.14 | 01.28.92 pos | 01.31.92 | — | 02.07.92 | 2 × 25 IE | 02.21.92 | 2 × 20 IE | 03.06.92 | 2 × 20 IE |
| 05.07.44 | 02.10.92 neg | 02.13.92 | 02.10.92 neg | 02.17.92 | 2 × 25 IE | 03.02.92 | 2 × 20 IE | 03.16.92 | 2 × 20 IE |

| Date of Birth | Day 42 Date | Immunization #4 Date | Dose | Blood sample #1 | Blood sample #2 |
|---|---|---|---|---|---|
| 08.24.46 | | | | | |
| 05.11.46 | 03.18.92 | | | | |
| 11.13.54 | 02.23.92 | 5.19.92 | 2 × 20 IE | 05.25.92 | 06.09.92 |
| 08.12.27 | 03.20.92 | 5.19.92 | 2 × 20 IE | 05.25.92 | 06.15.92 |
| 10.13.50 | 03.18.92 | | | | |
| 02.02.33 | 03.18.92 | | | | |
| 11.06.35 | 03.19.92 | 5.19.92 | 2 × 20 IE | 05.25.92 | 06.09.92 |
| 10.05.66 | 03.20.92 | | | | |
| 03.20.37 | 03.20.92 | 5.19.92 | 2 × 20 IE | 05.25.92 | 06.09.92 |
| 04.28.71 | 03.18.92 | | | | |
| 10.17.51 | 03.20.92 | 5.19.92 | 2 × 20 IE | 05.25.92 | 06.09.92 |
| 03.28.56 | | | | | |
| 03.10.50 | 03.23.92 | | | | |
| 10.09.48 | 03.18.92 | | | | |
| 02.09.31 | 03.20.92 | | | | |
| 10.07.58 | 03.18.92 | | | | |
| 12.30.28 | 03.20.92 | 5.19.92 | 2 × 20 IE | 05.25.92 | 06.09.92 |
| 04.21.30 | 03.20.92 | | | | |
| 09.15.41 | 03.24.92 | | | | |
| 01.20.42 | 03.20.92 | | | | |

TABLE 12-continued

| Progress Control | | | | | | |
|---|---|---|---|---|---|---|
| | 01.16.47 | 03.20.92 | 5.19.92 | 2 × 20 IE | 05.25.92 | 06.09.92 |
| | 05.09.51 | 03.18.92 | | | | |
| | 01.15.14 | 03.20.92 | | | | |
| | 05.07.44 | 03.30.92 | 5.19.92 | 2 × 20 IE | 05.25.92 | 06.09.92 |

Table 13A shows the date of the first immunization with the conjugates and the immunization dose for each subject, as well as tuberculin (PPD) reaction and general reactions. Table 13B shows the same data for the second conjugate immunization. Table 13C shows the same data for the third conjugate immunization, and Table 13D shows the same data for those subjects immunized with the conjugates a fourth time (boosted).

TABLE 13A

Tuberculin reaction, systematic reactions after Immunization #1

| Date of Birth | Mantoux 2 IE/Result | Immunization #1 Date | Dose | Tuberculin reaction Itching, Pain, Stiffness, Redness, Swelling | General Reactions |
|---|---|---|---|---|---|
| 08.24.46 | 01.27.92 neg | drop out | | drop out | drop out |
| 05.11.46 | 01.27.92 neg | 02.05.92 | 2 × 25 IE | le: positive, not excessive<br>ri: positive, not excessive | none |
| 11.13.54 | 01.27.92 pos | 0.2.10.92 | 2 × 25 IE | le: positive, not excessive<br>ri: positive, not excessive | none |
| 08.12.27 | 01.27.92 pos | 02.07.92 | 2 × 25 IE | le: positive, not excessive<br>ri: positive, not excessive | none |
| 10.13.50 | 01.27.92 neg | 02.05.92 | 1 × 100 IE | positive, not excessive | unwell Day 1, slight |
| 02.02.33 | 01.27.92 neg | 02.05.92 | 1 × 100 IE | positive, not excessive | none |
| 11.06.35 | 01.27.92 pos | 02.07.92 | 2 × 25 IE | le: positive, not excessive<br>ri: positive, not excessive | |
| 10.05.66 | 01.31.92 neg | 02.07.92 | 2 × 25 IE | le: positive, not excessive<br>ri: positive, not excessive | none |
| 03.20.37 | 01.27.92 pos | 02.07.92 | 2 × 25 IE | le: positive, not excessive<br>ri: positive, not excessive | none |
| 04.28.70 | 01.27.92 neg | 02.05.92 | 2 × 25 IE | le: positive, not excessive<br>ri: positive, not excessive | none |
| 10.17.51 | 01.27.92 pos | 02.07.92 | 2 × 25 IE | le: positive, not excessive<br>ri: positive, not excessive | none |
| 03.28.56 | 01.27.92 neg | drop out | | drop out | drop out |
| 03.10.50 | 01.31.92 neg | 02.07.92 | 1 × 100 IE | positive, not excessive | none |
| 10.09.48 | 01.28.92 neg | 02.05.92 | 2 × 25 IE | le: positive, not excessive<br>ri: positive, not excessive | none |
| 02.09.31 | 01.28.92 pos | 02.07.92 | 2 × 25 IE | le: positive, not excessive<br>ri: positive, not excessive | sleepy Days 1 + 2, slight |
| 10.07.58 | 01.28.92 neg | 02.05.92 | 1 × 100 IE | positive, not excessive | none |
| 12.30.28 | 01.28.92 pos | 02.07.92 | 2 × 25 IE | le: positive, not excessive<br>ri: positive, not excessive | headache Days 1 + 2, slight; unwell Day 1, slight |
| 04.21.30 | 01.28.92 pos | 02.07.92 | 2 × 25 IE | le: positive, not excessive, blistering<br>ri: positive, not excessive, blistering | none |
| 09.15.41 | 01.26.92 pos | 02.07.92 | 2 × 25 IE | le: positive, not excessive, blistering<br>ri: positive, not excessive, blistering | headache + unwell Day 1, slight |
| 01.20.42 | 01.28.92 pos | 02.07.92 | 2 × 25 IE | le: positive, not excessive<br>ri: positive, not excessive | none |
| 01.16.47 | 01.28.92 pos | 02.07.92 | 2 × 25 IE | le: positive, not excessive<br>ri: positive. not excessive | none |
| 05.09.51 | 01.28.92 neg | 02.05.92 | 2 × 25 IE | le: positive, not excessive<br>ri: positive, not excessive | none |
| 01.15.44 | 01.28.92 pos | 02.07.92 | 2 × 25 IE | le: positive, not excessive<br>ri: positive, not excessive | none |
| 05.07.44 | 02.10.92 neg | 02.17.92 | 2 × 25 IE | le: positive, not excessive<br>ri: positive, not excessive | none |

TABLE 13B

Tuberculin reaction, systematic reactions after Immunization #2

| Date of Birth | Mantoux 2 IE/Result | Immunization #2 Date | Dose | Tuberculin reaction Itching, Pain, Stiffness, Redness, Swelling | General Reactions |
|---|---|---|---|---|---|
| 08.24.16 | 01.27.92 neg | drop out | | drop out | drop out |
| 05.11.46 | 01.27.92 neg | 02.05.92 | 2 × 25 IE | le: positive, not excessive<br>ri: positive, not excessive | none |
| 11.13.54 | 01.27.92 pos | 02.10.92 | 2 × 25 IE | le: positive, not excessive<br>ri: positive, not excessive | none |
| 08.12.27 | 01.27.92 pos | 02.07.92 | 2 × 25 IE | le: positive, not excessive<br>ri: positive, not excessive | none<br>none |
| 10.13.50 | 01.27.92 neg | 02.05.92 | 1 × 100 IE | positive, not excessive | headache Days 1 + 2, slight |
| 02.02.33 | 01.27.92 neg | 02.05.92 | 1 × 100 IE | positive, not excessive | |
| 11.06.35 | 01.27.92 pos | 02.07.92 | 2 × 25 IE | le: positive, not excessive<br>ri: positive, not excessive | none |
| 10.05.66 | 01.31.92 neg | 02.07.92 | 2 × 25 IE | le: positive, not excessive<br>ri: positive, not excessive | none |
| 03.20.37 | 01.27.92 pos | 02.07.92 | 2 × 25 IE | le: positive, not excessive<br>ri: positive, not excessive | none |
| 04.28.70 | 01.27.92 neg | 02.05.92 | 2 × 25 IE | le: positive, not excessive<br>ri: positive, not excessive | none |
| 10.17.51 | 01.27.92 pos | 02.07.92 | 2 × 25 IE | le: positive, not excessive<br>re: positive, not excessive | none |
| 03.28.56 | 01.27.92 neg | drop out | | drop out | drop out |
| 03.10.50 | 02.31.92 neg | 02.07.92 | 1 × 100 IE | positive, not excessive | headache Day 2, slight |
| 10.09.48 | 01.28.92 neg | 02.05.92 | 2 × 25 IE | le: positive, not excessive<br>ri: positive, not excessive | none |
| 02.09.31 | 01.28.92 pos | 02.07.92 | 2 × 25 IE | le: positive, not excessive<br>ri: positive, not excessive | fever 38.6° C. + heavy legs Day 1, slight |
| 10.07.58 | 01.28.92 neg | 02.05.92 | 1 × 100 IE | positive, not excessive | none |
| 12.30.28 | 01.28.92 pos | 02.07.92 | 2 × 25 IE | le: positive, not excessive<br>ri: positive, not excessive | dizzy Days 1–3; fever Day 1 38.6° C.; Day 37° C. |
| 04.21.30 | 01.28.92 pos | 02.07.92 | 2 × 25 IE | le: positive, not excessive<br>ri: positive, not excessive | none |
| 09.15.41 | 01.28.92 pos | 02.07.92 | 2 × 25 IE | le: positive, not excessive<br>ri: positive, not excessive | no appetite Days 2 + 3, slight |
| 01.20.42 | 01.28.92 pos | 02.07.92 | 2 × 25 IE | le: positive, not excessive<br>ri: positive, not excessive | none |
| 01.16.47 | 01.28.92 pos | 02.07.92 | 2 × 25 IE | le: positive, not excessive<br>ri: positive, not excessive | none |
| 05.09.51 | 01.28.92 neg | 02.05.92 | 2 × 25 IE | le: positive, not excessive<br>ri: positive, not excessive | headache Day 1, moderate<br>unwell + nausea Day 2, slight |
| 01.15.44 | 01.28.92 pos | 02.07.92 | 2 × 25 IE | le: positive, not excessive<br>ri: positive, not excessive | none |
| 05.07.44 | 02.10.92 neg | 02.17.92 | 2 × 25 IE | le: positive, not excessive<br>ri: positive, not excessive | none |

TABLE 13C

Tuberculin reaction, systematic reactions after Immunization #3

| Date of Birth | Mantoux 2 IE/Result | Immunization #3 Date | Dose | Tuberculin reaction Itching, Pain, Stiffness, Redness, Swelling | General Reactions |
|---|---|---|---|---|---|
| 08.24.46 | 01.27.92 neg | drop out | | drop out | drop out |
| 05.11.46 | 01.27.92 neg | 02.05.92 | 2 × 25 IE | le: positive not excessive<br>ri: positive, not excessive | none |
| 11.13.54 | 01.27.92 pos | 02.10.92 | 2 × 25 IE | le: positive, not excessive<br>ri: positive not excessive | none |
| 08.12.27 | 01.27.92 pos | 02.07.92 | 2 × 25 IE | le: positive, not excessive<br>ri: positive, not excessive | none |
| 10.13.50 | 01.27.92 neg | 02.05.92 | 1 × 100 IE | positive, not excessive | none |
| 02.02.33 | 01.27.92 neg | 02.05.92 | 1 × 100 IE | positive, not excessive | none |
| 11.06.35 | 01.27.92 pos | 02.07.92 | 2 × 25 IE | le: positive, not excessive<br>ri: positive, not excessive | headache Day 1, slight; dizzy Day 2, slight |
| 10.05.66 | 01.31.92 neg | 02.07.92 | 2 × 25 IE | le: positive, not excessive<br>ri: positive, not excessive | none |
| 03.20.37 | 01.27.92 pos | 02.07.92 | 2 × 25 IE | le: positive, not excessive<br>ri: positive, not excessive | none |
| 04.28.70 | 01.27.92 neg | 02.05.92 | 2 × 25 IE | le: positive, not excessive<br>ri: positive, not excessive | none |

TABLE 13C-continued

Tuberculin reaction, systematic reactions after Immunization #3

| Date of Birth | Mantoux 2 IE/Result | Immunization #3 Date | Dose | Tuberculin reaction Itching, Pain, Stiffness, Redness, Swelling | General Reactions |
|---|---|---|---|---|---|
| 10.17.51 | 01.27.92 pos | 02.07.92 | 2 × 25 IE | le: positive, not excessive, blister<br>re: positive, not excessive | none |
| 03.28.56 | 01.27.92 neg | drop out | | drop out | drop out |
| 03.10.50 | 01.31.92 neg | 02.07.92 | 1 × 100 IE | positive, not excessive | none |
| 10.09.48 | 01.28.92 neg | 02.05.92 | 2 × 25 IE | le: positive, not excessive<br>ri: positive, not excessive | none |
| 02.09.31 | 01.28.92 pos | 02.07.92 | 2 × 25 IE | le: positive, not excessive<br>ri: positive, not excessive | sleepy, listless Days 1 + 2<br>moderate, Fever 37.5–38° C. |
| 10.07.58 | 01.21.92 neg | 02.05.92 | 1 × 100 IE | positive, not excessive | none |
| 12.30.28 | 01.28.92 pos | 02.07.92 | 2 × 25 IE | le: positive, not excessive<br>ri: positive, not excessive | fever 37° C. Days 0–2 |
| 41.21.30 | 01.28.92 pos | 02.07.92 | 2 × 25 IE | le: positive, not excessive, but wide<br>ri: positive, not excessive | earbuzzing ri in evening, slight |
| 09.15.41 | 01.28.92 pos | 02.07.92 | 2 × 25 IE | le: positive, not excessive, blister<br>ri: positive, not excessive, blister | none |
| 01.20.42 | 01.28.92 pos | 02.07.92 | 2 × 25 IE | le: positive. not excessive<br>ri: positive, not excessive | none |
| 01.16.47 | 01.28.92 pos | 07.02.92 | 2 × 25 IE | le: positive, not excessive<br>ri: positive, not excessive | none |
| 05.09.51 | 01.28.92 neg | 05.02.92 | 2 × 25 IE | le: positive, not excessive<br>ri: positive, not excessive | none |
| 01.15.44 | 01.28.92 pos | 07.02.92 | 2 × 25 IE | le: positive, not excessive<br>ri: positive. not excessive | none |
| 05.07.44 | 02.10.92 neg | 07.02.92 | 2 × 25 IE | le: positive, not excessive<br>ri: positive, not excessive | none |

TABLE 13D

Tuberculin reaction, systematic reactions after Immunization #4

| Date of Birth | Mantoux 2 IE/Result | Immunization #4 Date | Dose | Tuberculin reaction Itching, Pain, Stiffness, Redness, Swelling | General Reactions |
|---|---|---|---|---|---|
| 08.24.46 | 01.27.92 neg | drop out | | drop out | drop out |
| 05.11.46 | 01.27.92 neg | | | | |
| 11.13.54 | 01.27.92 pos | 02.10.92 | 2 × 25 IE | le: positive, not excessive<br>ri: positive, not excessive | none |
| 08.12.27 | 01.27.92 pos | 02.07.92 | 2 × 25 IE | le: positive, not excessive<br>ri: positive, not excessive | none |
| 10.13.50 | 01.27.92 neg | | | | |
| 02.02.33 | 01.27.92 neg | | | | |
| 11.06.35 | 01.27.92 pos | 05.19.92 | 2 × 25 IE | le: positive, not excessive<br>ri: positive, not excessive | headache, unwell, nausea Day 2, slight |
| 10.05.66 | 01.31.92 neg | | | | |
| 03.20.37 | 01.27.92 pos | 02.07.92 | 2 × 25 IE | le: positive, not excessive<br>ri: positive, not excessive | none |
| 04.28.70 | 01.27.92 neg | | | | |
| 10.17.51 | 01.27.92 pos | 02.07.92 | 2 × 25 IE | le: positive, not excessive, blister<br>re: positive, not excessive | none |
| 03.28.56 | 01.27.92 neg | drop out | | drop out | drop out |
| 03.10.50 | 01.31.92 neg | | | | |
| 10.09.48 | 01.28.92 neg | | | | |
| 02.09.31 | 01.28.92 pos | | | | |
| 10.07.58 | 01.28.92 neg | | | | |
| 12.30.28 | 01.28.92 pos | 02.07.92 | 2 × 25 IE | le: positive, not excessive<br>ri: positive, not excessive | dizzy Day 1, moderate,<br>fever 37.6–38.6° C. Day 2, slight |
| 04.21.30 | 01.28.92 pos | | | | |
| 09.15.41 | 01.28.92 pos | | | | |
| 01.20.42 | 01.28.92 pos | | | | |
| 01.16.47 | 01.26.92 pos | 02.07.92 | 2 × 25 IE | le: positive, not excessive<br>ri: positive, not excessive | none |
| 05.09.11 | 01.28.92 neg | | | | |
| 01.15.44 | 01.28.92 pos | | | | |
| 05.07.44 | 02.10.92 neg | 02.17.92 | 2 × 25 IE | le: positive, not excessive<br>ri: positive, not excessive | none |

Table 14 shows the total amount of anti-MN peptide antibody produced by PPD skin test negative and skin test positive subjects after conjugate immunizations at days 1, 14, 28 and 42. The amount of antibody produced is shown by the reciprocal titers of antibody that recognize the MN peptide. No PPD-negative subjects mounted a significant antibody response. However, almost all of the PPD-positive subjects did so after the third primary immunization. The PPD skin test positive subjects immunized three times with the conjugates produced the greatest amount of antibody with GMT (geometric mean titer) rising by nearly 10-fold. GMT was derived by picking an OD value and its respective serum dilution value in the linear range of the assay, and then multiplying the serum dilution value by the OD.

TABLE 14

Total anti-MN-PND antibody after immunization with the MN-PND-PPD conjugate vaccine

| Group | Day 1 | Mean($A_{405}$) (range) Day 14 | Day 28 | Day 42 | No. of Positives/Total |
|---|---|---|---|---|---|
| PPD Skin test negative | <0.1 | 0.153 (0.086–0.224) | 0.201 (0.129–0.306) | 0.226 (0.038–0.351) | 2/9 |
| PPD Skin test positive | <0.1 | 0.170 (0.106–0.238) | 0.354 (0.11–0.753) | 0.556 (0.104–1.107) | 9/13 |

Table 15 shows, by reciprocal titer, the total amount of anti MN-PND antibody before and after the booster (fourth) immunization with the conjugates. Six the seven PPD skin test positive subjects responded to the booster immunization with a significant antibody response. Patient 24, who was PPD-negative and therefore not expected to respond, was included as a negative control.

TABLE 15

Reciprocal Titer of anti-MN-PND antibody before and after boosting

| Volunteer No. | Titer Before | After |
|---|---|---|
| 3 | 20 | 100 |
| 4 | 20 | 50 |
| 7 | 20 | >500 |
| 9 | 20 | >500 |
| 11 | 20 | >500 |
| 15 | 20 | |
| 17 | 20 | 20 |
| 18 | 20 | |
| 19 | 20 | |
| 20 | <20 | |
| 21 | <20 | 20 |
| 24* | <20 | <20 |

*PPD-negative

Table 16 shows which subjects produced high affinity/avidity antibodies in response to conjugate immunizations as well as the amounts of high affinity/avidity antibody produced by each subject, as determined by the antigen-limited ELISA described herein. PPD skin test positive subjects who received the booster immunization, subjects 7, 9, 11, 15, 17, 18 and 19, produced antibodies which were higher affinity/avidity. The highest affinity antibodies were produced by subjects 17 and 18. Boosting had no effect on the PPD-negative subject.

TABLE 16

High affinity antibody from PPD skin test positive volunteers

| Serum Probe | Amount (ng/well) MN-PND, which yielded $A_{405} \pm 0.2$* |
|---|---|
| Normal Serum | >500 |
| Positive Control | 5 |
| Volunteer No. | |
| 7 | 50 |
| 9 | 100 |
| 11 | 50 |

TABLE 16-continued

High affinity antibody from PPD skin test positive volunteers

| Serum Probe | Amount (ng/well) MN-PND, which yielded $A_{405} \pm 0.2$* |
|---|---|
| 15 | 10 |
| 17 | 5 |
| 18 | 5 |
| 19 | 50 |

*High affinity antibodies are those reacting with a coating concentration of <100 ng/well yielding an absorption of >0.2.

Table 17 shows inhibitory activity to HIV infection as evidenced by a reduction in the amount of P24 antigen produced after titer HIV-1 MN was incubated with the sera of six out of seven vaccinated subjects. Thus, antibodies produced in response to the conjugate vaccines of this invention are able to neutralize the MN strain of HIV. See data for subjects 7, 9, 15 and 17. Therefore, the vaccines of this invention are useful in the treatment and transmission prevention of HIV.

TABLE 17

Neutralization activity after third immunization with vaccines

| Experiment | pg p 24-Antigen/ml Serum 1:10 (Reduction) | (% Reduction) Serum 1:100 (Reduction) |
|---|---|---|
| Negative Control | 241806 | 242305 |
| Volunteer No. | | |
| 2 | 59105 (76%) | 157700 (36%) |
| 7 | 290 (99.9%) | 5356 (98%) |
| 9 | 181 (99.9%) | 285 (99.9%) |
| 15 | 35729 (85%) | 23729 (90%) |
| 17 | 62813 (74%) | 33137 (87%) |

TABLE 17-continued

Neutralization activity after third immunization with vaccines

| Experiment | pg p 24-Antigen/ml<br>Serum 1:10 (Reduction) | (% Reduction)<br>Serum 1:100 (Reduction) |
| --- | --- | --- |
| 18 | 308605 (0%) | 42581 (82%) |
| 19 | 130805 (46%) | 191861 (21%) |

These data are following 18 days of culturing H9 cells infected with HIV-1 MN (approx. 100 $TCID_{50}$) incubated with sera of vaccinated subjects.

The above subjects which produced anti-MN peptide high affinity/avidity antibodies were vaccinated with the MN peptide (KRIHIGPGRAFYT) (SEQ ID NO:1) covalently coupled to carrier PPD. As discussed hereinabove, the conjugate vaccines of this invention may be administered alone, or in a "cocktail" of several conjugates. The conjugates of the cocktail may comprise different peptides, which peptides may be cross-reactive with the high affinity/avidity antibodies. For example, the MN peptide (KRIHIGPGRAFYT) (SEQ ID NO:1) may be used to immunize subjects. The antibodies produced by the immunized subjects are cross-reactive in humans with other peptides, such as (GPGRAF)(SEQ ID NO:16)3, IYIG-PGRAC (SEQ ID NO:2), IAIGPGRAC (SEQ ID NO:3), IHIGPGRAC (SEQ ID NO:4), RSIHIGPGRAFYA (SEQ ID NO:6), KSITKGPGRVIYA (SEQ ID NO:7), KGIAIG-PGRTLYA (SEQ ID NO:8) and SRVTLGPGRVWYT (SEQ ID NO:9). This is shown in Table 18 below. Table 18 shows the ability of sera from volunteers immunized with 3 doses of MN-PND-PPD to recognize heterologous V3 loop PND peptides. OD represents the optical density obtained in ELISA plates coated with a specific PND-peptide of the V3 loop. It should be noted that vaccine No. 3 demonstrated a reactivity to 3 peptides (peptide Nos. 354, 355 and 358) at 1:20 serum dilution. Vaccine No. 7 demonstrated a broader reactivity at serum dilutions 1:20 and 1:100 (to peptide Nos. 282, 285, 354, 355 and 358).

TABLE 18

Cross-Reactive Antibodies In Humans

| | DILUTION | 282-(GPGRAF)3 | 283-IYIGPGRAC | 284-IAIGPGRAC | 285-IHIGPGRAC | 354-RSIHIGPGRAFYA |
| --- | --- | --- | --- | --- | --- | --- |
| CONTROL | 1:20 | 0.139 | 0.126 | 0.119 | 0.253 | 0.083 |
| #3 | 1:20 | 0.158 | 0.087 | 0.117 | 0.103 | 0.799 |
| | 1:100 | 0.057 | 0.036 | 0.041 | 0.055 | 0.172 |
| | 1:200 | 0.035 | 0.026 | 0.032 | 0.047 | 0.119 |
| | 1:500 | 0.026 | 0.022 | 0.024 | 0.028 | 0.159 |
| #4 | 1:20 | 0.105 | 0.069 | 0.123 | 0.129 | 0.940 |
| | 1:100 | 0.037 | 0.028 | 0.036 | 0.085 | 0.296 |
| | 1:200 | 0.029 | 0.021 | 0.028 | 0.025 | 0.151 |
| | 1:500 | 0.022 | 0.015 | 0.023 | 0.018 | 0.076 |
| #7 | 1:20 | 0.861 | 0.220 | 0.280 | 0.616 | 0.809 |
| | 1:100 | 0.234 | 0.065 | 0.095 | 0.144 | 0.380 |
| | 1:200 | 0.121 | 0.099 | 0.064 | 0.102 | 0.277 |
| | 1:500 | 0.048 | 0.027 | 0.036 | 0.058 | 0.117 |
| #9 | 1:20 | 0.218 | 0.141 | 0.470 | 0.425 | 1.574 |
| | 1:100 | 0.085 | 0.055 | 0.211 | 0.116 | 0.748 |
| | 1:200 | 0.052 | 0.039 | 0.165 | 0.078 | 0.571 |
| | 1:500 | 0.039 | 0.023 | 0.126 | 0.034 | 0.246 |
| #11 | 1:20 | 0.478 | 0.210 | 0.436 | 0.465 | 1.936 |
| | 1:100 | 0.099 | 0.060 | 0.129 | 0.145 | 0.838 |
| | 1:200 | 0.075 | 0.042 | 0.089 | 0.085 | 0.525 |
| | 1:500 | 0.046 | 0.028 | 0.063 | 0.058 | 0.365 |
| #17 | 1:20 | 0.266 | 0.257 | 0.312 | 0.242 | 2.106 |
| | 1:100 | 0.161 | 0.095 | 0.136 | 0.083 | 1.157 |
| | 1:200 | 0.178 | 0.059 | 0.080 | 0.043 | 0.640 |
| | 1:500 | 0.043 | 0.035 | 0.056 | 0.034 | 0.333 |
| #21 | 1:20 | 0.180 | 0.110 | 0.160 | 0.138 | 0.320 |
| | 1:100 | 0.056 | 0.032 | 0.069 | 0.066 | 0.081 |
| | 1:200 | 0.038 | 0.025 | 0.045 | 0.037 | 0.113 |
| | 1:500 | 0.102 | 0.020 | 0.034 | 0.025 | 0.129 |
| #24 | 1:20 | 0.199 | 0.134 | 0.208 | 0.168 | 0.493 |
| | 1:100 | 0.048 | 0.088 | 0.072 | 0.061 | 0.124 |
| | 1:200 | 0.040 | 0.099 | 0.046 | 0.039 | 0.058 |
| | 1:500 | 0.033 | 0.019 | 0.035 | 0.021 | 0.038 |

| | DILUTION | 355-KRIHIGPGRAFYT | 356-KSITKGPGRVIYA | 357-KGIAIGPGRTLYA | 358-SRVTLGPGRVWYT |
| --- | --- | --- | --- | --- | --- |
| CONTROL | 1:20 | 0.158 | 0.112 | 0.105 | 0.095 |
| #3 | 1:20 | 1.132 | 0.105 | 0.152 | 0.292 |
| | 1:100 | 0.335 | 0.035 | 0.047 | 0.051 |
| | 1:200 | 0.182 | 0.028 | 0.027 | 0.037 |
| | 1:500 | 0.083 | 0.017 | 0.018 | 0.028 |
| #4 | 1:20 | 1.159 | 0.062 | 0.078 | 0.095 |
| | 1:100 | 0.419 | 0.029 | 0.030 | 0.034 |
| | 1:200 | 0.241 | 0.023 | 0.022 | 0.024 |
| | 1:500 | 0.108 | 0.016 | 0.018 | 0.016 |
| #7 | 1:20 | 2.178 | 0.179 | 0.359 | 0.613 |
| | 1:100 | 1.368 | 0.084 | 0.106 | 0.218 |
| | 1:200 | 0.918 | 0.043 | 0.054 | 0.103 |
| | 1:500 | 0.399 | 0.023 | 0.032 | 0.053 |

TABLE 18-continued

Cross-Reactive Antibodies In Humans

| #9  | 1:20  | 2.181 | 0.103 | 0.145 | 0.222 |
|-----|-------|-------|-------|-------|-------|
|     | 1:100 | 1.239 | 0.055 | 0.050 | 0.066 |
|     | 1:200 | 0.798 | 0.037 | 0.039 | 0.051 |
|     | 1:500 | 0.356 | 0.025 | 0.027 | 0.029 |
| #11 | 1:20  | 2.231 | 0.368 | 0.794 | 0.472 |
|     | 1:100 | 1.549 | 0.093 | 0.163 | 0.111 |
|     | 1:200 | 0.982 | 0.067 | 0.087 | 0.075 |
|     | 1:500 | 0.445 | 0.041 | 0.057 | 0.047 |
| #17 | 1:20  | 0.434 | 0.428 | 0.380 | 0.343 |
|     | 1:100 | 0.127 | 0.123 | 0.091 | 0.081 |
|     | 1:200 | 0.072 | 0.082 | 0.066 | 0.069 |
|     | 1:500 | 0.058 | 0.057 | 0.040 | 0.043 |
| #21 | 1:20  | 0.593 | 0.116 | 0.173 | 0.114 |
|     | 1:100 | 0.167 | 0.037 | 0.038 | 0.039 |
|     | 1:200 | 0.089 | 0.030 | 0.040 | 0.030 |
|     | 1:500 | 0.060 | 0.028 | 0.023 | 0.019 |
| #24 | 1:20  | 0.108 | 0.175 | 0.155 | 0.155 |
|     | 1:100 | 0.014 | 0.055 | 0.048 | 0.053 |
|     | 1:200 | 0.011 | 0.035 | 0.033 | 0.039 |
|     | 1:500 | 0.011 | 0.026 | 0.022 | 0.024 |

TABLE 19

Percentage of inhibition on HIV-MN control after fourth immunization

| | | Serum Dilution | |
|---|---|---|---|
| PBS Media | 1:25 | 1:100 | 1:250 |
| HIV-MN Control | 48,510 | 50,360 | 46,380 |
| Control Serum | 22,800 | 20,190 | 24,360 |
| 1:100 3/5000 | 63,690 (31.8%) | 69,700 (38.4%) | 69,440 (49.7%) |
| 1:200 4/50 | 10,348 (78.7%) | 25,900 (48.6%) | 27,120 (41.6%) |
| >1:500 7/50 +282 | 896 (98.2%) | — | 79,860 (72.1%) |
| >1:500 9/50 +282 | 7,099 (85.4%) | 16,020 (68.2%) | 34,810 (25.05%) |
| >1:500 11/50 +282 | 1,808 (96.3%) | 8,137 (83.9%) | 8.708 (82.3%) |
| >1:500 17/50 −354 | 0.2 (99.0006%) | — | — |
| 1:100 21/5000 | 15,560 (68.0%) | 16,530 (67.2%) | 58,760 (26.6%) |
| 1:20 24/0 | 52,000 (7.1%) | 20,890 (58.6%) | 19,740 (57.5%) |

Percentage of inhibition on HIV-MN control

The subjects were immunized a fourth time with the PPD-MN-PPD conjugates. Table 19 shows the percentage of inhibition on HIV-MN control.

Table 20 shows the affinity of antibody before and after the booster (fourth) immunization with the conjugates. As shown in Table 20, the affinity after boosting increased dramatically.

TABLE 20

Affinity of antibody before and after boosting

| | MN-PND (μg/ml) | |
|---|---|---|
| Volunteer No. | Before* | After |
| 3 | >5000 | 5000 |
| 4 | 1000 | 50 |
| 7 | 500/1000 | 50 |
| 9 | 500/1000 | 50 |
| 11 | 500/1000 | 50 |
| 15 | 100/500 | |
| 17 | 50/500 | 5 |
| 18 | 50/500 | |

TABLE 20-continued

Affinity of antibody before and after boosting

| | MN-PND (μg/ml) | |
|---|---|---|
| Volunteer No. | Before* | After |
| 19 | 500/500 | |
| 20 | >5000 | |
| 21 | >5000 | 5000 |
| 24** | >5000/>5000 | >5000 |

*2 determinations
**PPD-negative

EXAMPLE X

Immunization of Humans with Conjugates of MN-PND Coupled to Carrier PPD

Subjects who were negative in a third generation HIV antibody ELISA assay were further screened for tuberculin (PPD) reactivity with 100 ml of 2 TU/PPD administered intradermally. For the 9 subjects who were negative to borderline PPD positive, a second skin test was performed with 10 TU/PPD. A total of 12 subjects were classified as PPD-positive at the 2 TU test dose.

Again, the vaccine administered was a conjugate of PPD and the MN-PND peptide. The MN-PND peptide sequence, KRIHIGPGRAFYT (SEQ ID NO:1), was prepared by standard solid phase synthesis and its composition was verified on an automated amino acid analyzer. The MN-PND peptide was conjugated to PPD in a Pilot GMP Laboratory by reacting PPD and MN-PND in a 2% glutaraldehyde solution (Fluka Chemicals, Buchs, Switzerland). After dialysis against sterile phosphate buffered saline, the solution was aseptically aliquoted at approximately 830 mg conjugate/ml. Given the heterogeneous nature of PPD, it was not possible to accurately determine the ratio of PPD to MN-PND in the conjugate by amino acid analysis. Therefore, incorporation of 125I MN-PND peptide into PPD in the presence of glutaraldehyde was determined for a representative pilot lot of 600,000 cpm/mg of 125I MN-PND.

Following conjugation with 2 mg of PPD (100 TU), 710,000 cpm were detected, which, assuming total recovery, corresponded to 0.645 mg MN-PND/mg of PPD. A human vaccine dose of 50 TU of PPD therefore contained approximately 0.645 mg of MN-PND. The molecular weight of the conjugate was approximately 15,000 kDa as determined by HPLC. Sterility and general safety tests were performed according to guidelines set forth by the European Pharmacopoeia. All lots of vaccine were found to be sterile and nontoxic.

In order to immunize, the following procedure was followed: a single dose, equal to 50 TU (1 mg) of PPD, contained approximately 0.645 mg of the MN-PND peptide in a volume of 100 ml. Subjects were immunized with 50–100 TU of PPD conjugate vaccine (0.645–1.29 mg of MN-PND) by the intradermal route into one or both inner forearms. A pilot experiment examining the immunogenicity of the MN-PND-PPD conjugate by immunizing five PPD positive volunteers with 2, 10, or 50 TU of vaccine conjugate on days 0, 60 and 90 indicated that antibody responses were only noted in the volunteers receiving 50 TU. In addition, pilot experiments indicated that 100 TU of MN-PND-PPD conjugate could be safely administered to PPD-negative subjects. Based on these results, 24 additional volunteers were immunized with either 50 TU for PPD positive volunteers of 100 TU for PPD negative individuals of the PPD conjugate vaccine on days 0, 14, 28, 82 and 383 (see Table 21, below). All vaccinees were monitored periodically for local and systemic reactions as well as by a standard battery of blood chemistries and complete blood counts. Local reactions were monitored within 1 hour, 24 hours and 72 hours of immunization. In cases of local itching, redness and swelling no topical treatment was administered. However, at the first sign of blistering, topical corticosteroids were prescribed.

TABLE 21

Immunization Schedule

| Vaccinee | PPD skin test Reactivity 2TU | 10TU | Immunization Intradermal dose # sites | Immunization # day I | II | III days | IV | V | adverse reaction (at immunization #) |
|---|---|---|---|---|---|---|---|---|---|
| 1 | − | − | nd | nd | nd | nd | nd | nd | drop out |
| 2 | − | − | 2 × 25TU | 0 | 14 | 28 | nd | nd | none |
| 3 | + | nd | 2 × 25TU | 0 | 14 | 28 | 82 | nd | none |
| 4 | + | nd | 2 × 25TU | 0 | 14 | 28 | 82 | 383 | none |
| 5 | − | − | 1 × 100TU | 0 | 14 | 28 | nd | nd | none |
| 6 | − | − | 1 × 100TU | 0 | 14 | 28 | nd | 383 | none |
| 7 | + | nd | 2 × 25TU | 0 | 14 | 28 | 82 | 383 | none |
| 8 | − | + | 2 × 25TU | 0 | 14 | 28 | nd | nd | none |
| 9 | + | nd | 2 × 25TU | 0 | 14 | 28 | 82 | nd | none |
| 10 | − | − | 2 × 25TU | 0 | 14 | 28 | nd | nd | none |
| 11 | + | nd | 2 × 25TU | 0 | 14 | 28 | 82 | 383 | blister (IV; V) |
| 12 | − | nd | nd | nd | nd | nd | nd | nd | drop out |
| 13 | − | − | 1 × 100TU | 0 | 14 | 28 | nd | 383 | none |
| 14 | − | − | 2 × 25TU | 0 | 14 | 28 | nd | 383 | none |
| 15 | + | nd | 2 × 25TU | 0 | 14 | 28 | 82 | 382 | low grade fever |
| 16 | − | − | 1 × 100TU | 0 | 14 | 28 | nd | 385 | none |
| 17 | + | nd | 2 × 25TU | 0 | 14 | 28 | 82 | 383 | low grade fever |
| 18 | + | nd | 2 × 25TU | 0 | 14 | 28 | 82 | nd | blister (I) |
| 19 | + | nd | 2 × 25TU | 0 | 14 | 28 | 82 | nd | blister (I; III) |
| 20 | + | nd | 2 × 25TU | 0 | 14 | 28 | 82 | nd | none |
| 21 | + | nd | 2 × 25TU | 0 | 14 | 28 | 82 | nd | none |
| 22 | − | + | 2 × 25TU | 0 | 14 | 28 | nd | nd | none |
| 23 | − | nd | 2 × 25TU | 0 | 14 | 28 | nd | nd | none |
| 24 | − | − | 2 × 25TU | 0 | 14 | 28 | 82 | nd | none |

Since preclinical studies have shown in guinea pigs that the PPD-MN-PND conjugate has induced strong antibody responses only in BCG primed, PPD skin test positive animals, the immune response in volunteers was stratified to those who were PPD positive and those who were PPD negative. After 3 immunizations, vaccine boosters were given exclusively to PPD skin test positive volunteers (see Table 21).

The presence of antibodies directed against MN-PND was measured as described above. 100 mg/well of a solution of MN-PND (5,000 ng/ml) in 100 mM $NaHCO_3$, pH 9.6, was incubated in 96-well flat-bottomed microtiter ELISA plates overnight (MN-PND titer plates). Following peptide coating, the plates were washed with PBS containing 0.05% Tween-20, and unbound sites were blocked with blocking buffer (PBS/0.55 casein/0.05% Tween-20/0.001% rhodamine). Serial dilutions of the sera to be tested were added to the wells at a 1:20 dilution in blocking buffer and incubated for 1 hour at 37° C. Unbound antibodies were washed away and then goat anti-human IgG conjugated to peroxidase was added, incubated for 1 hour at 37° C. and then washed. Substrate was added and absorbance at 405 nm was measured with an automated spectrophotometer (Titertek Multiscan, Flow Laboratories, McLean, Va.). Samples that gave an optical density (OD) value greater twice the background absorbance were considered seroreactive. The data is presented as the reciprocal titer of the highest serum dilution that was seroreactive.

High affinity antibodies were measured by an antigen-limited ELISA as has been described. Microtiter plates were coated overnight with 5000, 1000, 500, 100, 50, 10, 5, or 0 ng/ml of MN-PND (MN-PND affinity plates). Following peptide coating, the plates were processed as described above. The anti-MN-PND affinity was measured by incubating a 1:20 dilution of serum in the MN-PND titer plates and reactivity was determined as described above. Therefore, reactivity with lower antigen concentrations correlated with higher affinity antibody, and the affinity is reported as the lowest antigen concentration where reactivity was detected. The samples were coded and run with positive and negative controls.

It was determined that there was cross-reactivity of the generated antibody response, in addition to the classical MN-PND peptide used in the vaccine (KRIHIGPGRAFYT) (SEQ ID NO:1), 8 additional peptides representing different HIV-1 strains were synthesized. ELISA plates were coated with an optimal concentration of the peptide, as described above. The peptides used were: IYIGPGRAC (SEQ ID NO:2), IAIGPGRAC (SEQ ID NO:3), IHIGPGRAC (SEQ ID NO:4), a triple repeat of the $V_3$ loop cap sequence-GPGRAFGPGRAFGPGRAF (SEQ ID NO:5), the PND sequence of HIV-$1_{SC}$-RSIHIGPGRAFYA (SEQ ID NO:6), the PND sequence of HIV-$1_{RF}$-KSITKGPGRVIYA (SEQ ID NO:7), the PND sequence of HIV-$1_{NY-5}$-KGIAIGPGRTLYA (SEQ ID NO:8) and the PND sequence of HIV-$1_{CDC-42}$-SRVTLGPGRVYWYT (SEQ ID NO:9), Seroreactivity was determined as described above.

In order to determine whether salivary and serum antibodies were produced, total saliva was collected from two HIV-1 negative volunteers, from HIV positive volunteers, from HIV positive volunteers and from 4 vaccinees, utilizing the Orasure hypertonic sponge system (Epitope, Beaverton, Oreg., USA). This system has been used in the past for the detection of HIV-1 specific salivary IgA. Since the preservative in the Orasure vial appeared to partially denature the IgA, it was replaced by buffered saline (PBS) with 0.1 M sodium azide. Saliva was diluted 1:20 in blocking solution, and 1 ml were added to each well of MN-PND titer plates. After 1 hour of incubation the plates were washed with PBS containing 0.05% Tween-20, reacted with peroxidase conjugated anti-human IgA or to anti-human secretory component for one hour, washed, incubated with substrate and absorbance was measured as described above.

In order to perform neutralization assays the following procedure was followed: HIV-$1_{MN}$ strain obtained from the AIDS Reference and Reagent Program, passaged in H9 cells and the TCID$_{50}$ was determined as described. H9 HIV-$1_{MN}$ cells chronically infected with HIV-$1_{MN}$ were washed and passed into fresh RPMI containing FCS for 24 hours. Infected cells were separated from free viral particles by centrifugation at 1,000 RPM for 30 minutes at 4° C. The cell-free supernatant was aliquoted and stored at −70° C. The infectious titer of the virus was determined by incubation of serial one-to-ten dilutions of viral supernatant in 5 ml of growth media containing H9 cells ($10^6$/ml). After culturing the cells for 5 days, reverse transcriptase activity of the supernatant was determined. The highest dilution of the virus stock that infected half of the quadruplicate cultures of H9 cells as determined by assessment of the supernatant for p24 antigen content using a commercial kit (DuPont, Wilmington, Del.) was defined as on TCID$_{50}$. Following heat-inactivation, the serum to be tested for neutralizing activity was incubated at the indicated dilution with $10^2$ to $10^3$ TCID$_{50}$ of HIV-$1_{MN}$ for 1 hour at 37° C. and then cultured with H9 cells. Following 18 days of culture, the concentration of P24 antigen in an aliquot of supernatant was measured using an antigen capture assay (DuPont, Wilmington, Del.). In addition, the presence of syncytia was sorted by microscopic assessment.

The proliferative response of PBMC from vaccinated volunteers was assessed. Peripheral blood mononuclear cells (PBMC) were separated on Ficoll gradients, resuspended in RPMI culture medium with 10% human AB serum and $10^5$ cells in 100 ml culture medium were placed in each well of 96 well flat-bottomed microtiter plates and incubated with and without the MN-PND peptide (1 mg/ml). After 5 days of culture, proliferative responses were assessed by determining the incorporation of $^3$H-thymidine added during the last 16 hours of culture.

The presence of MN-PND-specific CTL was then determined. Principally, EBV-transformed autologous B cells were incubated with vaccinia vectors (VPE 16-HIV-1 gp160-IIIB and v PEMS-HIV-1/gp160-MN) for 90 minutes at 37° C. Cells were then washed and transferred to a 24-well culture plate for overnight incubation at 37° C. Subsequently, target cells were labelled with $^{51}$Cr and after three washes were resuspended in RPMI with 10% FCS at $5 \times 10^4$ viable cells per well. The subjects' effector PBMC were suspended at $2 \times 10^6$ viable cells per ml and reacted with magnetic microspheres (Dynabeads, Advanced Magnetics, Boston, Mass.) coated with monoclonal antibodies to CD4. After 45 minutes incubation at 5° C. the tube was placed on the capture magnet. The cell suspension not bound by the magnet was resuspended to $5 \times 10^6$ cells per ml in RPMI+ 10%/FCS. 100 ml of each effector cell population was added to triplicate wells of the target cells and $^{51}$CR release was measured. Spontaneous release controls as well as maximal release with 0.5% Triton X-100 were run simultaneously.

Due to the development of adverse responses to the vaccine, two subjects, #1 and #12, dropped out of the study prior to receiving the first vaccine dose. Reactions following each dose of vaccine are detailed in Table 21. Typical reactions were local redness and induration after 24–48 hours. Severe local reactions were not observed. Small painless blisters which resolved without scarring occurred in vaccine subjects #11, #18 and #19. In vaccine subject #18 the blister appeared only in the first of 4 immunizations, and in vaccine subject #11 a blister was noted only after the 3rd but not after the 4th immunization. In the other vaccine subjects, the skin reactions did not increase with subsequent doses. Two vaccine subjects, #15 and #17, experienced low grade fever one day after an immunization but not after another boost.

Antibody responses to MN-PND were determined. In a pilot study using five PPD+ subjects, only one subject receiving the highest vaccine dose (50 TU=0.65 mg PND) had an antibody response which increased after the second and third dose. These antibodies were of high affinity. The same subject's PBMC responded in vitro by proliferation and secretion. of IL-2 upon exposure to MN-PND. Subsequently all PPD+ subjects received the 50 TU PPD-MN-PND dose (0.65 mg PND) whereas some of the PPD negative subjects received up to 100 TU-PPD-MN-PND. None of the PPD negative subjects had any antibody response to the PND. In all 12 PPD positive vaccine subjects reciprocal antibody titers ranging between 1:100 and 1:2, 000 were detected. The majority of vaccine subjects had a titer of 1/500 or above (see Table 22, below). Although vaccine subject #23 had the lowest antibody titer, these antibodies were of high affinity (see Table 22).

TABLE 22

Reciprocal antibody titer, and affinity to MN-PND

| VACCINEE # | 0 | 14* | 28* | 42 | 82 | 98 | 131 | 169 | 179 | 251 | 383 | 392 | 449 |
|---|---|---|---|---|---|---|---|---|---|---|---|---|---|
| 3 | —+ | <1/20+ | >1/20+ | 1/20 | 1/20 (5000)+ | | 1/100 (5) | | | | 1/50 (100) | (100) | 1/50 (100) |
| 4 | —+ | <1/20+ | —+ | 1/20 (500) | 1/20 (500)+ | | 1/200 (50) | | | | 1/50 (100)+ | | 1/50 (100) |
| 7 | —+ | <1/20+ | >1/20+ | 1/200 (250) | 1/500 (500)+ | | 1/1000 (10) | | | | 1/500 (5)+ | 1/200 (50) | 1/20 (100) |
| 9 | —+ | 1/20+ | >1/20+ | 1/200 (250) | 1/20 (500)+ | | 1/1000 (50) | | | | | | |
| 11 | —+ | <1/20+ | >1/20+ | 1/200 (100) | 1/200+ | | 1/1000 (10) | | | | >1/50 (10)+ | nd (100) | |
| 15 | —+ | <1/20+ | >1/20+ | 1/200 (100) | 1/100 (500)+ | | | | 1/500 (10) | | 1/500 (10)+ | 1/200 (10) | 1/200 (5) |
| 17 | —+ | <1/20+ | >1/20+ | 1/200 (50) | 1/200 (500)+ | | 1/2000 5 | | | | 1/500 (10)+ | 1/500 (10) | 1/500 (10) |
| 18 | —+ | <1/20+ | >1/20+ | 1/200 (50) | 1/200 (500)+ | | | | 1/1000 (5) | 1/500 (5) | | | |
| 19 | —+ | <1/20+ | >1/20+ | 1/200 (100) | 1/100 (500)+ | | | | | | | | |
| 20 | —+ | <1/20+ | nd+ | nd | 1/100 (5000)+ | | | | <1/20 (5000) | 1/20 (5000) | | | |
| 21 | —+ | <1/20+ | nd+ | <1/20 | 1/20 (5000)+ | | >1/20 0 (50) | | | >1/100 (50) | | | |
| 23 | —+ | <1/20+ | <1/20+ | <1/20 | nd+ | | | 1/100 (50) | | 1/100 (50) | | | |

Figure 4A:
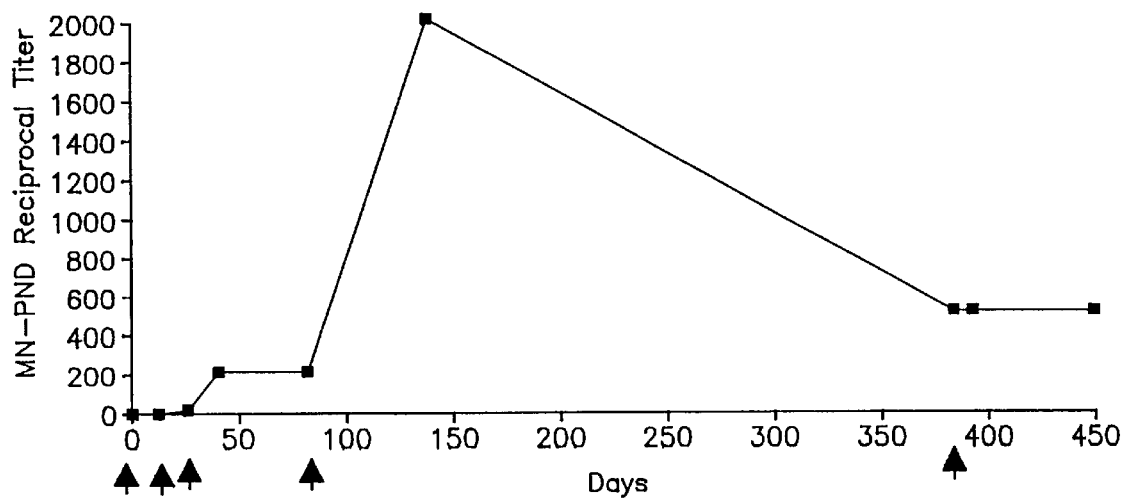
FIGS. 4A and 4B represent reciprocal antibody titers, measured by PND ELISA (FIG. 4A) and affinity of antibodies as measured by the antigen-limited ELISA (FIG. 4B). Reactivities with PND coating of the ELISA wells with 100 mg or less were considered high affinity/high avidity.
Figure 4B:
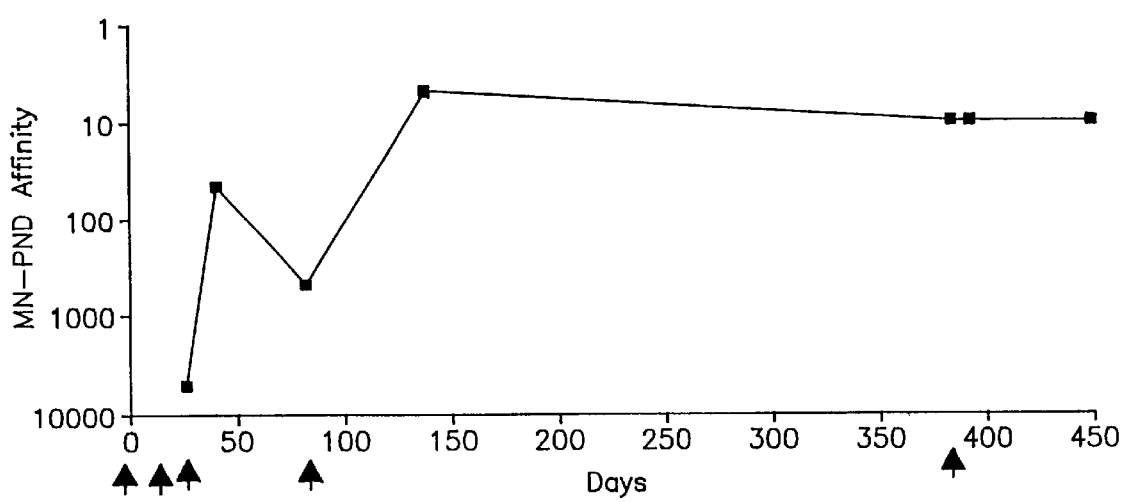

\* — only 1/20 serum dilution was used
+ — immunization
nd — not done
( ) — affinity ng PND/well Next, the affinity of anti-PND serum antibodies was determined. Any reactivity with wells coated with 100 mg/ml or less of MN-PND in the ELISA plates was considered as high affinity. No high affinity antibodies could be detected in any vaccinee until after the third boost (see Table 22 and FIG. 4). High affinity antibodies persisted thereafter for up to 367 days (see Table 22 and Table 23, below). There was a further increase in affinity/avidity to the highest measurable level in subjects #7, #15 and #17. The time course of the antibody titers and affinities for a representative volunteers, #17, is presented in FIG. 4.

TABLE 23

Persistance of Antibody Titer and High Affinity Antibodies To the MN-PND, Days After 2nd, 3rd and 4th Boost

| | DAYS AFTER BOOST | | |
|---|---|---|---|
| Vaccinee # | boost 2 | boost 3 | boost 4 |
| 3 | >54* | 367 | >66 |
| 4 | >54* | 301 | >66 |
| 7 | >54* | 301 | >66 |
| 9 | >54* | >49 | not done |
| 11 | >54* | 301 | not done |
| 15 | >54* | 301 | >66 |
| 17 | >54* | 301 | >66 |
| 18 | >54* | >169 | not done |
| 19 | >54* | not done | not done |
| 20 | none | >169 | not done |
| 21 | none | >169 | not done |
| 23 | none | >223 | not done |

*low affinity antibodies

Figure 5:
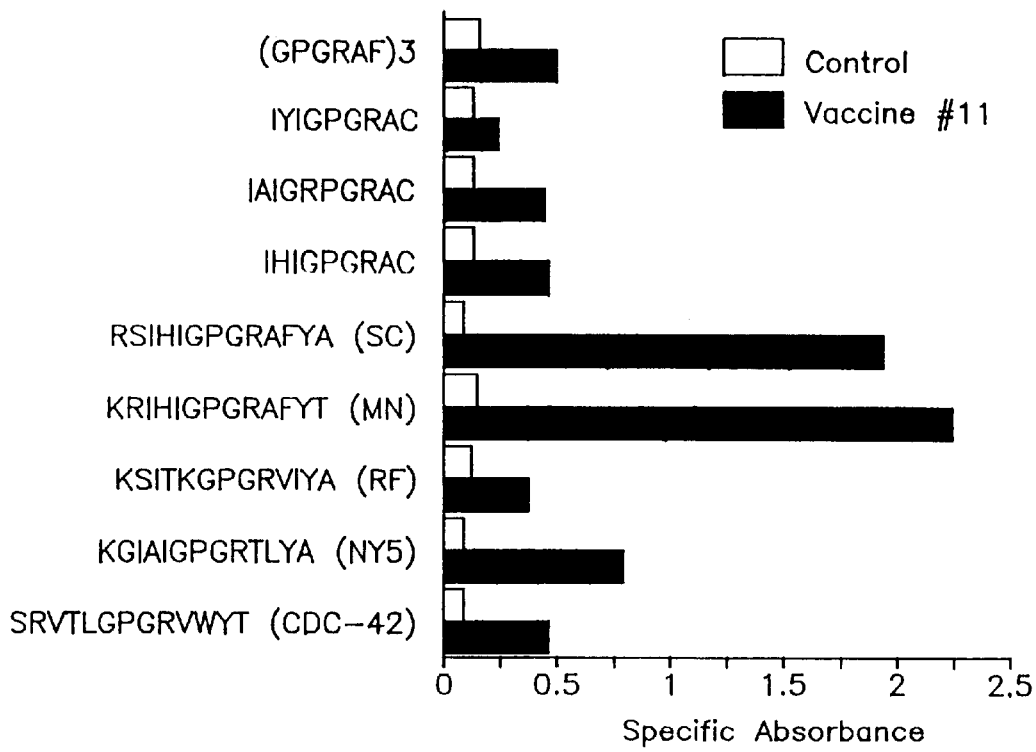
FIG. 5 represents the cross-reactivity of serum antibodies from vaccine subject #17 with MN-PND, with heterologous PND peptides and with the GPGRAF motif. Specific absorbance was measured in ELISA plates in which wells were coated with the respective peptide. The open bars represent the control, and the shaded bars represent the subject.

Cross-reactivity of serum antibodies was determined. It was found that there was strong recognition of peptides from HIV-1$_{SC}$ (FIG. 5) which shares the internal IHIGPGRAFY (SEQ ID NO:15) sequence with the MN strains. Reactivity against other peptides such as RF:NY-5,CDC-42 was also detectable. The cross-reactivity did increase after the fourth boost (not shown). PPD-negative volunteer ™21 exhibited borderline reactivity with MN with some cross-reactivity to SC.

Figure 6:
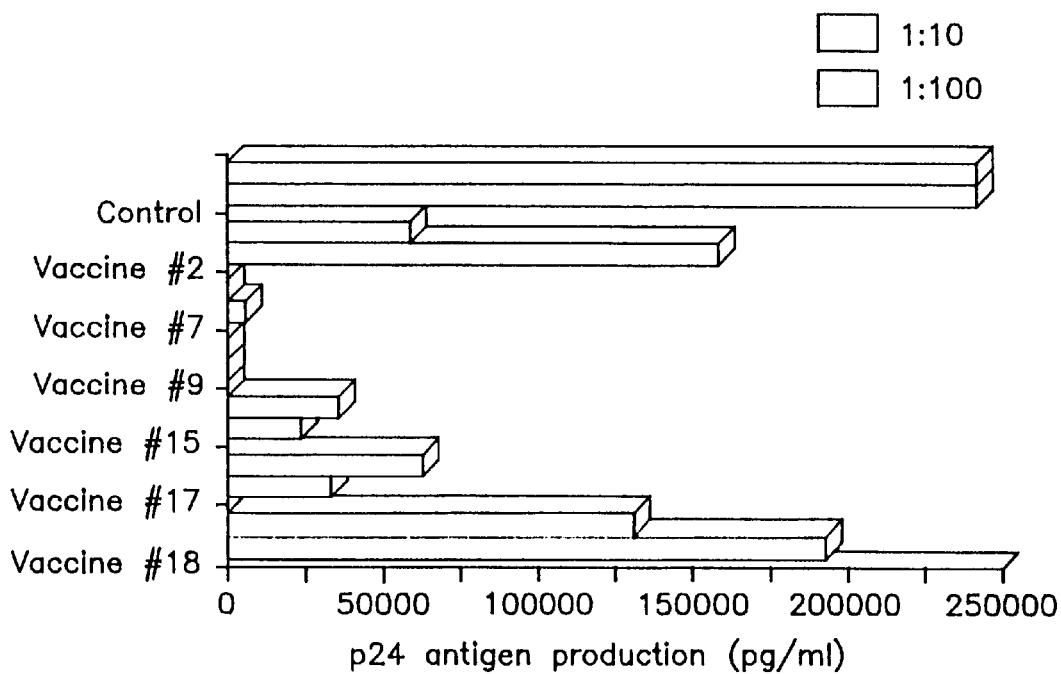
FIG. 6 represents the neutralization of HIV-1$_{MN}$ by serum from PPD-MN-PND immunized subjects as compared to normal human serum. Sera were diluted at 1:10 and 1:100 before incubation with HIV-1$_{MN}$. P24 levels were measured in supernatants of cultured HIV-1$_{MN}$ infected H9 cells.

Virus neutralization was then determined. None of the sera from PPD negative volunteers neutralized HIV-1$_{MN}$ (not shown). The ability of sera from PPD positive immunized subjects (after the 3rd boost) to neutralize the MN strain of HIV-1 is shown in FIG. 6. Sera from 10 of 11 subjects showed neutralizing activity at dilutions of up to 1:200 (subjects #4, #9 and #11) and at 1:100 (subjects #4, #7, #9, #11, #15, #17, #18 and #21). In two subjects (#7 and #9) there was a >99% reduction of p24 in culture supernatants with sera diluted 1:100.

Figure 7:
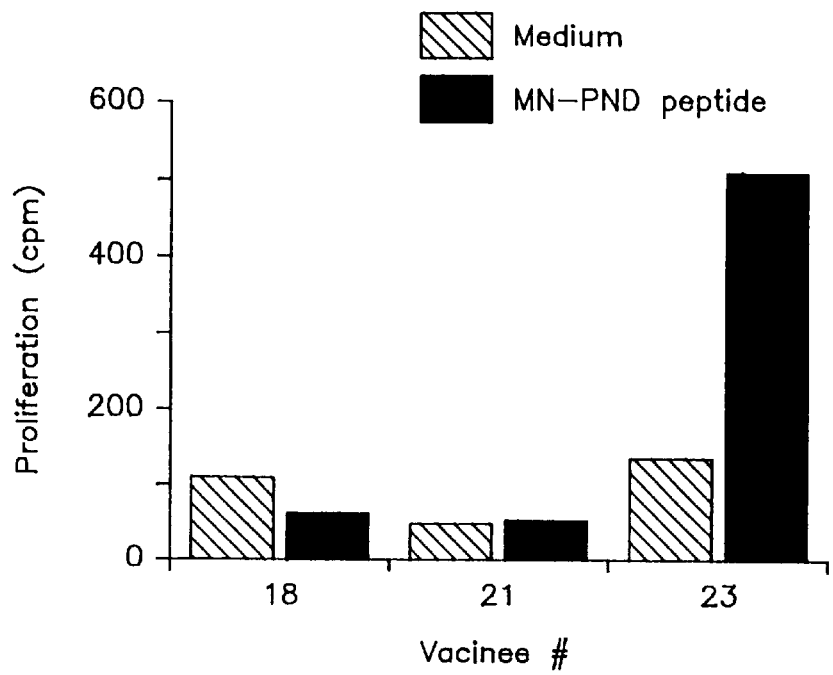
FIG. 7 represents proliferative responses to MN-PND. $10^5$ peripheral blood lymphocytes of vaccines were stimulated with 200 mg of PND for 7 days. Cellular proliferation was assessed by determining the incorporation of [$^3$H] thymidine added during the last 16 hours of culture.

Next, lymphocyte proliferative responses to MN-PND were determined. The proliferative responses to the MN-PND peptide were tested in 4 subjects (#18, #20, #21 and #23). Subject #23 exhibited a good in vitro proliferative response to the peptide after the 3rd boost (see FIG. 7).

Serum and salivary IgA were then determined. All PPD positive vaccine subjects who had an IgG response to the MN-PND also had specific IgA antibodies to MN-PND present in their serum. In some, serum IgA antibody titers were identical to serum IgG titers (see Table 24, below). In others the serum IgA titers were 1/2–1/25 of serum IgG titers. Volunteer #14, who did not mount a serum IgG response, had detectable serum IgA and low titer salivary IgA to the MN-PND. In 3 out of 4 tested unconcentrated saliva specimens, specific IgA antibodies to MN-PND were detectable at titers of up to 1/100 utilizing monoclonal antibodies to human IgA. In ELISAs utilizing a monoclonal antibody to bound SC no IgA was noted in unconcentrated saliva.

TABLE 24

Serum and Salivary IgA Antibodies to MN-PND

| | | | Serum | | | | Saliva | |
|---|---|---|---|---|---|---|---|---|
| | | | IgG | | IgA | | IgA | |
| vaccinee # | boost # | Days after boost | highest OD | titer | highest OD | titer | highest OD | tMwer |
| 3 | 3rd | 49 | 1.13 | 1/100 | 0.59 | 1/100 | | |
| 4 | 3rd | 55 | 1.16 | 1/200 | 0.75 | 1/200 | | |
| | 4th | 66 | 0.7 | 1/50 | 0.72 | 1/50 | 0.16 | — |
| 7 | 3rd | 49 | >2.0 | 1/1000 | 1.42 | 1/200 | | |
| | | 301 | 1.43 | 1/500 | 0.81 | 1/100 | | |
| | 4th | 66 | 1.41 | 1/100 | 1.05 | 1/100 | 0.33 | 1/50 |
| 9 | 3rd | 49 | >2.0 | 1/1000 | 1.2 | 1/500 | | |
| 11 | 3rd | 49 | 1.94 | 1/1000 | 0.71 | 1/100 | | |
| 14 | 4th | 66 | 0.06 | — | 0.69 | 1/50 | 0.27 | 1/20 |
| 15 | 3rd | 301 | 1.1 | 1/500 | 0.31 | 1/50 | | |
| 17 | 3rd | 55 | >2.0 | 1/1000 | 0.71 | 1/100 | | |
| | | 301 | 1.48 | 1/500 | 0.3 | 1/20 | | |
| | 4th | 66 | 0.95 | 1/100 | 0.55 | 1/20 | 0.69 | 1/100 |
| 18 | 3rd | 97 | 1.22 | 1/1000 | 1.48 | 1/100 | | |

Figure 8:
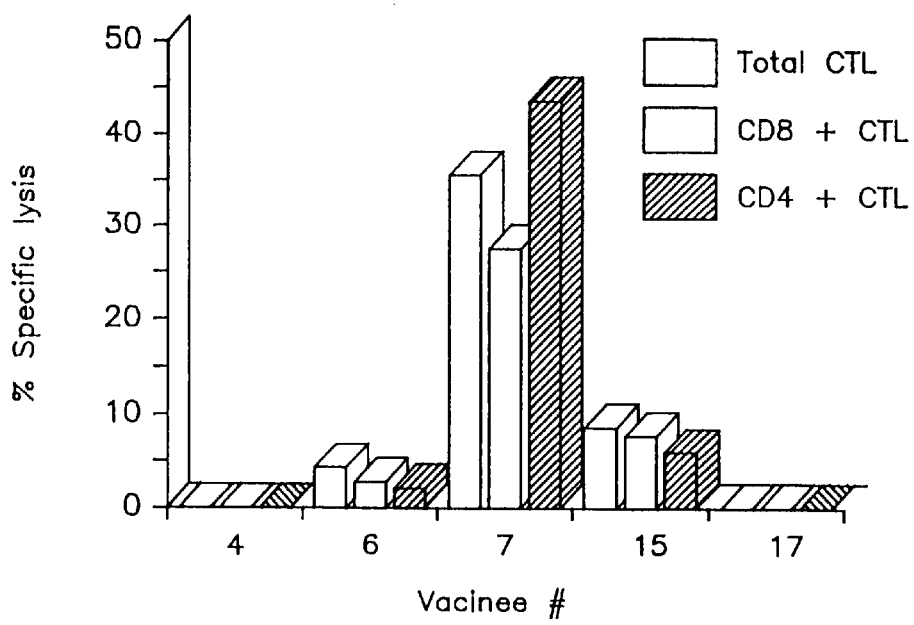
FIG. 8 represents CTL response as shown by percent of net specific lysis.
Figure 9A:
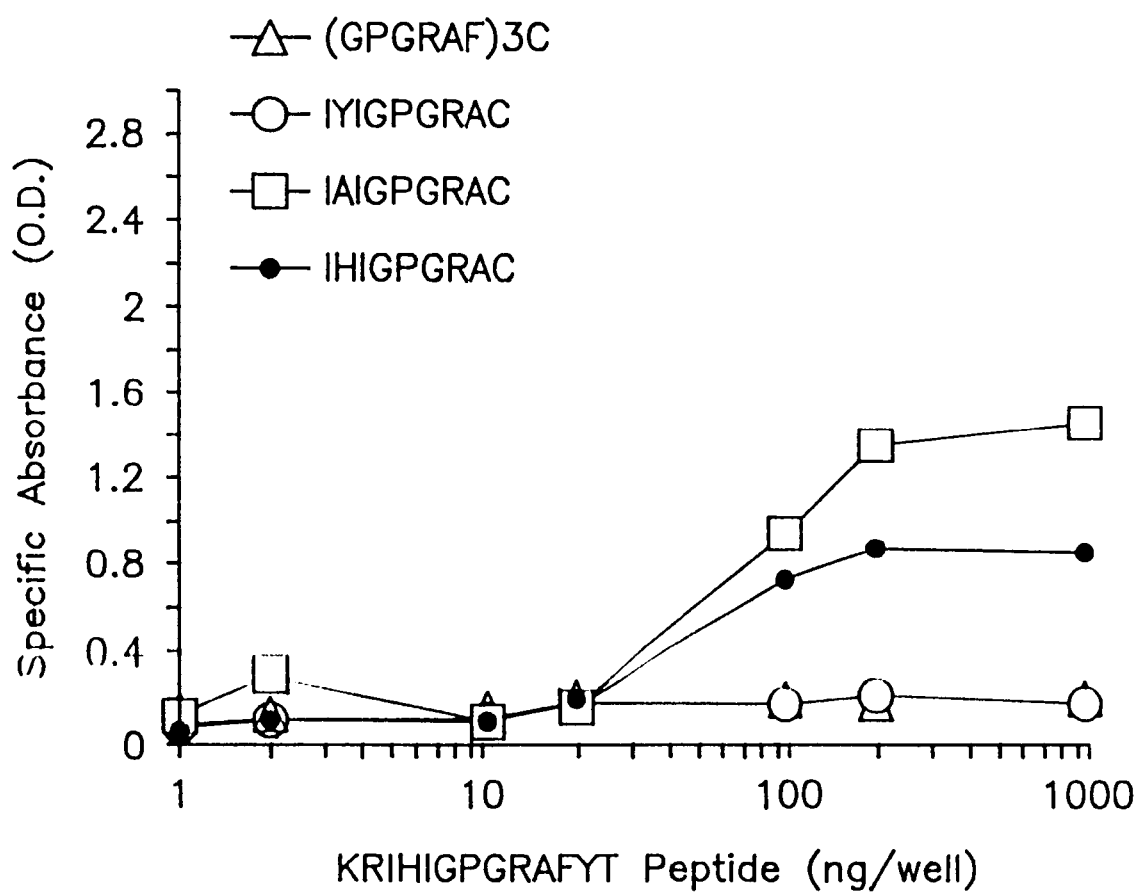
FIGS. 9A–9E represent the results of immunization of rabbits with various peptides coupled to KLH.
Figure 9B:
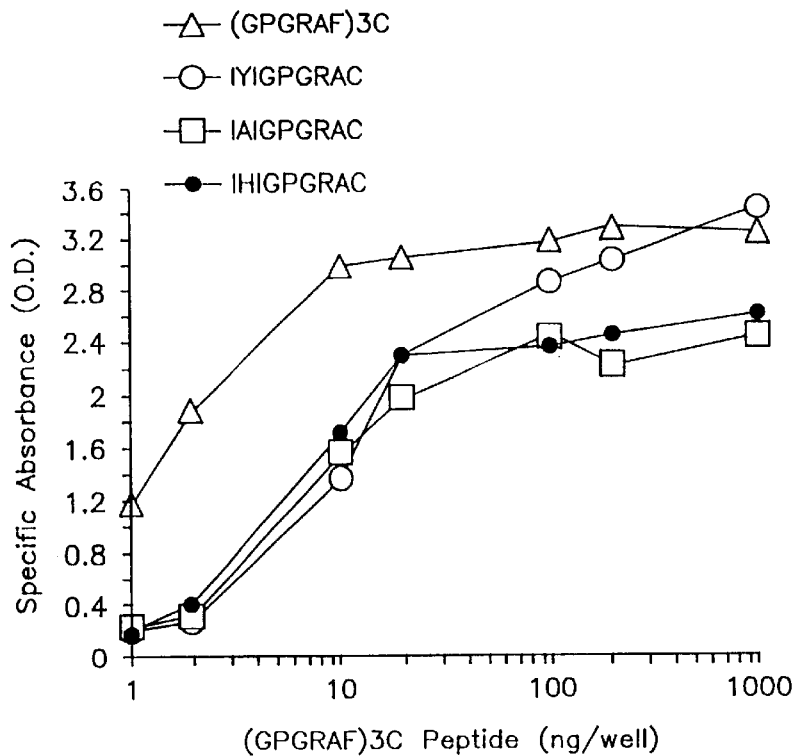
Figure 9C:
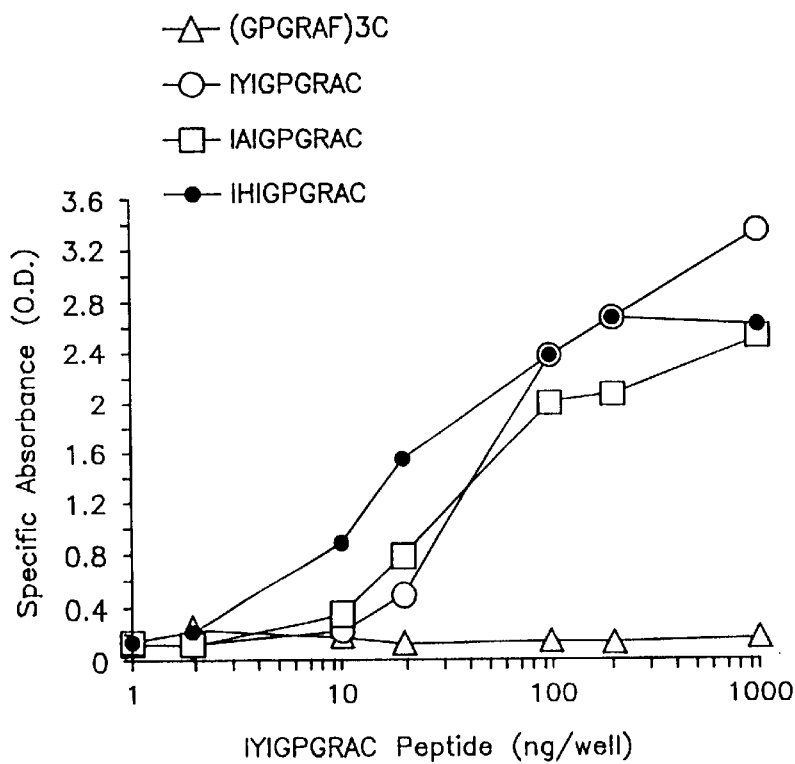
Figure 9D:
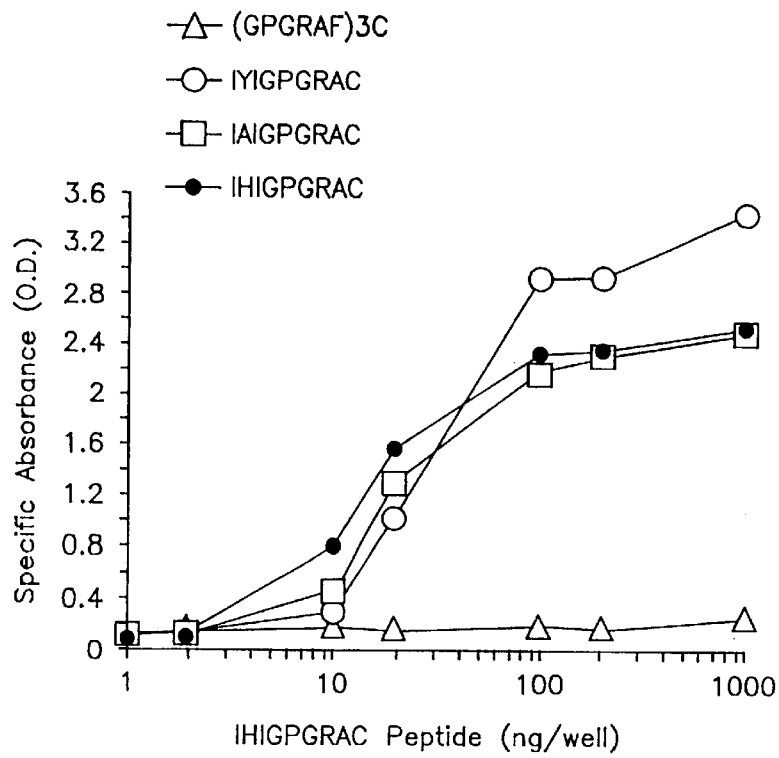
Figure 9E:
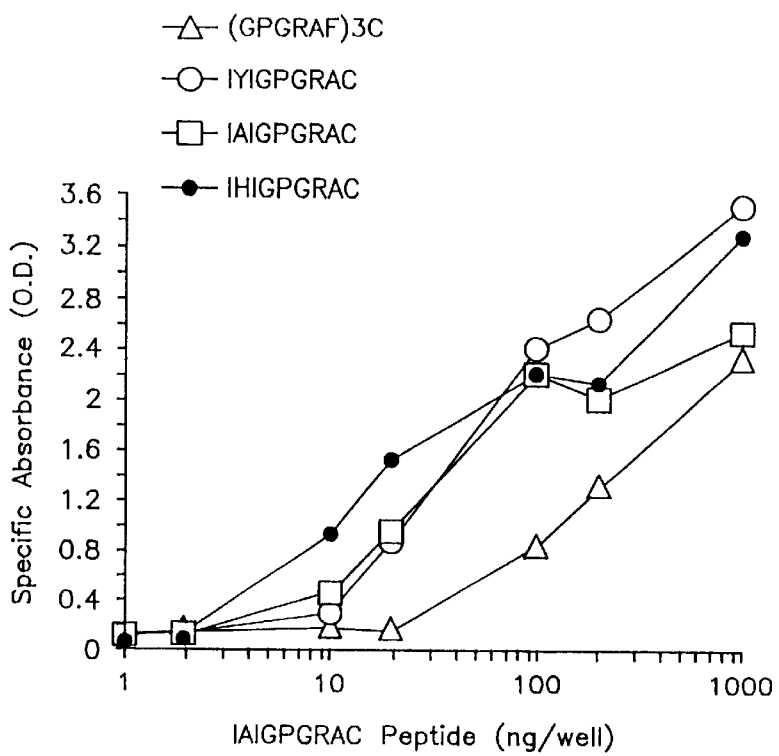
Figure 10A:
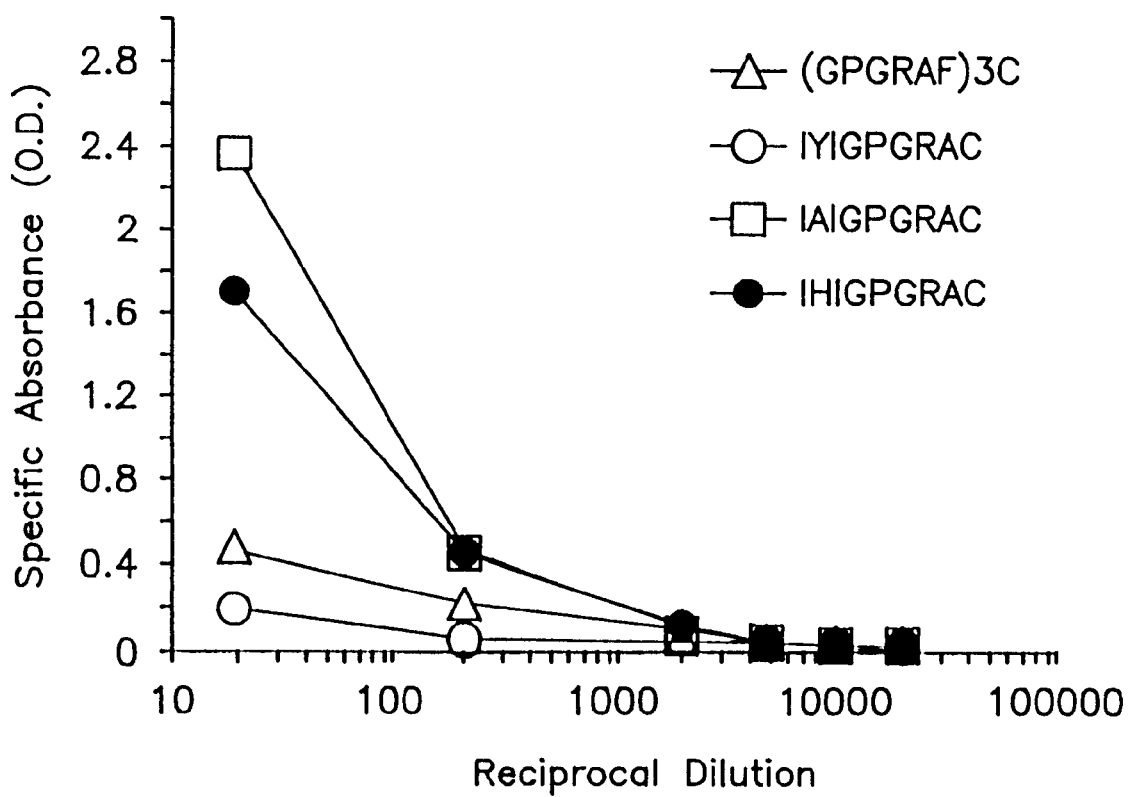
FIGS. 10A–10E represent the results of immunization of rabbits with various peptides coupled to KLH.
Figure 10B:
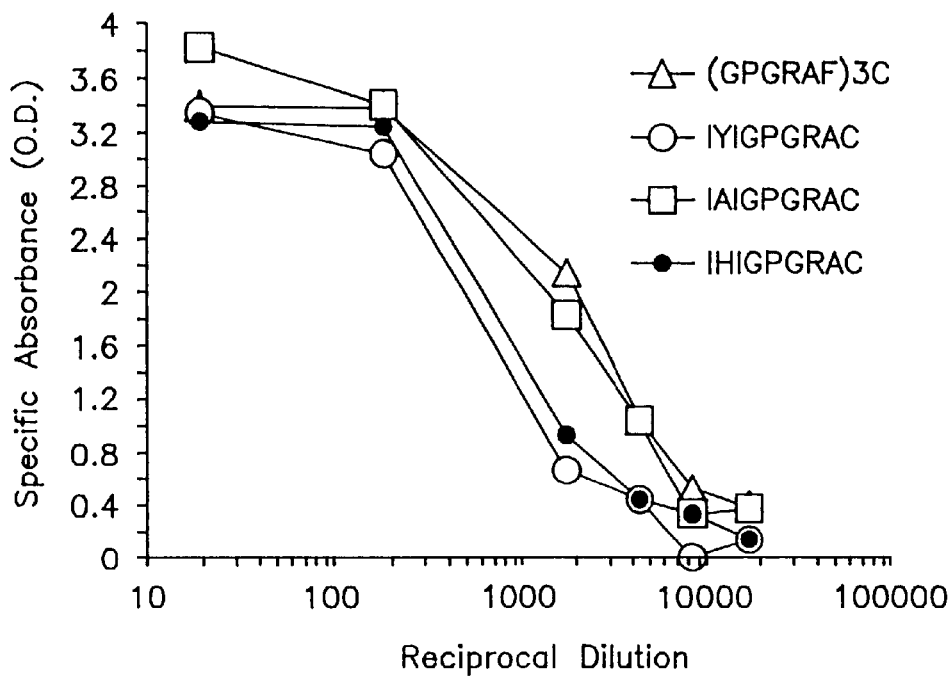
Figure 10C:
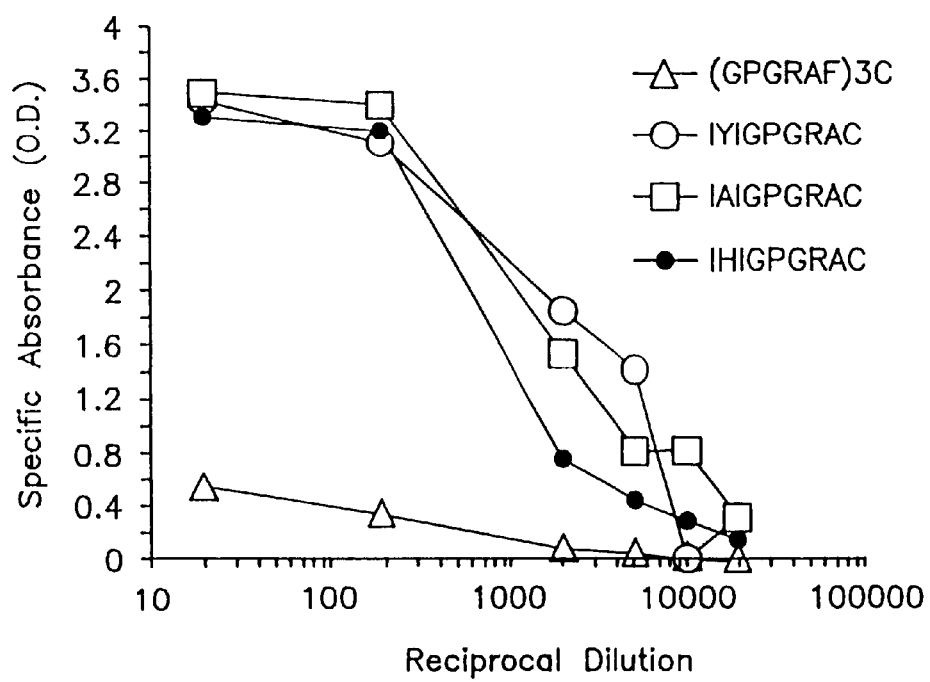
Figure 10D:
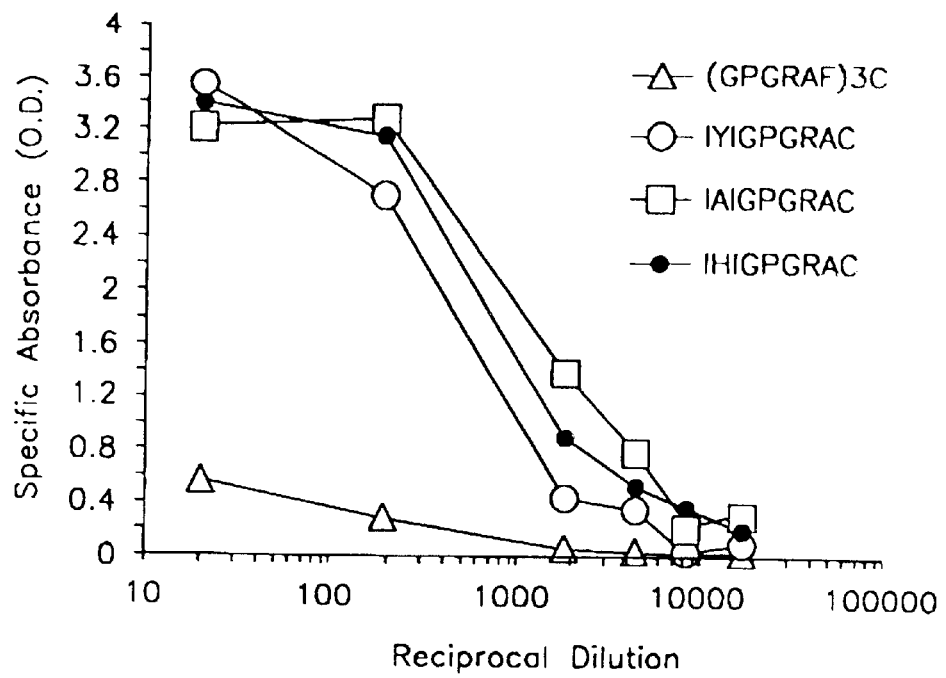
Figure 10E:
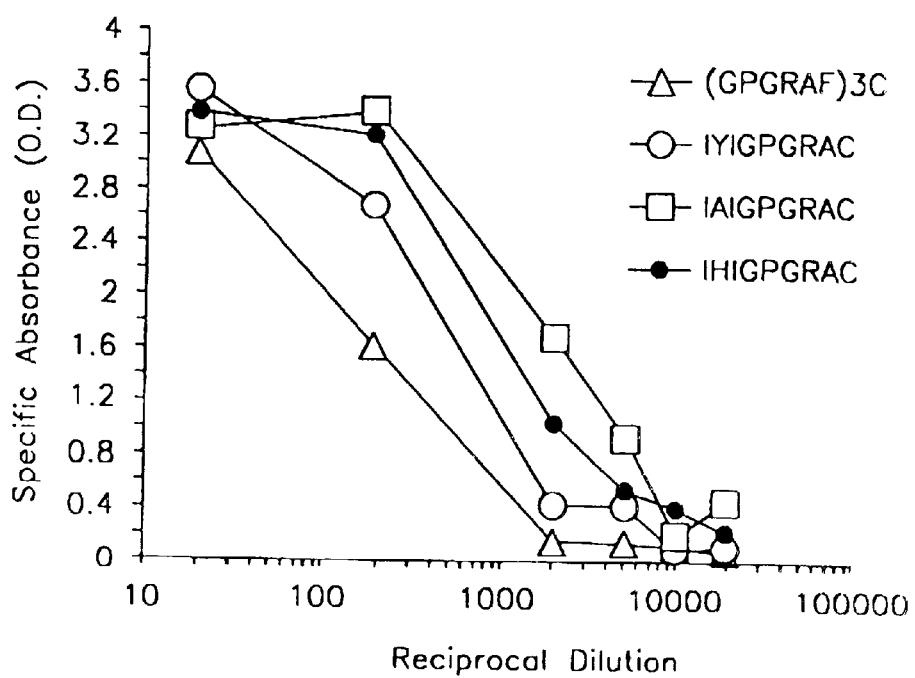

In studying CTL responses, three out of five vaccine subjects expressed specific lysis. The extent of lysis was variable (see FIG. 8). In the CTL responsive vaccine subjects, both CD8+ and CD4+ MN-PND peptide specific CTLs were noted. Vaccine subject #6 demonstrated primarily CD8 responses, while vaccine subjects #7 and #15 exhibited both CD4 and CD8 CTL responses.

Most immunogens that induce excellent cell-mediated immunity (CMI) as well as systemic and mucosal humoral immune responses are live attenuated vaccines. In fact, live attenuated simian immunodeficiency virus (SIV) protected rhesus monkeys from a challenge by wild-type pathogenic SIV. Live attenuated HIV vaccines are, however, unacceptable in humans for fear of reversion to virulence and induction of pathologic processes. The inventors have determined that an HIV-1 subunit (peptide) vaccine has induced in human subjects a broad range of immune responses nearing those of live-attenuated vaccines.

In order to develop a meaningful strategy for a preventive subunit AIDS vaccine there is a need for precise definition of the elements of protective immunity. In acute HIV-1 infection and in HIV-1 exposed but uninfected individuals, cytotoxic T lymphocytes (CTL) represent the first immune response elicited followed by antibodies to the HIV envelope. Other studies have also indicated that immune responses to the HIV envelope, and especially anti-$V_3$ loop primary neutralizing domain (PND) targeted antibodies, are pivotal for protection. Recombinant HIV envelope subunit vaccines have, therefore, received the greatest attention but have not been shown to induce potent and lasting immunity.

The vaccines of the invention produced persistent lymphoproliferative responses to a variety of HIV antigens preceding the induction of neutralizing antibodies. Consistent and broad immune responses were achieved only with the high dose regimen (300 mg/dose) and after the 3rd immunization with the HIV-1$_{IIIB}$ rgp120 vaccine in alum adjuvant. The safety of high dose vaccines has, however, been questioned for fear of activation of virus replication and induction of non-protective immunity. It has, for example, been demonstrated that a large intrarectal innoculum of SIV to macaques resulted in infection and antibody production with minimal CMI, whereas administration of lower doses elicited strong CMI with no antibody production and no detectable infection. In addition Bretscher et al. have shown that mice injected with a high dose of inactivated HIV exhibited a transient CMI response followed by antibody response, whereas lower doses generated a persistent CMI response. The inventors have shown that minute doses of PPD-MN-PND administered intradermally in the absence of adjuvants can induce protective immune responses. The vaccines of the invention, at a dose of 0.65 mg, induced a consistent, potent, and long lasting humoral and cellular immune response in PPD DTHR positive HIV-1 uninfected volunteers.

The unique potency of this vaccine may be attributed to both the intradermal route of immunization and to the use of PPD as a carrier. PPD is a unique immunologic reagent in that virtually everyone in the world with a functional immune response who has been exposed to BCG or *M. tuberculosis* infection will give a T-cell mediated DTHR to minute amounts of PPD. One explanation for its universal T-cell recognition is that PPD is made from cultures of autolyzed bacteria and may contain a mixture of degraded an "preprocessed" antigens that can be presented by all MHC Class II hapotypes. Studies indicate that mice presensitized by BCG can produce high levels of antibodies to peptides or even to carbohydrate epitopes if they are conjugated to PPD. PPD itself is nonimmunogenic, thereby avoiding the potential of carrier epitopic suppression. PPD is also widely used as a human diagnostic reagent with an extensive safety data base with hardly any adverse effects except for local reactions that resolve without scarring spontaneously or after topical corticosteroids. Worldwide, billions of people are PPD DTHR positive.

Immunization with BCG is also widely practiced in developing areas of the world where AIDS is prevalent, giving rise to a multi-billion primed population. Because of the reemergence of tuberculosis and more recently of multiple drug-resistant tuberculosis, consideration is now being given in Europe and the U.S. to BCG vaccinate clinically-stable HIV infected patients and their household contacts. It is therefore beneficial to administer BCG to prospective vaccine subjects who are PPD DHTR negative.

The antibody responses encountered in the PPD-MN-PND vaccine subjects were uniform and at higher titers than in any previously reported vaccine. Also of importance is the observation that the immune response achieved was broad. Infected individuals usually have a swarm of HIV-1 variants, and mutation rates are estimated at up to 1% per year. Restricted and narrow spectrum antibody response may therefore promote the emergence of neutralization resistant strans. Such mutations have been observed also in the $V_3$ region. Fortunately, a few sequence motifs of the $V_3$ account for over 50% of all isolates analyzed. The variation in the PND is therefore not insurmountable in the presence of highly cross-reactive, high affinity antibodies.

The antibodies generated by a low dose of the PND vaccine of the invention were of the highest affinity, were cross-reactive, were HIV-$1_{MN}$ neutralizing and were syncytium inhibiting. Sera from immunized subjects recognized PND peptides from the homologous MN and from other $V_3$ PND peptides. There was extensive recognition of peptides from HIV-1 SC and to a lesser extent of RF; NY5 and CDC-42. These antibody responses exceeded those of the recombinant gp120 vaccine with which only the high dose (300 mg) elicited neutralizing and cross-reactive antibodies. Another advantage of the peptide vaccines of the invention is that additional peptides can be conjugated to PPD, rapidly, inexpensively and according to the emergence of new PND variants in certain geographic areas.

Ideally, a vaccine should induce both salutary antibody responses and cell-mediated immunity. Cell mediated immunity is usually broader and may abrogate more easily the problem of mutations. To date, all subunit immunogens tested in animals and in humans induced antibodies that lasted at best only for several months after boosting, CMI induced was feeble, and dose response was less pronounced for the generation of memory T cells as expressed by in vitro assays of antigen specific lymphocyte proliferation. (The latter response was present early and was sustained for at least 4 months only after the third vaccine injection.) In contrast, with the PPD-MN-PPD vaccine of the invention not only do high-affinity, neutralizing antibodies persist for well over 1 year, but also long lasting CMI is induced as expressed by generation of antigen specific lymphoproliferation and induction of specific $CD8^+$ and $CD4^+$ cytotoxic T lymphocytes (CTL).

Protective HIV vaccines should also induce mucosal immunity in the genital tract in order to intercept the infectious virus at the most frequent route of transmission. Although systemic immunization strategies have protected macaques from intravenous challenge with SIV, they have not prevented vaginal transmission. Administration-of inactivated whole SIV or synthetic peptides by the mucosal route also did not induce an effective immune response. There have been no reports of HIV-1 candidate vaccines which induce mucosal immunity in humans. Prior to immunization with an HIV-1 gp160 subunit or any other parenteral vaccine has been inadequate to stimulate mucosal immunity. In contrast, the PPD-PND vaccine of the invention has induced high titer specific anti-PND serum IgA and mucosal IgA antibodies.

EXAMPLE XI
Immunization of Guinea Pigs with Conjugates of MN-PND Coupled to the Carriers PPD Alone, Toxin A Alone, PPD with Toxin A, and PPD With Both Toxin A and the Adjuvant $Al(OH)_3$ In order to produce the toxin A-PND vaccine, a total of 5.8 ml (30.9 mg) of toxin A-ADH was added to a sterile 10 ml vial containing a magnetic stirrer. The pH was adjusted to 5.6 by the addition of 188 ml of HCl using an automated titrater. To this solution 62 mg of solid EDEC was added over a 6 minute period of time (dropwise). The pH dropped to 4.98. The reaction was allowed to proceed at ambient temperature for 1 hour with gentle stirring and the pH was maintained at 4.95–5.1. An additional 31 mg of solid EDEC were added and the reaction was allowed to proceed for an additional 2.5 hours. The pH rapidly stabilized and pH titration was not required. At the end of this period, the pH was 4.975. The solution was aseptically withdrawn into a sterile syringe and applied onto a 5×56 cm Sephadex G-75 column equilibrated in sterile PBS, pH 7.4. The elution profile was monitored at 206 and 276 nm and 8.1 ml fractions collected. Fractions 35–57 (void volume fractions with a high absorbance) were collected and pooled. The pool was found to contain 155 mg protein per ml by the Lowry assay.

Next, guinea pigs, some of which were previously primed with BCG and some of which were not, were immunized on days 0 and 14 with (a) the peptide MN (KRIHIGPGRAFYT) (SEQ ID NO:1) conjugated with the carrier PPD alone (Groups 1–3 and 5); (b) the MN peptide conjugated with the carrier toxin A either alone or in conjunction with the carrier PPD (Groups 6–9 and 14); (c) the MN peptide conjugated with both carriers PPD and toxin A, along with the adjuvant $Al(OH)_3$ (Groups 12 and 13); (d) the MN peptide unconjugated with PPD (Group 4); and (e) the MN peptide unconjugated with toxin A and PPD (Groups 10 and 11). The results are summarized in Table 25 below. Vaccines containing the peptide coupled to toxin A (Groups 6, 8, 9, 11 and 13) had significantly higher immune responses than the peptide coupled to PPD (Groups 1, 2, 3 and 5). Immune response was further increased by adding PPD to the peptide-toxin A conjugate (Group 11). In addition, adsorption of the adjuvant $Al(OH)_3$ to the peptide-toxin A-PPD conjugate further increased immune response (Groups 12 and 13). See Table 25. Hence, the vaccines of this invention are able to elicit an immune response to MN HIV, and are therefore useful in the treatment and transmission prevention of HIV.

TABLE 25

Anti-PND Antibody Response in Guinea Pigs

| Group | Vaccine | Priming | GKT (Range) |
|---|---|---|---|
| 1 | PPD-PND (Lot 1) (1 mg) | Yes | 8.3 (3.9–35.4) |
|   |  | No | 2.1 (1.7–2.8) |
| 2 | PPD-PND (Lot 2) (1 mg) | Yes | 1.65 (0.9–2.8) |
| 3 | PPD-PND (Lot 3) (1 mg) | Yes | 1.49 (1–4.7) |
| 4 | PPD (50 IU) + PND (1 mg); unconjugated | Yes | 1.44 (0.9–2.4) |
| 5 | PPD-PND (Lot 1) (1 mg) | Yes | 2.38 (0.08–5.2) |
| 6 | PPD-PND (1 mg) + Toxin A-PND (10 mg) | yes | 201 (15.8–1300) |
| 7 | Toxin A-PND (1 mg) | Yes | 2.41 (0.8–7.9) |
| 8 | Toxin A-PND (10 mg) | Yes | 53.3 (8.3–393) |
| 9 | Toxin A-PND (10 mg) | No | 33.2 (5–333) |
| 10 | Toxin A-PND (1 mg) + PPD (50 IU); unconjugated | Yes | 3 (1.7–9.3) |
| 11 | Toxin A-PND (10 mg) + PPD (50 IU): unconjugated | Yes | 196 (55–1344) |
| 12 | Toxin A-PND (1 mg) + PPD (50) IU + $Al(OH)_3$ | Yes | 105 (18–1018) |
| 13 | Toxin A-PND (10 mg) + PPD (0 IU) + $Al(OH)_3$ | Yes | 912 (395–1374) |
| 14 | Toxin A-PND (1 mg) + PPD-PND (50 IU; 1 mg) | Yes | 17 (0.4–153) |

Table 26, below, shows reciprocal titers and affinity of antibodies in guinea pigs immunized with various vaccines of this invention. As demonstrated, some of the guinea pigs immunized with the vaccines of this invention produced high affinity antibodies to MN-HIV.

TABLE 26

Reciprocal titers and affinity of antibody in sera of guinea pigs

| BCG(-14d) | PND(MN)-PPD | PND(MN)-TA(ADH) | PND(MN) | PPD | GP # | Day 28 | After Boost-Day 56 | Day 28 | After Boost-Day 56 |
|---|---|---|---|---|---|---|---|---|---|
| " | 1 ug (Lot #1) | | | | 8428 | 100 | 1,000 | | 100 |
| " | " | | | | 8429 | 20 | 12,000 | | 50 |
| " | " | | | | 8430 | 20 | 4,000 | | 100 |
| " | " | | | | 8431 | 20 | 12,000 | | 50 |
| " | " | | | | 8432 | 20 | 8,000 | | 50 |
| " | " | | | | 8433 | 20 | — | | — |
| | " | | | | 8434 | 0 | 0 | | |
| | " | | | | 8435 | 0 | 0 | | |
| | " | | | | 8436 | 0 | 0 | | |
| | " | | | | 8437 | 0 | 20 | | |
| | " | | | | 8438 | 0 | 0 | | |
| | " | | | | 8439 | 0 | 20 | | |
| " | 1 ug (Lot #2) | | | | 8440 | 0 | 20 | | |
| " | " | | | | 8441 | 0 | 20 | | |
| " | " | | | | 8442 | 0 | 0 | | |
| " | " | | | | 8443 | 0 | 0 | | |
| " | " | | | | 8444 | 0 | >20 | | |
| " | " | | | | 8445 | 0 | >20 | | |
| " | 1 ug (Lot #3) | | | | 8446 | 0 | >20 | | |
| " | " | | | | 8447 | 0 | >20 | | |
| " | " | | | | 8448 | 0 | >20 | | |
| " | " | | | | 8449 | 0 | >20 | | |
| " | " | | | | 8450 | 20 | >20 | | |
| " | " | | | | 8451 | 0 | 20 | | |
| " | | | 10 ug | 1 ug | 8452 | 0 | 0 | | |
| " | | | " | " | 8453 | 0 | 20 | | |
| " | | | " | " | 8454 | 0 | 0 | | |
| " | | | " | " | 8455 | 0 | 0 | | |
| " | | | " | " | 8456 | 0 | 20 | | |
| " | | | " | " | 8457 | 0 | 0 | | |
| " | 1 ug (Lot #1) | | | | 8458 | 0 | — | | |
| " | " | | | | 8459 | 0 | — | | |
| " | " | | | | 8460 | 0 | — | | |
| " | " | | | | 8461 | 20 | — | | |
| " | " | | | | 8462 | 0 | — | | |
| " | " | | | | 8463 | 0 | — | | |
| " | 1 ug (Lot #1) | 10 ug | | | 8464 | >20 | — | | |
| " | " | " | | | 8465 | 2,000 | — | 500 | |
| " | " | " | | | 8466 | 500 | — | | |
| " | " | " | | | 8467 | 500 | — | 500 | |
| " | " | " | | | 8468 | 4,000 | — | 50 | |
| " | " | " | | | 8469 | 500 | — | | |

| | | | | | | RECIPROCAL TITER | | AFFINITY (ng/ml) | |
|---|---|---|---|---|---|---|---|---|---|
| BCG(-14d) | PND(MN)-PPD | PND(MN)-TA(ADH) | PND(MN) | PPD | GP # | Day 28 | After Boost-Day 42 | Day 28 | After Boost-Day 42 |
| " | | 1 ug | | | 8475 | 0 | >20 | | |
| " | | " | | | 8476 | 0 | >20 | | |
| " | | " | | | 8477 | 0 | >20 | | |
| " | | " | | | 8478 | 20 | >20 | | |
| " | | " | | | 8479 | 0 | 20 | | |
| " | | " | | | 8480 | 0 | >20 | | |
| " | | 10 ug | | | 8481 | 2,000 | 4,000 | 500 | 50 |
| " | | " | | | 8482 | 20 | 1,000 | | 50 |
| " | | " | | | 8483 | 500 | 4,000 | | 50 |
| " | | " | | | 8484 | 1,000 | 1,000 | 50 | 50 |
| " | | " | | | 8485 | >20 | 500 | | 50 |
| " | | " | | | 8486 | >20 | 4,000 | | 50 |
| | | " | | | 8487 | >20 | 500 | | 500 |
| | | " | | | 8488 | >20 | 500 | | 500 |
| | | " | | | 8489 | >20 | 500 | | 500 |
| | | " | | | 8490 | 2,000 | 2,000 | 500 | 50 |
| | | " | | | 8491 | 20 | 1,000 | | 50 |
| | | " | | | 8492 | 500 | 500 | 500 | 100 |
| " | | 1 ug | | 1 ug | 8493 | 20 | 2,000 | | 100 |
| " | | " | | " | 8494 | 0 | 20 | | 5,000 |
| " | | " | | " | 9495 | 20 | 20 | | 1,000 |
| " | | " | | " | 8496 | 0 | 20 | | 1,000 |
| " | | " | | " | 8497 | 0 | 1,000 | | 100 |
| " | | " | | " | 8498 | 0 | 500 | | 500 |
| " | | 10 ug | | " | 8499 | 1,000 | 1,000 | 500 | 100 |
| " | | " | | " | 8500 | 2,000 | 4,000 | 50 | 50 |

TABLE 26-continued

Reciprocal titers and affinity of antibody in sera of guinea pigs

| " | " | " | 8501 | 500 | 2,000 | | 100 |
|---|---|---|---|---|---|---|---|
| " | " | " | 8502 | 4,000 | 12,000 | 50 | 50 |
| " | " | " | 8503 | 500 | 4,000 | | 50 |
| " | " | " | 8504 | 500 | 4,000 | 500 | 50 |
| " | 1 ug | 1 ug (Alum) | 8505 | 20 | 500 | | 500 |
| " | " | " | 8506 | 1,000 | 2,000 | 500 | 500 |
| " | " | 1 ug (Alum) | 8507 | 100 | 500 | | 100 |
| " | " | 1 ug (Alum) | 8508 | 4,000 | 4,000 | 500 | 50 |
| " | " | 1 ug (Alum) | 8509 | 4,000 | 50 | 50 | 100 |
| " | " | 1 ug (Alum) | 8510 | 100 | 500 | | 100 |
| " | 10 ug | 1 ug (Alum) | 8511 | 4,000 | 500 | 500 | 50 |
| " | " | 1 ug (Alum) | 8512 | 1,000 | 1,000 | 500 | 100 |
| " | " | 1 ug (Alum) | 8513 | 4,000 | 4,000 | 500 | 100 |
| " | " | 1 ug (Alum) | 8514 | 2,000 | 4,000 | 500 | 50 |
| " | " | 1 ug (Alum) | 8515 | 500 | 8,000 | 500 | 50 |
| " | " | 1 ug | 8516 | 4,000 | 4,000 | 50 | 50 |
| " | 1 ug (Lot #1) | 1 ug | 8517 | 500 | 4,000 | 500 | 50 |
| " | " | " | 8518 | 20 | 500 | | 500 |
| " | " | " | 8519 | 500 | 4,000 | 500 | 100 |
| " | " | " | 8520 | 20 | 4,000 | | 500 |
| " | " | " | 8521 | 20 | 2,000 | | 100 |
| " | " | " | 8522 | 20 | 4,000 | | 50 |

EXAMPLE XII
Immunization of Rabbits with Conjugates of Various Peptides Coupled to KLH Rabbits were immunized with vaccines comprising various peptides coupled to the carrier KLH as described above. The peptides coupled to KLH were (GPGRAF)$_3$ (SEQ ID NO:16)C (282), IYIGPGRAC (SEQ ID NO:2)(283), IAIGPGRAC (SEQ ID NO:3)(284) and IHIGPGRAC (SEQ ID NO:4)(285). Table 27, below, shows the percentages of inhibition of HIV for each vaccine, as calculated against the control serum.

TABLE 27

Inhibition of HIV for various peptides coupled to KLH

| Serum Dilution | 1:25 | 1:50 | 1:100 | 1:200 |
|---|---|---|---|---|
| HIV-MN Control | 193,500 | 182,400 | 193,600 | 243,200 |
| Control Serum | 139,700 | 152,400 | 140,900 | 179,300 |
| 282 (GPGRAF)3C | 25,370 (81.9%) | 25,770 (83.1%) | 19,170 (86.4%) | 214,300 (19.2%) |
| 283 IYIGPGRAC | 20,970 (85.1%) | 27,470 (82.0%) | 28,660 (79.7%) | 128,800 (28.2%) |
| 284 IAIGPGRAC | 29,820 (78.7%) | 91,620 (72.7%) | 95,100 (32.4%) | 191,900 (7.0%) |
| 285 IHIGPGRAC | 41,340 (70.5%) | 108,000 (29.2%) | 177,100 (26.0%) | 215,900 (20.4%) |

FIG. 9 represents the results of immunization of rabbits with various peptides coupled to KLH. The symbols (W, O, F and °) represent the peptides with which the rabbits were immunized. The abscissa represents the peptide with which the ELISA plate was coated and the concentration of peptide in the well. Reactivity with low peptide concentration represents high affinity antibody. FIG. 10 represents the results of immunization of rabbits with various peptides coupled to KLH. The abscissa represents reciprocal rabbit serum dilution reactivity with a peptide-(amino acid sequence shown on the top of the graph) coated ELISA plate with optimal peptide concentration.

EXAMPLE XIII
Immunization of Guinea Pigs with Conjugates of MN-PND Coupled to PPD or Toxin A HIV-1 MN strain obtained from the AIDS Reference and Reagents-Programs was propagated in H9 cells. H9 cells were grown on RPMI (BRL-Gibco, Gaithersburg, Md.) and heat-inactivated fetal calf serum. Cells were grown in 75 cm$^2$ flasks (Corning Glass Works, Corning, N.Y.) in 5% CO$_2$ at 37° C. in a humidified incubator. Cell-free virus particles were obtained by centrifuging H9 cells chronically infected with HIV-1$_{MN}$ for 30 minutes at 4° C. The cell-free supernatant was collected, filtered, aliquoted, and stored at −70° C. Virus infectious titer was determined by incubating quadruplicate samples of serially diluted viral supernatant in 1.5 ml of media containing $2 \times 10^5$ H9 cells/well. After culturing for 18 days, the P24 content of the supernatant was determined using a commercial antigen capture assay (DuPont). The highest dilution of the virus stock that yielded a productive infection in 50% of the wells was defined as the tissue culture infective dose 50 ($TCID_{50}$). For neutralization assays, guinea pig sera was heat-inactivated at 56° C. for 30 minutes. The sera was diluted (1:25 to 1:1500 final dilution) in growth medium and incubated with 100 $TCID_{50}$ of HIV-$1_{MN}$ for 2 hours at 37° C. and then added to cultured H9 cells ($2 \times 10^5$/well). Controls included growth medium without sera and similarly diluted normal guinea pig serum. Following 18 days of cultivation, an aliquot of cell-free culture supernatant was assayed for P24 antigen content. Control wells (no added serum) contained between 180 to 213 ng of P24/ml, while wells with normal guinea pig serum contained 180 to 253 ng of P24/ml. Neutralizing capacity was determined by comparing the P24 antigen content of the test serum samples with those which contained an identical dilution of control serum. Titer is defined as the reciprocal of the highest dilution of serum which effected a $\geq 90\%$ decline in P24 content. Table 28, below, shows the antibody response after immunization with MN-PND-PPD or MN-PND-toxin A conjugate vaccines.

PND-TA conjugate (equal to 10 mg of MN-PND peptide) by the intramuscular route. Where indicated, animals were primed by vaccination with $10^7$ BCG 2 weeks prior to receiving the first dose of vaccine.

IgG antibodies to the MN-PND peptide were measured by ELISA as follows. To each well of 96-well microtiter plate. was added 100 ml of a 5 mg/ml solution of peptide in 0.1 M $NaHCO_3$ (pH 9.6). The plates were incubated overnight at room temperature. After coating, the liquid was aspirated and unbound sites were blocked by the addition of phosphate buffered saline containing 0.1% (wt/vol) casein, 0.05% Tween 20 and 0.0004% (wt/vol) rhodamine. The test sera were serially diluted in the above buffer and 100 ml added per well. After incubation for 1 hour at 37° C., the plates were washed and peroxidase-labeled anti-guinea pig IgG was added. After incubation for 1 hour at 37° C., the plates were again washed and substrate added. The absorbance at 405 nm was measured after 30 minutes of incubation at room temperature using a Titertek Multiscan (Flow Laboratories, McLean, Va.). Serum samples from the same animal were run in parallel on the same plate. On each plate were also run positive and negative control sera. Titers were determined by multiplying the optical density (OD) of a serum sample which fell within the linear range ($A_{405}$ 0.2–0.8) by its reciprocal. Table 29, below, shows recogni-

TABLE 28

Anti-MN-PND IgG antibody response after immunization with MN-PND-PPD or MN-PND-TA conjugate vaccines

| | | Geometric mean ELISA titer (range) | | | |
|---|---|---|---|---|---|
| Vaccine | BCG Priming | Day 0 | 28 | 56 | 84 |
| PND-PPD | No | <2 | <2 | 2.4 (<2–19) | 75 (10–5064) |
| | Yes | <2 | 8.3 (4–35) | 1845 (357–5456) | 9035 (7968–19,712) |
| PND-TA | Yes | <2 | 53 (8–393) | 624 (270–1744) | 149 (39–309) |
| PND-PPD + PND-TA | Yes | <2 | 17 (<2153) | 957 (250–2040) | 599 (158–1300) |

Guinea pigs (groups of 5–6) were immunized on days 0, 14, 28, and 56 with 1 mg of the PND-PPD conjugate (equal to 0.65 mg of MN-PND peptide) or with 50 mg of the tion of heterogenous PND peptides and GPGRAF motif following immunization with the MN-PND-PPD and MN-PND-Toxin A conjugate vaccines.

TABLE 29

Recognition of heterologous PND peptides and GPGRAF motif following immunization with MN-PND vaccines

| PND-PPD | PND peptide (strain of HIV-1) | Peak geometric mean titer | Peak geometric mean antibody affinity (ng peptide/ml) |
|---|---|---|---|
| PND-PPD | KRIHIGPGRAFYT (MN) | 9035 | 20 |
| | KSIHIGPGRAFYA (SC) | 1045 | 301 |
| | KSITKGPGRVIYA (RF) | 11 | 3465 |
| | KGIAIGPGRTLYA (NY-5) | 6 | 2201 |
| | SRVTLGPGRVWYT (CDC42) | 3 | 7578 |
| | GPGRAF[3] | 478 | 397 |
| PND-TA | KRIHIGPGRAFYT (MN) | 624 | 71 |
| | KSIHIGPGRAFYA (SC) | 171 | 89 |
| | KSITKGPGRVIYA (RF) | 10 | 8908 |
| | KGIAIGPGRTLYA (MY-5) | 34 | 500 |
| | SRVTLGPGRVWYT (CDC42) | 3 | 10,000 |
| | GPGRAF[3] | 1581 | 500 |
| PND-PPD + | KRIHIGPGRAFYT (MN) | 957 | 56 |
| | KSIHIGPGRAFYA (SC) | 500 | 89 |
| | | | 10 |

TABLE 29-continued

Recognition of heterologous PND peptides and GPGRAF motif
following immunization with MN-PND vaccines

| PND-PPD | PND peptide (strain of HIV-1) | Peak geometric mean titer | Peak geometric mean antibody affinity (ng peptide/ml) |
|---|---|---|---|
| PND-TA | KSITKGPGRVIYA (RF) | 58 | 10,000 |
|  | KGIAIGPGRTLYA (MY-5) | 45 | 1523 |
|  | SRVTLGPGRVWYT (CDC42) | 12 | 5407 |
|  | GPGRAF[3] | 3623 | 416 |

Non-antigen limited and antigen limited ELISA to detect total anti-PND antibodies and high affinity anti-PND antibodies, respectively, were performed. Table 30, below, shows in vitro neutralization of the MN strain of HIV by guinea pig sera.

TABLE 30

In vitro neutralization of the MN
strain of HIV by guinea pig sera

| Vaccine | Geometric mean neutralizing titer (Range) |
|---|---|
| MN-PND-PPD | <25 |
| MN-PND-TA | 733 (500–1500) |
| MN-PND-PPD + MN-PND-TA | 487 (500–1500) |

Figure 11:
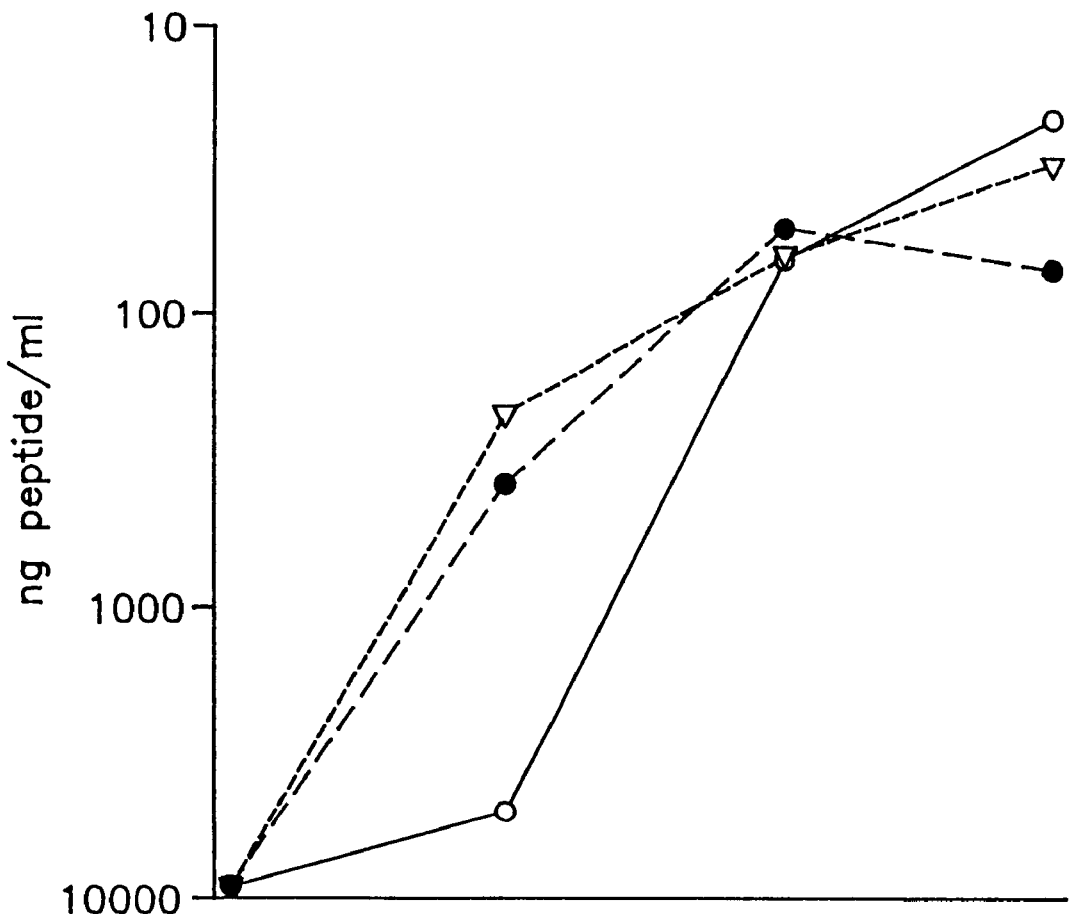
FIG. 11 represents the antibody results of immunization of BCG-primed and non BCG-primed guinea pigs with MN-PND coupled to PPD or toxin A.
Figure 12A:
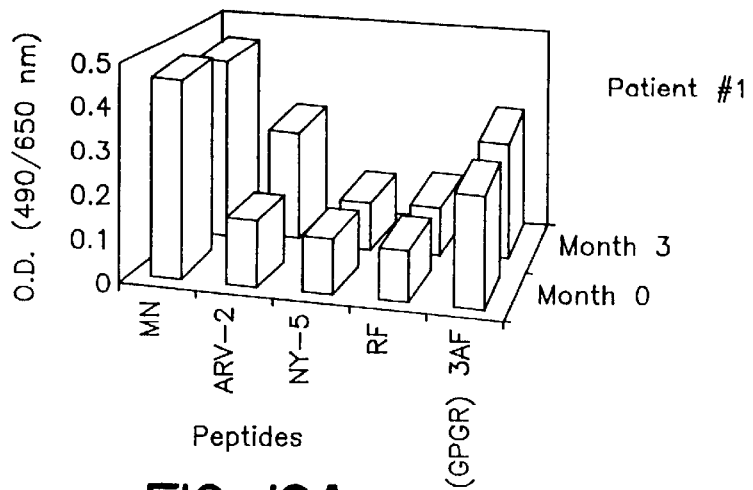
FIGS. 12A–12G set forth antibody responses following three monthly immunizations with the PPD-pentapeptide-PND vaccine (OD=optical density at 490/650 nm). ELISA plates were coated with the respective peptide at peptide concentration of 1 µg/ml per well.
Figure 12B:
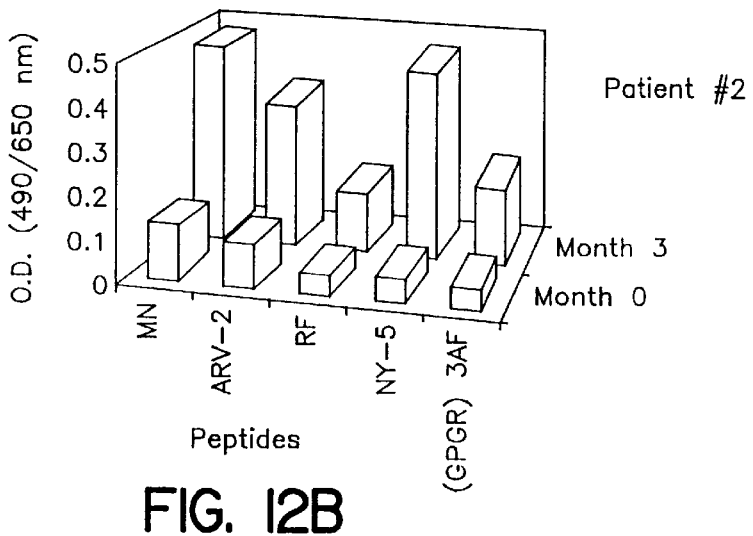
Figure 12C:
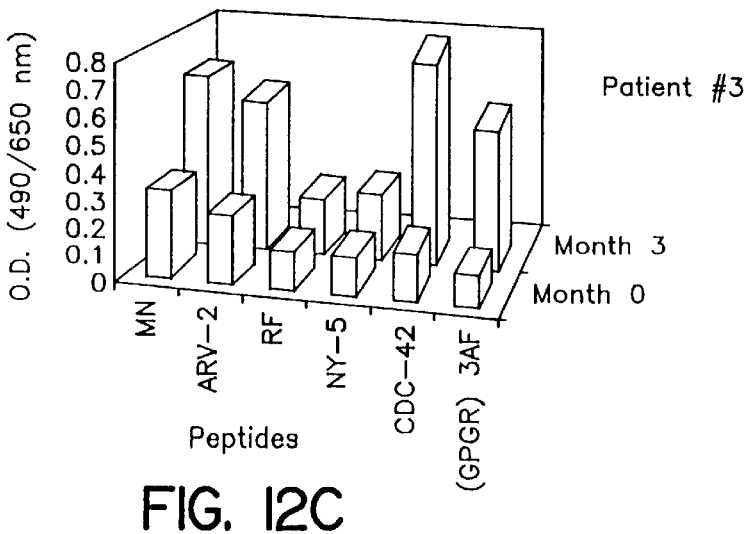
Figure 12D:
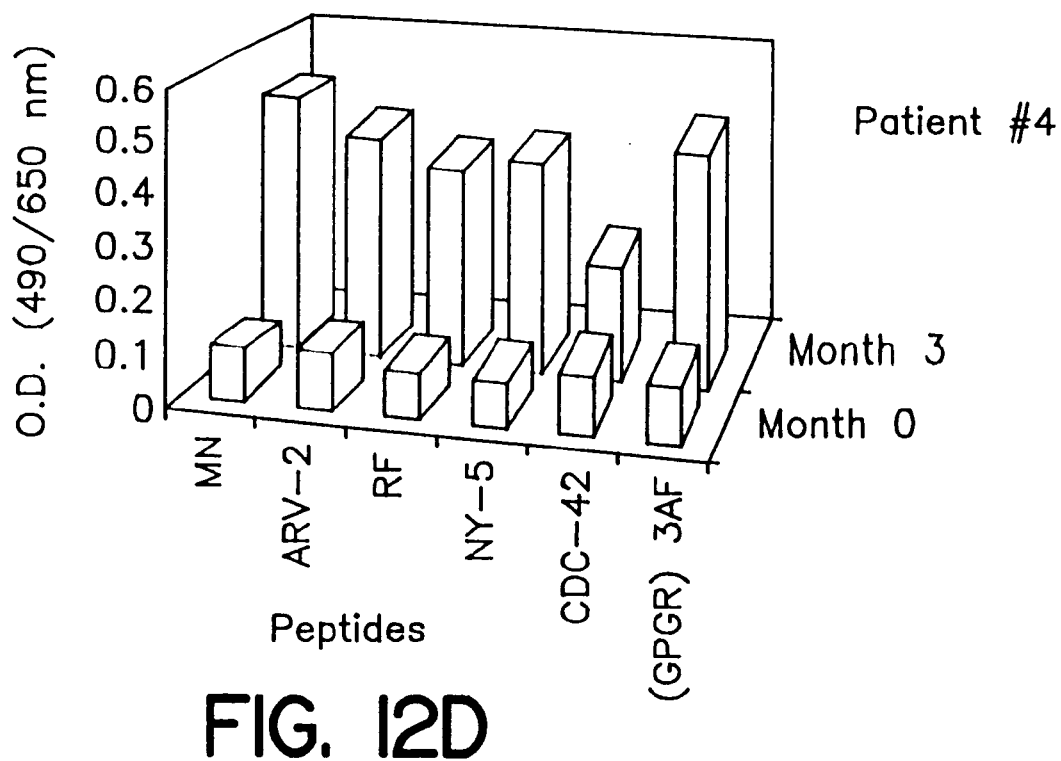
Figure 12E:
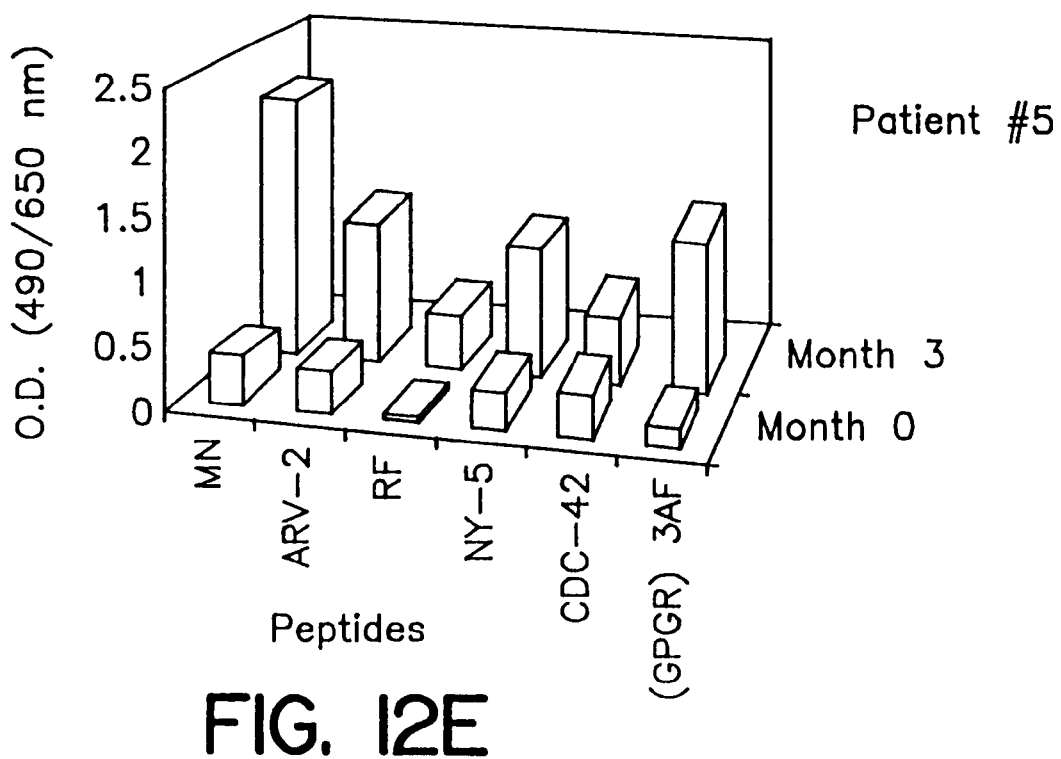
Figure 12F:
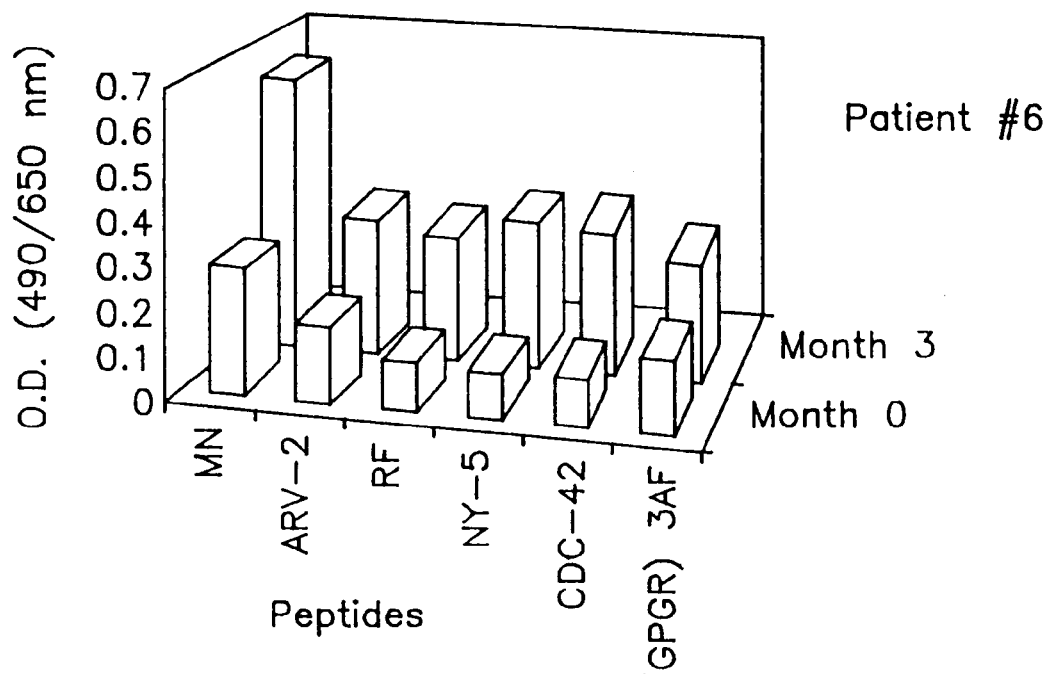
Figure 12G:
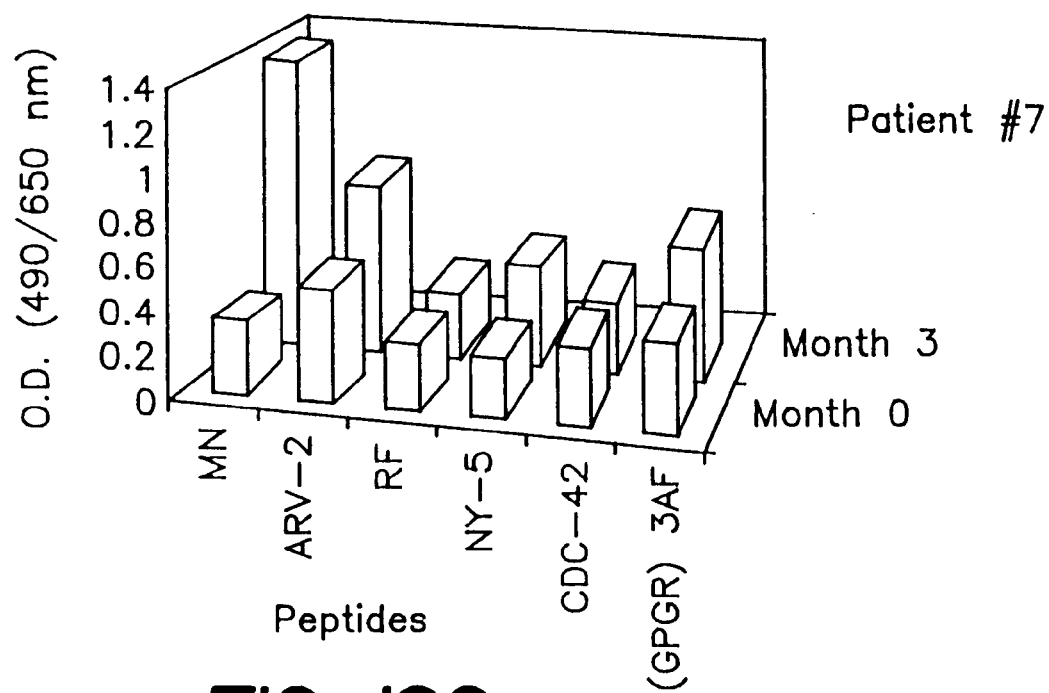

FIG. 11 shows maturation of high affinity anti-MN-PND antibody response. An antigen limited ELISA was used to detect high affinity antibody. ELISAs were performed as described, with the exception that each of eight microtiter plate rows were coated overnight by the addition of 5,000, 1,000, 500, 100, 50, 10, 5, or 0 ng peptide/ml (100 ml/well). Serum samples were diluted 1:20 and 100 ml added per well. Antibody affinity was assigned the value of the lowest concentration of peptide which gave an absorbance ≧5 standard deviations above the negative control serum. Animals (groups of 5–6) were vaccinated on days 0, 28, and 56 with PND-PPD (o), PND-TA ("), or PND-PPD-plus PND-TA (W). Immunization with the MN-PND-Toxin A vaccine induced the production of antibodies capable of neutralizing HIV MN in vitro.

EXAMPLE XIV
Immunization of Guinea Pigs with Conjugates of Peptides Coupled to PPD A polyvalent vaccine was formed by conjugating peptides from the principal neutralizing domain of various strains of HIV to the carrier PPD. Specifically, peptide KSIYIG-PGRAFHT (SEQ ID NO:7) from HIV strain ARV-2, peptide SRVTLGPGRVWVYT (SEQ ID NO:9) from HIV strain CDC-42, peptide KRIHIGPGRAFYT (SEQ ID NO:1) from HIV strain MN, peptide KGIAIGPGRTLYA (SEQ ID NO:8) from HIV strain NY-5 and peptide KSITKGPGRVIYA (SEQ ID NO:7) from HIV strain RF were each coupled to the carrier PPD. After conjugating each of the 5 peptides to PPD, 3 mg of each conjugate was combined to obtain a 15 mg polyvalent vaccine.

First, 6 guinea pigs were A primed with BCG. After priming the guinea pigs, each guinea pig was injected with 5 mg of the polyvalent (pentavalent) vaccine. At a later date, sera from the vaccinated guinea pigs was analyzed in an ELISA of the invention.

Table 31, below, shows the GM ELISA titer for all 5 vaccine components. Sera was assayed at days 0, 42, 56 and 78. All 5 of the vaccine components elicited a significant antibody response when compared to baseline values. As shown in Table 31, the KRIHIGPGRAFYT peptide from the MN strain of HIV was the most immunogenic and KSIT-KGPGRVIYA peptide from the RF strain of HIV was the least immunogenic. This data shows that multiple monovalent conjugates of this invention can be combined to yield an immunogenic multivalent vaccine.

TABLE 31

Immunogenicity of Polyvalent PND-PPD Conjugate Vaccine in Guinea Pigs

| VACCINE | DOSE | DAY | GH ELISA TITER | | | | | |
|---|---|---|---|---|---|---|---|---|
| | | | ARV-2 | CDC-42 | MN | MY-5 | RF | THAI-2 |
| PND-PPD (289) | 3 ug | 0 | <2 | <2 | <2 | <2 | <2 | <2 |
| | | 42 | 15 | 6 | 14 | 26 | 8 | 5 |
| | | 56 | 551 | 148 | 745 | 852 | 164 | 31 |
| | | 78 | 5773 | 2780 | 7342 | 8571 | 5163 | 1441 |
| PND-PPD (289) | 0.5 ug | 0 | <2 | <2 | <2 | <2 | <2 | <2 |
| | | 42 | 4 | 4 | 5 | 1 | 4 | 2 |
| | | 56 | 26 | 23 | 27 | 51 | 16 | 9 |
| | | 78 | 1068 | 740 | 2302 | 3869 | 568 | 122 |

Groups of guinea pigs [5–6] were primed with 10[7] BCG 2 months before immunization.
PND-PPD immunizations on days: 0, 14, 28, 42 and 56.

EXAMPLE XV
Peptides Used in the Multiepitope PPD/10 kMtb Vaccines

V3 loop peptides. Linear peptides from amino acids 307–319 associated with the $V_3$ loop region were synthesized as set forth in Devash, et al. *Proc. Natl. Acad. Sci USA* 1991; 87:345–49 and Kollman, et al. *Proc. Natl. Acad. Sci.*

1996; 93:3126–31. No longer than 18 amino acid sequences were prepared which represented THAI-I, THAI-II, MN RF, NY-5, CDC-42, ARV-2 and a representative Brazilian strain were synthesized.

gp41 peptides. The 6 amino acid peptide ELDKWA shown by Katinger (Muster, et al. *J. Virol.* 1994; 68:4031–34) to be the target of a cross-neutralizing monoclonal antibody with two additional LL (LLEDKWA) (SEQ ID NO:10) was synthesized as a single motif and a repetitive motif of 16 amino acids. The peptide sequence without the additional two LL is non immunogenic.

Nef peptides. The selection of nef epitopes is based on the conserved features of nef sequences, on their functional properties (Nixon, D. F., et al. *AIDS* 5:1049, 1991; Cheingsong-Popov, R., et al. *AIDS Res. & Human Retrov.* 6:1099, 1990; Schneider, et al. *AIDS Res. & Human Retrov.* 1:37, 1991; Siakkou, H., et al. *Arch. Virol* 128:81, 1993; Culmann, B., et al. *J. Immunol.* 146:1560, 1991; Yu, G., et al. *Virology* 187:46, 1991; Shugars, D. C., et al. *J. Virol.* 67:4639–4650, 1993; Venet, A., et al. *AIDS Res. & Human Retrov.* S41, 1993; Robertson, M. N., et al. *AIDS Res. & Human Retrov.* 9:1217: 23, 1993) and on sequences found missing in patients with "non-virulent" HIV-1 disease (long-term non-progressors). Sequences known to induce both humoral and CTL responses (Cheingsong-Popov, R., et al. *AIDS Res. & Human Retrov.* 6:1099,. 1990; Schneider, et al. *AIDS Res. & Humra Retrov.* 1:37, 1991; Siakkou, H., et al. *Arch. Virol* 128:81, 1993; Culmann, B., et al. *J. Immunol.* 146:1560, 1991; Robertson, M. N., et al. *AIDS Res. & Human Retrov.* 9:1217: 23, 1993) are selected. Other peptides that may be employed include, for example:

a. RPMTYK (SEQ ID NO:11)—a highly conserved recognition site for phosphorylation by protein kinase C:

b. GGKWSK (SEQ ID NO:12)—a nearly invariant myristilation site which lies on the external surface of the folded nef protein.

c. PGPGIRY (SEQ ID NO:13) and GPGIGPGV (SEQ ID NO:14) located at positions 13–138, a highly conserved region predictive of a beta turn (Shugars, D. C., et al. *J. Virol.* 67:4639–4650, 1993).

Carriers for the PND peptides. PPD: several lots from different manufacturers and the same manufacturer were tested for immunogenicity. Recombinant proteins from *M. tuberculosis* and *M. leprae:* Cloning and expression of the genes of the secreted 10 kDa and 32 kDa from *M. tuberculosis* and *M. leprae* were synthesized. Linear co-expression of 10 kDa and PND yielded a 1:1 ratio between both components resulted in poor immunogenicity. Conjugation of peptides to 10 kDa *M. tuberculosis* and to 10 kDa *M. leprae* using glutaraldehyde allowed a 4–5:1 peptides/protein molar ratio could be conjugated to each protein molecule. Toxin A from *Pseudomonas aeruginosa:* Toxin A (TA) was irreversibly detoxified by covalently coupling to adipic acid dihydrazide and allowing haptens to be coupled through the nonreacted hydrazide groups (Lussow, et al. *Proc. Natl. Acad. Sci. USA* 1990; 87:2960). Filamentous Hemagglutin (FHA) of *Bordetella permusis:* PND peptides were covalently coupled to FHA using the ADH/Carbodimide reaction at a molar ratio of 10–12:1. T helper cell (Th) epitopes of tetanus toxoid (TT): Conjugation of HIV peptides to T helper cell epitopes of tetanus toxoid was performed. Several peptides from the TT described to be universal Th cell epitopes recognized by the majority of the human population. were synthesized. TT Th epitopes and HIV peptides were chemically coupled to liposomes or virosomes. Glucoconjugate-with synthetic peptides: Capsular polysaccharide from Group B streptococcus and Dextra T-500 were coupled by reductive amination in the presence of sodium cyanoborohydride to PND-NY5-PND, and to 10 kDa *M. tuberculosis* NY5-PND at different ratios.

EXAMPLE XVI

Animal Immunization

Immunogenicity of PPD-Mn-PND conjugates. Guinea pigs were primed by intramuscular $10^7$ CFU of BCG 14 days prior to the first PND vaccination. BCG priming was required to obtain an anti-Mn-PND antibody response. The lowest dose of peptide capable of engendering. an immune response was titrated. BCG-primed guinea pigs were immunized with 0.5–3.0 $\mu$6 PPD PND. Following five doses of 1 $\mu$g PND (day 98) there was a greater than 100-fold rise in anti-Mn-PND antibody titer. In contrast to the TA-PND, the peak GMT antibody titer of 9,035 was achieved with the PPD-PND conjugate only after 3 immunizations. These antibodies possessed a very high mean affinity for the MN-PND peptide, cross- reacted with PND peptides from SC, RF, NY5, neutralized HIV-1 MN prototypes at higher titers than (1:3600) TA-PND but also failed to neutralize primary isolates.

Hexa-PND-PPD conjugates. Guinea pigs were immunized with either 0.65 microgram of MN-PND-PPD or with 3.0 microgram of the hexa-PND-PPD conjugate mixture (0.5 microgram per peptide). Table 1 shows the geometric mean titer (GMT) of antibodies to the primary neutralizing domain (PND) in guinea pigs immunized with a hexa-PND-peptide-PPD versus a mono pnd (MN-peptide-PPD vaccine. The GMT of antibodies to the hexa-peptide vaccine were about 15 fold higher and more broadly cross-reactive as compared to- the mono-peptide vaccine. Furthermore, the hexa-peptide induced for the first time neutralizing antibodies of high titer also to primary isolates (Table 32). The PPD hexa-PND vaccine also induced neutralizing antibodies for primary HIV-1 isolates in PBMC at 1:45–1:135 titers (see Table 33).

TABLE 32

Immunogenicity (GMT) of 3 $\mu$g of a hexa-peptide PND-PPD conjugate vaccine (0.5 g per peptide) versus 0.65 $\mu$g of a mono-peptide (MN) PND-PPD conjugate vaccine.

| | Mono-PND peptide MN-PPD Conjugate | Hexa-PND-peptide PPD Conjugate | | | | | |
|---|---|---|---|---|---|---|---|
| Day Post-Vaccine | MN | MN | RF | NY5 | ARV-2 | CDC-2 | THAI-2 |
| 0 | <2 | <2 | <2 | <2 | <2 | <2 | <2 |
| 42 | 2.4 | 14 | 8 | 26 | 15 | 6 | 5 |

TABLE 32-continued

Immunogenicity (GMT) of 3 µg of a hexa-peptide PND-PPD conjugate vaccine (0.5 g per peptide) versus 0.65 µg of a mono-peptide (MN) PND-PPD conjugate vaccine.

| | Mono-PND peptide MN-PPD Conjugate | | Hexa-PND-peptide PPD Conjugate | | | | |
|---|---|---|---|---|---|---|---|
| Day Post-Vaccine | MN | MN | RF | NY5 | ARV-2 | CDC-2 | THAI-2 |
| 56 | 121.1 | 745 | 164 | 852 | 551 | 148 | 31 |
| 78 | 462 | 7342 | 5163 | 8571 | 5163 | 2780 | 1441 |

Groups of 5–6 Guinea pigs were primed with $10^7$ BCG 2 months before immunization. Peptide immunizations were on days: 0, 14, 28, 42 and 56. Note: the mono-peptide PND conjugate vaccine induced cross-reactive antibodies with a GMT of s20 to RF, NYS, ARV-2, CDC-42 AND THAI-2 (not shown) as compared to GMT of up to 8,571 in the HEXA-PND-PPD vaccine.

TABLE 33

Neutralization of 100 $TCID_{50}$ of HIV-I-28 (primary patient isolated) in PBMC assay by sera from guinea pigs (gp) immunized with the hexa-PND-PPD vaccine (pg p24/ml).

| | Immunized gp Serum Dilution | | | | | | |
|---|---|---|---|---|---|---|---|
| gp # | 1:15 | 1.45 | 1:135 | 1:405 | 1:1,215 | 1:3,645 | Control |
| 9323 | 0.1* | 0.1 | 2,728 | 2,624 | 6,824 | 6,824 | 4,144 |
| 9325 | 0.1 | 0.1 | 0.1 | 2,595 | 2,873 | 3,545 | 4,114 |
| 9326 | 0.1 | 0.1 | 0.1 | 1,025 | 2,725 | 3,061 | 4,114 |
| 9333 | 0.1 | 124 | 538 | 558 | 639 | 1,443 | 4,114 |
| 9336 | 0.1 | 2,282 | 2,134 | 2,314 | 3,026 | 3,254 | 4,114 |
| 9337 | 0.1 | 0.1 | 1,106 | 1,830 | 3,524 | 2,456 | 4,114 |

BCG primed gp were immunized on days 0, 14, 28, 56. Sera tested were drawn on day 78.
*pg p24/ml. Note that in 4 of 6 gp there is significant neutralization of the primary isolate up to a dilution of 1:135. In gp 9333 there is neutralization up to a 1:3645 serum dilution. With the addition of fresh gp complement in one tested guinea pig the neutralization titer was increased about 100 fold in one tested guinea pig.

Immunization with 10 kDa and 32 kDa *M. tuberculosis* and *M. leprae* conjugates of MN-PND: These conjugates yielded the highest antibody titers after 3 to 8 monthly injections in BCG primed animals. Antibody titers were, however, about 5–10 fold lower than with PPD-MN conjugates.

Immunization of mice with NY5-PND coupled to 10 kDa *M. tuberculosis* or to PPD and to capsular Polysaccharides from group B Streptococcus 1b and Dextran T-500. BCG primed mice were immunized at days 0, 14, 28 and 91. Moderate antibody titers were obtained.

Immunization of mice with FHA and with tetanus T-helper epitopes (ThTT) with and without virosome or liposome formulations have shown results inferior to PPD-MN-PND (not shown).

Immunizations of mice with 10 kDa *M. tuberculosis* conjugates with nef, gp41 have shown unimpressive antibody titers to gp41 and moderate titers to nef peptides. These antibodies were, however, of high affinity and neutralized primary isolates at 1:25 dilutions.

Synergistic, sequential immunizations. Three monthly immunizations of guinea pigs with 10 kDa *M. tuberculosis* MN-PND and nef 10 kDa *M. tuberculosis* peptide mixture conjugate (animal 2521) or with MN-PND 10 kDa+gp41 10 kDa *M. tuberculosis* conjugate also resulted in moderate antibody titers to the respective peptides and both induced impressive consistent neutralization of primary HIV-1 isolates in PBMC (see Table 34).

TABLE 34

Neutralization of HIV-1 prototype an a primary isolates by guinea pigs immunized with MN-10 kDa *M. tuberculosis* followed by penta-Nef peptide-10 kDa *M. tuberculosis*, respectively, gp-41 peptide 10 kDa *M. tuberculosis* (pg p24/ml)

| | gp 2521 20 µg Nef-peptide-10 kDa | | gp 2517 10 µg gp41-peptide-10 kDA MTB | | gp 2501 5 µg gp41 | |
|---|---|---|---|---|---|---|
| Serum dilution | HIV prototype | primary isolate | HIV prototype | primary isolate | HIV prototype | primary isolate |
| Control | 58,643 | 35,516 | 38,790 | 33,303 | 73,746 | 646 |
| 1:15 | 4,702 | 2,303 | 3,637 | 2,528 | 3,929 | 8 |
| 1:45 | 9,970 | 12,477 | 7,097 | 8,681 | 7,070 | 12 |
| 1:135 | 43,787 | 20,047 | 34,572 | 21,002 | 29,115 | 10 |
| 1:405 | 47,274 | 20,283 | 69,722 | 30,825 | 71,828 | 25 |
| 1:1,215 | 85,890 | 40,147 | 74,631 | 40,943 | 68,790 | 1,206 |

HIV-1-MN prototype of 50 $TCID_{50}$ was tested in 119 target cells. HIV-1–59 primary isolate 200 $TCID_{50}$ was tested in PBMC immunization schedule: all gp were immunized intradermally with 50 µg of MN PND-10 kDa on days 0, 32, 62, 90 and 114. No primary isolate neutralizing antibodies were induced by this vaccine. Animals were rested to day 227. 2 animals were then immunized on day 227 and 270 with 5 µg, respectively, 10 µg of peptide 10 kDa, and one animal was immunized with four-Nef-peptide-10 kDa Mtb conjugate. Bloods were drawn on day 305. Note that in all 3 animals there was modest neutralization of both HIV prototypes and primary isolate. The studies in gp 2501 with primary isolate have to be repeated.

Figure 16A:
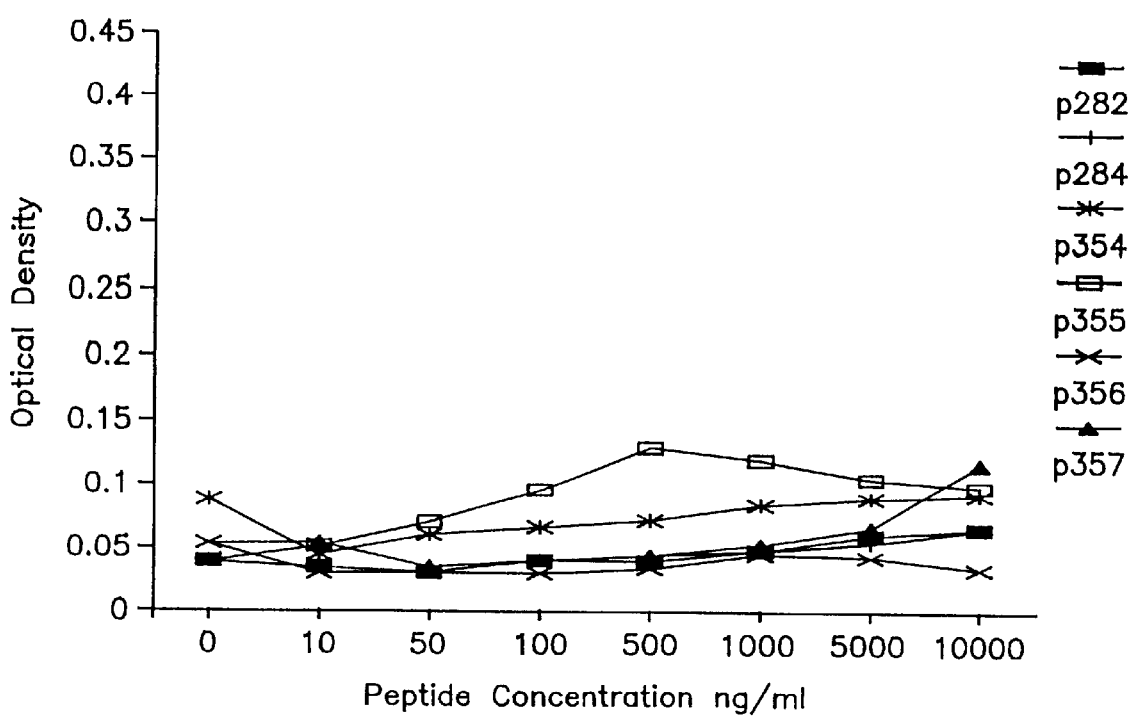
FIGS. 16A and 16B set forth the immunoreactivity pattern of serum from an HIV(+) PPD (+) patient before (FIG. 16A) and after (FIG. 16B) 2 intradermal immunizations with hexa-PND-peptide-PPD. Antigen limited ELISA utilizing PND (p282–p357) peptides of the vaccine. Note the increase of OD to 3 of the PND-peptides.
Figure 16B:
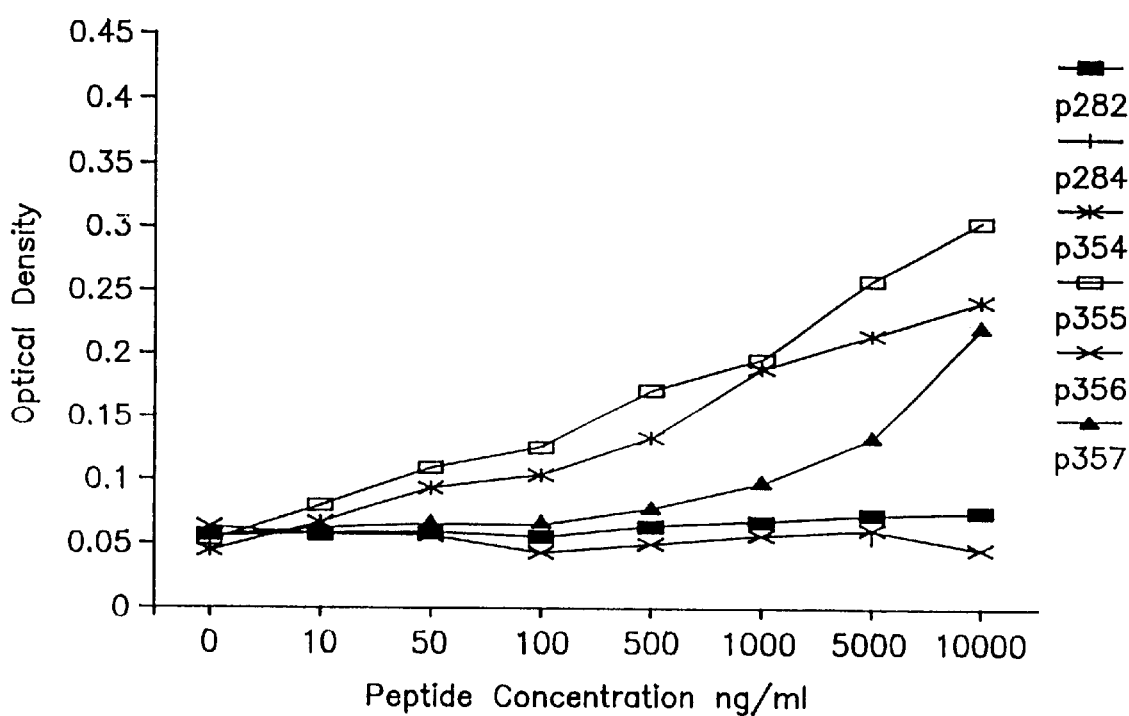
Figure 17:
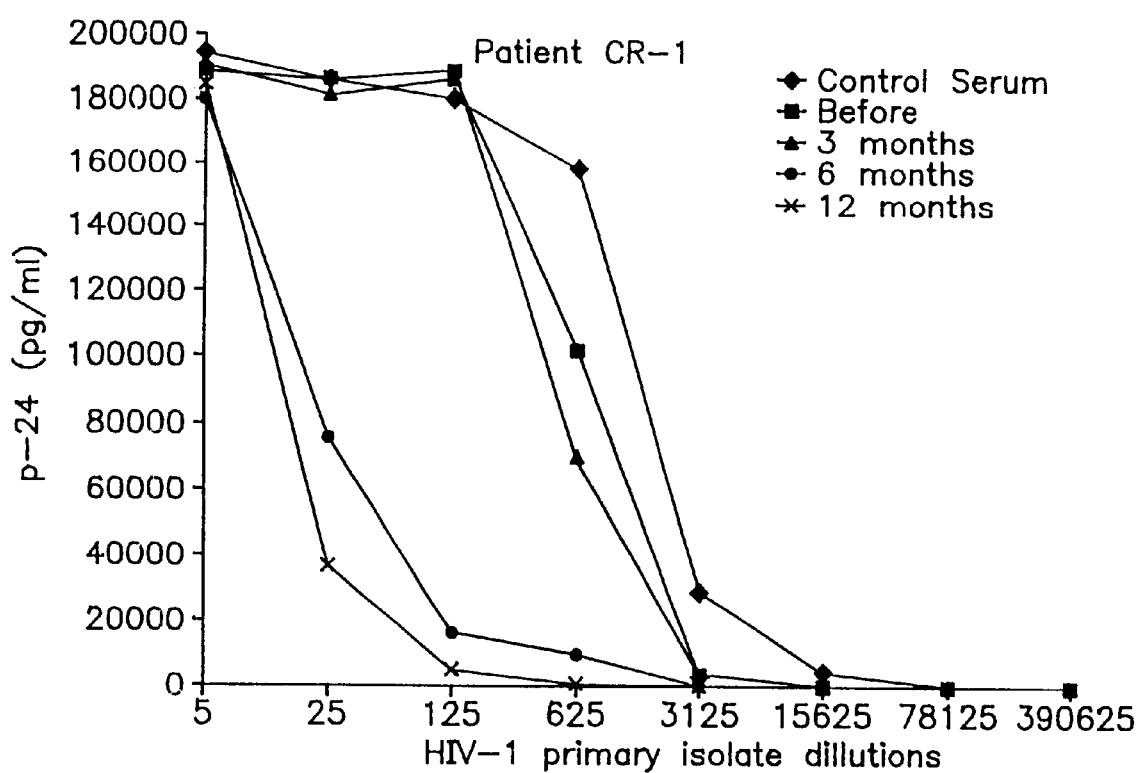
FIG. 17 sets forth the neutralization of HIV-1 primary isolates: in PBMC by serum from HIV(+) volunteers immunized with the PPD-hexa-PND-AIDS vaccine. The shift of the curves to the left indicates neutralization increment post: vaccination. Using the ACTG consensus log reduction assay, the TCID$_{50}$ reduction was calculated according to the Spearman-Kraber method, yielding in this volunteer a 267 fold increase in serum neutralizing capacity at 12 months post vaccinations.

Immunization of HIV infected PPD skin test positive volunteers with the hexa-PND-PPD conjugate vaccine. 7 patients with CD4 cells above 200 were selected. All patients had a positive skin test to PPD of 5 mm diameter or greater. Patients were immunized with 3.0 microgram of the 6 peptide mixture on days 0, 30, 90, 120, 180 and 240. All patients remained clinically stable over a period of 1 year, the CD4 cells increased in 3 and remained stable in the others. All patients developed extremely high titers (265 fold) of neutralizing antibody titers to primary isolates (FIGS. 16A and 16B and FIG. 17), a representative log reduction assay for HIV-1 primary isolates in one patient. The same pattern was shown in all patients receiving this vaccine by 12 months). No other vaccine has so far achieved such a remarkable immune response.

EXAMPLE XVII
Reduction in HIV Viral Load and Improved Neutralization of HIV-1 Primary Isolates Patients: Asymptomatic HIV-1 seropositive subjects were enrolled from the HIV clinic of the University of Tel-Aviv, Elias Sourasky Medical Center. Patients had to have a positive intradermal skin test to 2 tuberculin unit (TU) PPD (induration and/or erythema of $\geq 5$ mm after 48 hours). Laboratory eligibility criteria included routine laboratory variables (CBC, chemistries) within the normal ranges, a CD4+ cell count >250 cells/ml. Exclusion criteria included the use of antiretroviral combination therapy and any disorder meeting the USA 1987 Centers for Disease Control AIDS surveillance definition.

Seven patients, ages 24 to 46 who were PPD skin-test positive at the 2 TU intradermal dose were classified as eligible for the protocol. Two patients (#4 and #5) were on reverse transcriptase inhibitor monotherapy prior to and during vaccination (Table 35).

TABLE 35

Clinical status, CD4 cell count and viral load of HIV+, PPD+ vaccinees prior to immunization with the PPD-pentapeptide-PND conjugate.

| Patient # | Sex | Age | Clinical Symptoms | Antiretrovirals during immunizations | CD4 cells/cmm | Viral load PCR-RNA copies/cmm |
|---|---|---|---|---|---|---|
| 1 | F | 40 | Asymptomatic | None | 500 | 5,700 |
| 2 | M | 32 | Asymptomatic | None | 620 | 15,000 |
| 3 | M | 46 | Asymptomatic | None | 260 | <400 |
| 4 | M | 28 | Asymptomatic | ddI | 491 | <400 |
| 5 | M | 38 | Asymptomatic Psoriasiform | ddc | 440 | 12,000 |
| 6 | F | 26 | Asymptomatic | None | 490 | <400 |
| 7 | F | 24 | Asymptomatic | None | 450 | 1,100 |

The vaccine protocol was approved by an independent ethical committee at the University of Tel-Aviv, Israel and received approval according to the Helsinki Committee. Approval to utilize study subjects' specimen for testing at the Albert. Einstein College of Medicine was obtained from the University's Investigational Review Board.

Vaccine synthesis and characterization: PPD obtained from the Statens Serum Institute, Copenhagen, Denmark was a solution containing 1 mg PPD/ml equal to 50,000 TU/ml (1 $\mu$g PPD=50 TU).

$V_3$ loop peptides of the following sequences (representative for the HIV variant in parentheses), KRIHIGPGRAFYT (SEQ ID NO:1)(MN), RSIHIGPGRAFYA (SEQ ID NO:6)(ARV-2), KGIAIGPGRTLYA (SEQ ID NO:8)(NY-5), KSITKGPGRVIYA (SEQ ID NO:7)(RF), SRVTLGPGRVWYT (SEQ ID NO:9)(CDC-42), were prepared by standard solid phase synthesis. Peptide sequences were verified by analysis on an automated amino-acid analyzer and by high pressure liquid chromatography (HPLC).

The PPD-peptide conjugation was prepared with gluteraldehydes as previously reported. (Rubinstein A, et al. *AIDS* 1995; 9: 243–51). Five monovalent PPD-PND conjugates were combined in equal amount (based upon PPD contents) to yield the final vaccine which contained 50 TU PPD and 0.13 $\mu$g of each peptide or a total of 0.65 $\mu$g of the five $V_3$ loop peptides listed above.

Immunization Schedule: Participants were scheduled to be immunized monthly for the first 3 months and then at 3 month intervals to 18 months. Only patients #1–3 completed the whole regimen. Patients #4 and #6 received the last immunization at 12 months, patient #7 at 9 months and patient #5 at 6 months. All patients were followed for 18 months from entry to the study. The vaccine was given intradermally 25 TU PPD into each arm. All vaccinees were monitored for local and systemic reactions. A standard battery of complete blood counts and blood chemistry profiles were performed periodically. Blood specimen for research studies were all coded. The decoding of clinical and laboratory data was conducted only at the conclusion of the study.

$V_3$ loop enzyme-linked immunosorbent assay (ELISA): Microtiter ELISA plates (Nunc, Naperville, Ill., USA) were coated with the respective synthetic $V_3$ loop peptide and incubated with patient sera diluted 1:20 as previously reported. (Rubinstein A, et al. *AIDS* 1995; 9: 243–51; Devash Y, et al. *Proc Natl Acad Sci USA* 1991; 87: 345–49).

Antigen-limited ELISA: Microtiter ELISA plates were coated with a vaccine peptide or with $(GPGR)_3AF$ at decreasing concentrations from 10,000 ng/ml to 10 ng/ml, as previously reported. (Rubinstein A, et al. *AIDS* 1995; 9: 243–51; Devash Y, et al. *Proc Natl Acad Sci USA* 1991; 87: 34549). An optical density (OD) above background at $\leq 100$ ng/ml was considered to indicate affinity.

Virus Neutralization assays: (A) Infectivity reduction assay: The infectivity reduction assay estimates the reduction in the number of infectious units per/ml (IUPML) when treated with patient sera and progressive dilutions of viral stocks, according to the NIAID AIDS Clinical Trial Group consensus protocol. The assay was performed in 24-well plates using 5-fold dilutions of viral isolate (1:5 to 1:390, 625). Each 1:20 diluted serum sample was tested with a stocked, previously tittered inoculum of clinical isolates as reference virus (e.g. MN referenced, primary isolate HIV-1–59) or with autologous virus. The virus stock's $TCID_{50}$ was determined by the method of Spearman-Karber. Uniformity of donor target cells was secured by freezing sufficient PBMC's from a panel of previously tested donors. PBMC's were activated for 48 hours with PHA/IL-2 prior to use. Each sample of viral dilution was cocultured at 37° C. with activated donor PBMC ($1 \times 10^6$) for 14 days. Concurrent, neutralization controls and virus titration controls were performed in the same plate. On day 7 half of the medium was removed and saved for future testing, and replaced with fresh medium containing $0.5 \times 10^6$, 48 hours PHA/IL2 stimulated normal donor PBMC's. Cultures were terminated on day 14, and collected supernatant was tested for total p24 content. Infectivity reduction is expressed as the ratio of $log1D_{50}$ for the control and test serum (fold inhibition). A 0.3 log reduction was considered significant. (B) Resting cell assay was performed according to Zolla-Pazner and Sharpe. (Zolla-Pazner S, et al. *AIDS Res Hum Retrov* 1995; 11: 1449–58). A Clade B non-syncytium-inducing virus BZ167 was kindly provided by Dr. Zolla-Pazner. In addition, the Clade B primary isolate HIV-1–59 was used. Virus stock was diluted to 100 $TCID_{50}$. Serial serum dilutions were then added. to the wells. The percent inhibition by serum was calculated from the p24 counts at 1:625 serum dilutions of baseline serum as compared to a 12 month post immunization serum. An inhibition of more than $\geq 50\%$ was considered significant.

Viral load determination: This study was performed in duplicates with a commercial assay (NASBA; Organon, Teknika; Durham, N.C.), in which the lower limit of detection is 400 RNA-copies. Frozen specimen were batched and tested simultaneously. The intra-assay variability was 0.12–0.2 logs. Sustained changes in plasma HIV RNA levels greater than three fold over time were considered relevant. (Saag MS, et al. *Nature Medicine* 1996; 2: 625–29).

CD4 cell counts: CD4 cells were measured by flow cytometry by standard methods as previously described. (Devash Y, et al. *Proc Natl Acad Sci USA* 1991; 87: 345–49). Results The monovalent MN-peptide-PPD vaccine failed to induce in HIV-1 negative volunteers neutralizing antibodies to primary virus isolates, in contrast to the polyvalent vaccine (See Table 35) which induced long lasting. immunity with neutralizing antibodies to HIV-1 primary isolates, utilizing the novel principle of synergistic immunization. Immunization. with 10k and 30k M tuberculosis (Mtb) and M leprae conjugates with Hexa-PND conjugates showed similar results as for the PPD conjugates. Immunizations with hexa PND+gp41+nef peptide conjugates has yielded broader immune responses in guinea pigs than with any of the previous conjugates. Sequential immunizations have also yielded superb responses with consistent impressive neutralization of primary HIV-1 isolates.

Vaccine acceptability: A total of 64 vaccine doses were administered. No systemic reactions or laboratory abnormalities were noted. Typical local reactions at the intradermal vaccine site were redness and induration within 24–48 hours, which resolved within 2–4 days.

Antibody responses to the vaccine: By 3 months an increase in antibody titers to all 5 vaccine peptides and to the GPGRAF motif was noted in all patients (FIGS. 12A–12G). The antibody titer increased with additional immunizations and was maintained in all patients except for patients #5 and #7 who received the shortest course of vaccination (6 months, 9 months, respectively).

Affinity of serum antibodies: High affinity antibodies to vaccine peptides were noted in all vaccinees after the third boost (not shown). There was a further increase in affinity over time in all patients except in patients #5 and 7 who had the shortest vaccination course: in patient #5 (FIG. 13B) and #7 the affinity increased remarkably at 3 months (to an OD of 0.807 at the 10 ng/peptide well) but dropped back to baseline at month 12.

CD4 cell count: Overall, there was no dramatic change in CD4+ cell counts over the 18 months observation period. Five patients showed a decline ranging from 10 to 170 cells while 2 showed an increase (40, respectively 160 cells). Maximal increases or decreases over the study ranged from +340 to -170 (Table 5). There was no correlation between an increase or decrease in CD4+ counts and viral load.

TABLE 36

CD4+ cell counts/cmm post immunization with PPD-PND-pentapeptide conjugate.

| Patient # | Months Post Immunization | | | | | | | Maximal increase (decrease) CD4 cells/cmm | Net Change at 15–18 months over baseline CD4 cells/cmm |
|---|---|---|---|---|---|---|---|---|---|
| | 0 | 3 | 6 | 9 | 12 | 15 | 18 | | |
| 1 | 500 | 420 | 450 | 450 | 410 | 450 | 486 | -90 | -14 |
| 2 | 620 | 600 | 640 | — | 580 | 560 | 450 | -170 | -170 |
| 3 | 260 | 390 | 380 | 420 | 420 | 240 | 220 | +160 | -40 |
| 4 | 490 | 350 | 470 | 432 | 660 | 825 | 650 | +335 | +160 |
| 5 | 440 | 500 | 480 | — | 496 | 475 | 480 | +60 | +40 |
| 6 | 490 | 640 | 530 | 520 | 527 | 550 | 480 | +150 | -10 |
| 7 | 450 | 530 | 790 | — | 520 | 424 | — | +340 | -26 |

Virus neutralization: After 3 months of immunization there was a 2.7–10.8 fold increase in the HIV neutralizing antibody over baseline (Table 37; FIGS. 14A–14G). With subsequent doses of vaccine there was a substantial increase (36–172 fold) in neutralizing activity with the exception of patient #7 (Table 35; FIGS. 14A–14G). In patient #7 there was a decrease in the neutralization titer after discontinuation of immunizations. In. three out of four tested patients there was also a significant increase in neutralization of autologous virus (Table 37). Patient #7 who failed to neutralize autologous virus also did not neutralize primary isolates. Two patients (#2, #5) tested in the resting cell assay showed significant neutralization of primary isolates (Table 37).

TABLE 37

HIV-1 infectivity reduction (neutralization) assay* and resting cell neutralization assay** post vaccination with the PPD-PND-pentapeptide conjugate.

| | Fold Inhibition post/pre-immunization HIV-1 Infectivity reduction assay | | | % HIV-Inhibition Resting Cell Assay |
|---|---|---|---|---|
| | Primary Isolate | | Autologous Virus | Primary Isolate |
| Patient # | 6 months | 12 months | 12 months | 12 months |
| 1 | 2.7 | 108 | nd | nd |
| 2 | 5.0 | 53 | 20 | 80% |
| 3 | 4.8 | 53 | 17 | nd |
| 4 | 3.2 | 172 | nd | nd |
| 5 | 7.1 | 36 | nd | 84% |
| 6 | 10.8 | 53 | 18 | nd |
| 7 | 3.0 | 1.4 | 1.0 | nd |

*Using the NIAID-ACTG consensus log reduction assay. The TCID50 reduction was calculated according to the Spearman Kraber method.
**According to Zolla-Pazner AIDS Res & Human Retrov 1995; 11:1449.
nd = not done Virus Load: The viral load remained <400 copies throughout the study period in those patients who were negative at entry (#3 & #6; FIGS. 14A–14G). In the three patients (#1, #2 & #5) with substantial viral loads at enrollment, there was a progressive virus decline noted which lasted for at least 15 months. In patients #2 and #5, the viral load had decreased to <400 copies during the course of the study. In patient #4 and #7, who had low viral burdens at entry, vaccination effected a reduction to non-detectable limits. There was a clear trend towards an increase in viral loads in patients who did not receive routine booster doses of vaccine. For example, in patient #5 (last does of vaccination at 6 months) immunization effected a reduction in viral load from 14,000 copies to <400 copies by 9 months. While the viral load remained at undetectable levels from month 9 to 15, it increased dramatically to >18,000 by 18 months. A similar picture was seen in patient #7 who was last vaccinated at 9 months. By 9 months the viral load had dropped from roughly 1,200 to undetectable where it remained through month 12. However, by month 15 the viral burden had increased to 13,000.

Discussion

Relentless and high level of HIV-1 replication are responsible for the immune attrition in AIDS patients. (Saag M S, et al. *Nat Med* 1996; 625–29; Mellors J W, et al. *Ann Intern Med* 1995; 122: 573–79; Ho Dd, et al. *Nature* 1995; 373: 123–126; Fauci A S, *Nature* 1996; 384: 529–33). Despite the high level of viral replication the immune system is sometimes capable of containing HIV-1 infection as is the case in long term non-progressors. (Haynes B F, *Lancet* 1996; 348:933–37; Haynes B F, *Lancet* 1996; 348: 1531–2; Haynes B F, et al. *Science* 1996; 271: 324–8). Salk et al (Salk J, et al. *Science* 1993; 260: 1270–72) have suggested that immune enhancement in HIV-1 infected individuals may further limit disease progression. However, studies to support the effectiveness of vaccines in containing disease progression are inconclusive. Redfield et al (Redfield R R, et al. *N Engi J Med* 1991; 324: 1667–84) have shown in a subgroup of HIV-1 infected individuals receiving a recombinant gp160 vaccine that those who had both a humoral and cellular immune response to the vaccination had also a slower decline in their CD4 cell counts. It was unclear whether this was actually a result of vaccination. Valentine et al (Valentine F T, et al. *J Infect Dis* 1996; 173: 1336–46) and Eron et al (Haynes B F, et al. *Science* 1996; 271: 324–8) have noted that a recombinant gp160, respectively gp12 vaccine induced in HIV+ individuals humoral and cellular immune responses that infection itself did not stimulate. Furthermore, immunized subjects made antibodies to an envelope protein and to p24 both of which were not present in the vaccine suggesting that the vaccine acted both as specific and as a non specific immunostimulant. In both trials vaccinations did not decrease viral plasma load, a main parameter for disease containment.

The main stumbling block in the use of recombinant envelope protein vaccines was considered to be the continuous emergence of variant viruses within an individual over time and the large variability of the $V_3$ loop within one clade of HIV-1 and between different clades. (Kuiken C L, et al. *Proc Natl Acad Sci USA* 1993; 90: 9061–65; Matthews T J, et al. *Proc Natl Acad Sci USA* 1986; 83: 9709–13; Gorny M K, et al. *Proc Natl Acad Sci USA* 1991; 88: 3238–42). There are, however, indications that this variability is not an insurmountable obstacle. The $V_3$ region retains many of its individual characteristics in an infected individual 5 years after infection.. (Kuiken C L, et al. *AIDS* 1996; 10: 31–7). Furthermore, immunization of chimps with recombinant gp160 elicited anti-$V_3$ antibodies with broad crossreactivity to various field isolates despite their variable $V_3$ sequences. (Boudet F, et al. *AIDS Res Human Retrov* 1996; 12: 1671–79). The peptide vaccines described herein were also broadly and highly immunogenic probably due to the aggregate of several unique features.

It has been shown that fractional doses of intradermally injected polio vaccine induced an up to 1024-fold increase in antibody titer. (Samuel B U, et al. *Lancet* 1991; 338; 343–44). The advantage of this route of vaccine administration may be due to the engagement of ample local dendritic cells as antigen presenting cells capable of priming T cells. This may explain why our intradermally applied vaccine elicited high affinity antibodies of both the IgG and IgA class and MHC class-II T cell responses in HIV-1 uninfected vaccinees. (Rubinstein A, et al. *AIDS* 1995; 9: 243–51). It does not, however, fully explain the broad immunogenicity achieved. The latter may be attributed to the use of PPD, a unique carrier in that everyone with a functional immune response who has been exposed to tuberculosis will respond with a DTHR to minute amounts of PPD. This universal T-cell recognition may be due to the fact that PPD is derived from cultures of autolyzed bacteria containing a mixture of degraded and preprocessed antigens that can be presented by the majority of major histocompatibility complex (MHC) class-II haplotypes. This may explain why a PPD conjugated peptide from *Plasmodium falciparum* elicited antibody responses in genetically nonresponder mouse strains to this epitope. (Lussov A R, et al. *Proc Natl Acad Sci USA* 1990; 87: 2960–64). BCG presensitized mice also produced antibodies to peptide and carbohydrate epitopes only if these were conjugated to PPD. (Lussov A R, et al. *Proc Natl Acad Sci USA* 1990; 87: 2960–64; Lachman P J, *Ciba Fund Symp* 1986; 119: 25–57). Furthermore, PPD contains a variety of heatshock proteins that may induce unusual immune responses including Tcell responses. (Mehra V, et al. *J Exp Med* 1992; 175: 275–84; Barnes P F, et al. *J Immunol* 1992; 148: 1835–40).

It has yet to be determined whether PPD is responsible for the induction of MHC class-I (HLA-B7 restricted) responses observed by us in HIV-1 uninfected vaccinees receiving a PPD-MN-PND conjugate vaccine. (Rubinstein A, et al. *AIDS* 1995; 9: 243–51). It has been shown that ovalbumin presented to antigen processing cells together with live tubercle bacilli initially enters the cell vacuole to induce MHC class-II restricted responses but then also translocates to the cytoplasm leading to MHC class-I restricted responses to ovalbumin. (Mazzaccaro R J, et al. *Proc Natl Acad Sci USA* 1996; 93: 11786–11791). Live mycobacteria may secrete a pore forming hemolysin, similar to listeriolysin, (Barry R A, et al. *Infect Immun* 1992; 60: 1625–32) that allows escape of antigens from the vacuole into the cytoplasm as an alternate MHC class-I antigen processing pathway. It is possible that a pore forming factor is present in PPD, a crude extract of the supernatant of mycobacterial cultures.

Using the monopeptide, PPD-MN-PND vaccine in HIV-1 negative subjects, their sera neutralized HIV-1 prototypes but failed to neutralize primary HIV-1 isolates as also reported for other envelope subunit vaccines. (Mascola Jr, et al. *J Infect Dis* 1996; 173: 340–48). Haynes et al (Haynes B F, et al. *J Immunol* 1993; 151: 1646–53) have shown that a mixture of HIV-1 envelope peptides can induce in animals antibodies capable of neutralizing a broad range of HIV-1 isolates. It was observed in guinea pigs immunized with a panel of five $V_3$ loop peptides conjugated to PPD (PPD-pentapeptide-PND) an over 10 fold increase in specific antibody responses to individual PND peptides as compared to immunization with single PND peptide PPD conjugates. Moreover, only the pentapeptide vaccine induced antibodies that also neutralized primary isolates in PBMCs (not shown). Based on these results we have embarked on the present study with a PPD-pentapeptide-PND vaccine in HIV-1 infected volunteers with remarkable immunological and virological improvements.

After 3 monthly immunizations, there was already an increase in antibody responses noted to vaccine peptides noted (FIGS. 12A–12G). In addition, all sera exhibited an augmented response to the V₃ loop apex (GPGR)₃AF (FIGS. 12A–12G). In animals, the GPGRAF sequence was shown to be the target of neutralizing antibodies resulting from peptide immunization. (Boudet F, et al. *AIDS Res Human Retrov* 1996; 12: 1671–79; White-Scharf M E, et al. *Virology* 1993; 192: 197–206; Javaherian K, et al. *Science* 1990; 250: 1590–93). The ability of our vaccine to rapidly induce such antibodies may, therefore, be of clinically relevant.

Figure 13A:
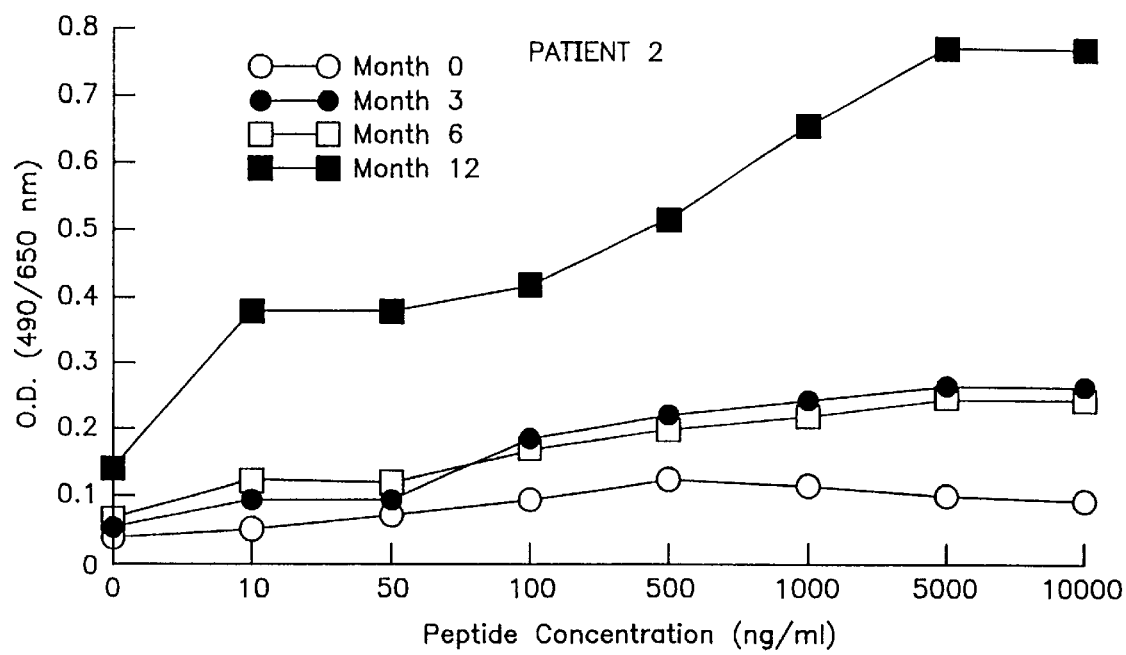
FIGS. 13A and 13B indicate the induced antibody affinity for the MN peptide in patient #2 (FIG. 13A) and patient #5 (FIG. 13B) before and following immunizations with the PPD-pentapeptide-PND vaccine. Microtiter ELISA plate wells were coated with decreasing amounts of the MN peptide, from 10,000 ng/ml to 10 ng/ml. An OD over background at ≦100 ng/ml was considered to indicate high affinity.
Figure 13B:
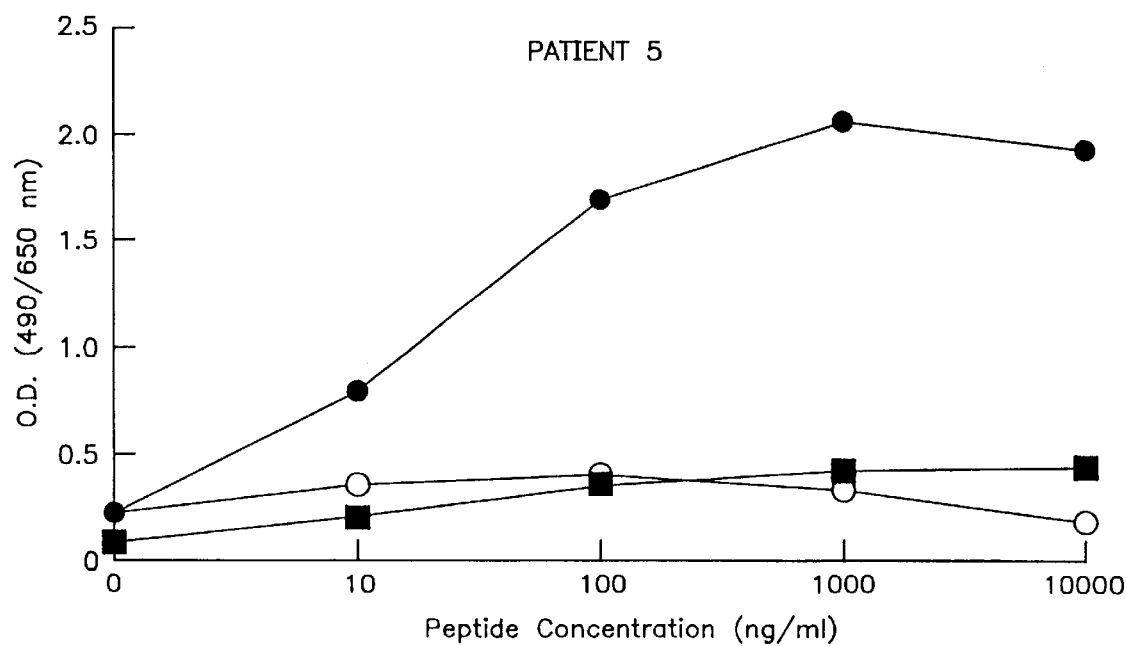
Figure 14A:
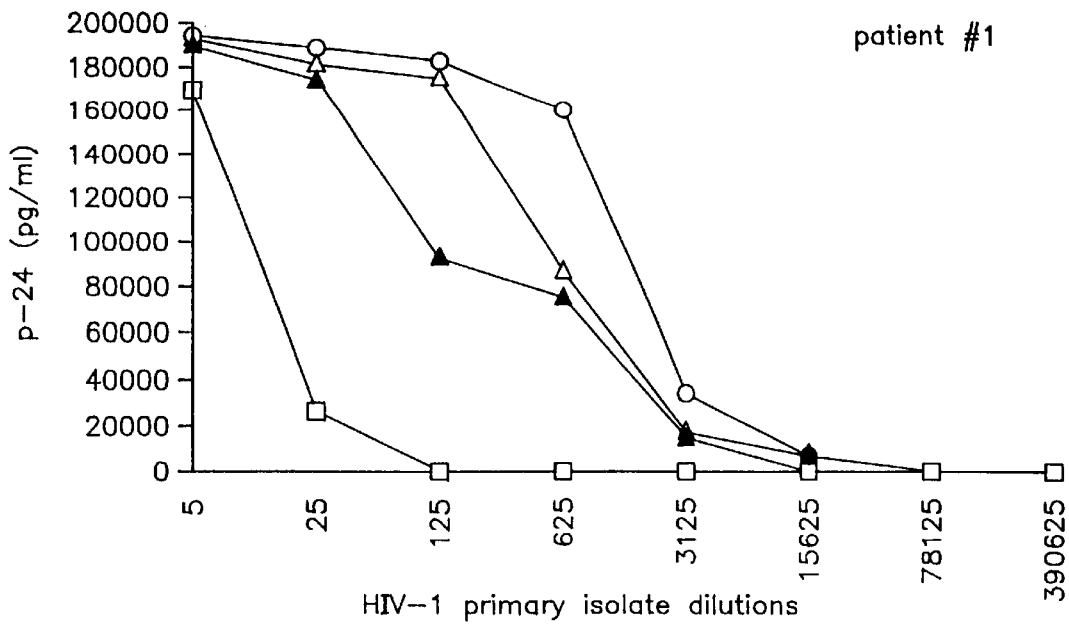
FIGS. 14A–14G indicate neutralization of a Clade B primary isolate (HIV-1-59) by vaccinees' sera, pre and post immunization. The shift of the curves to the left and towards the horizontal axis with time post immunizations indicates a temporal increase in virus neutralization.
Figure 14B:
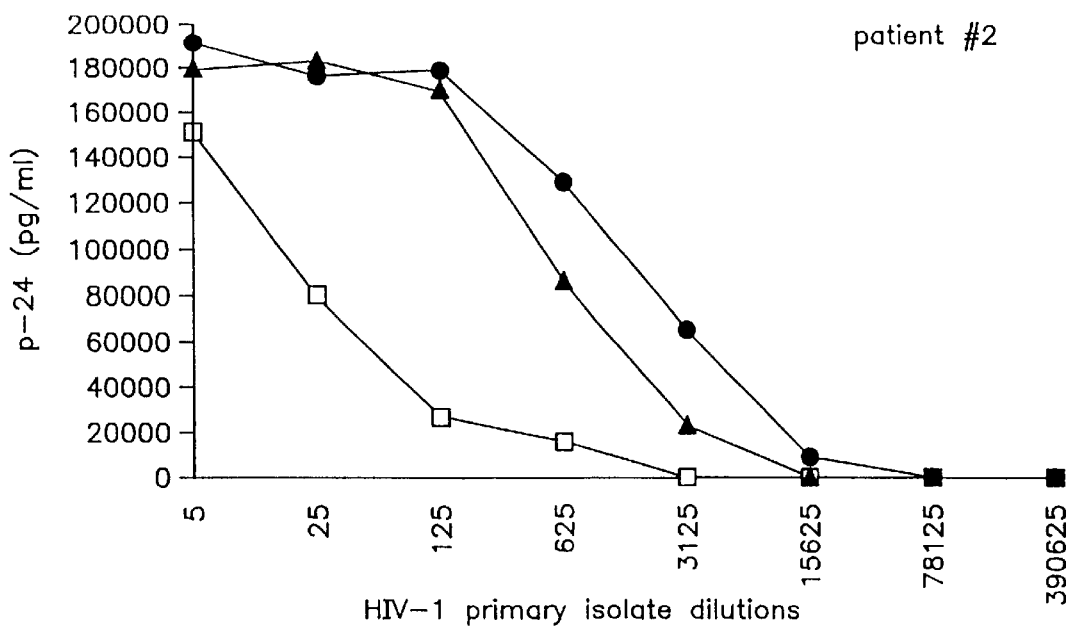
Figure 14C:
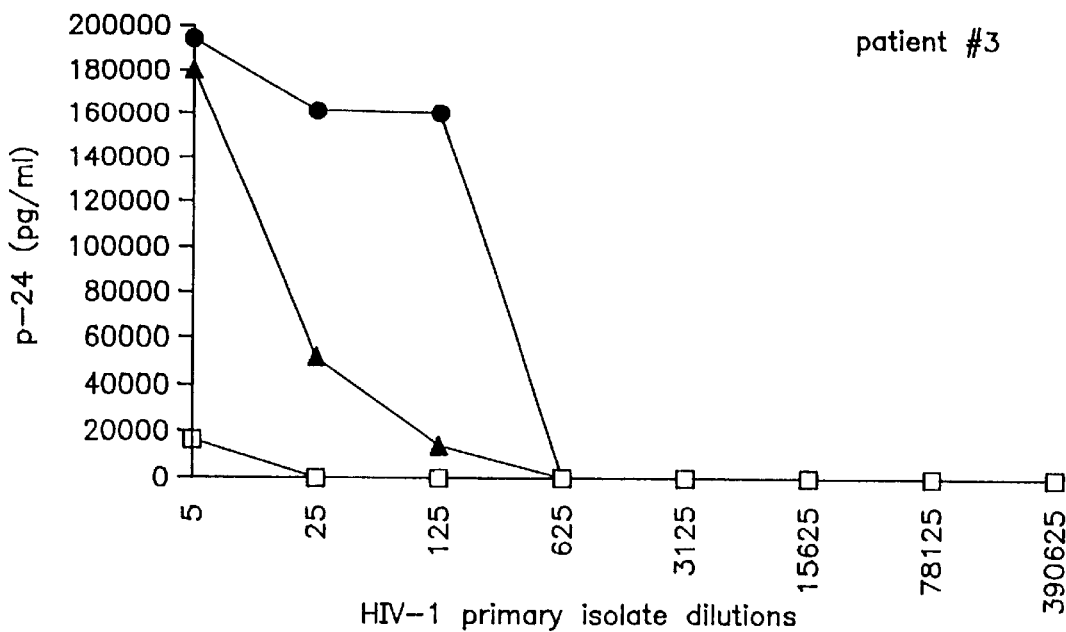
Figure 14D:
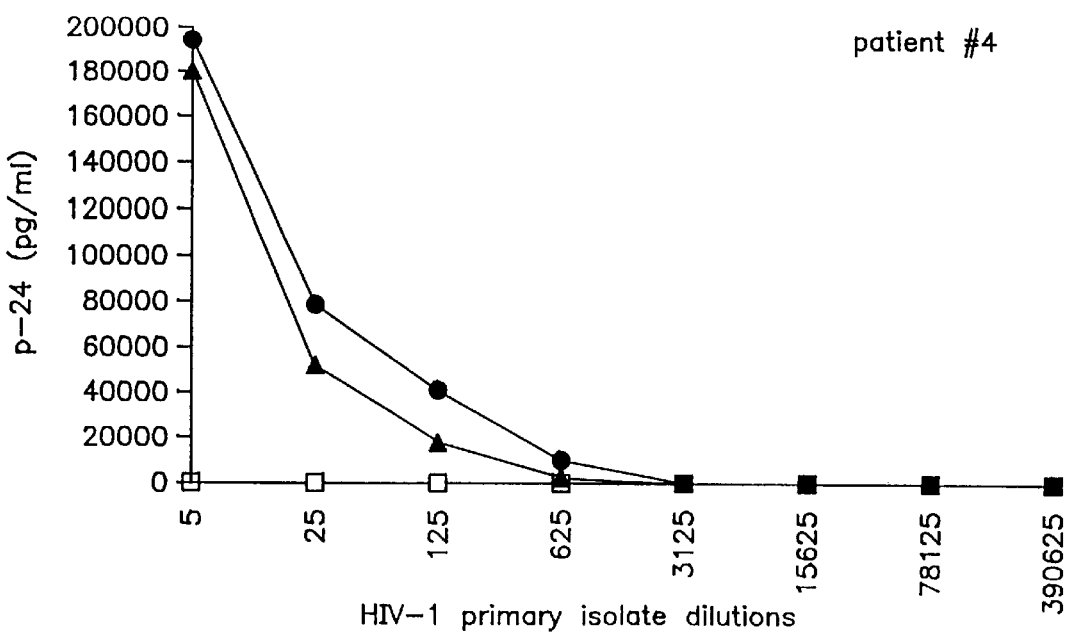
Figure 14E:
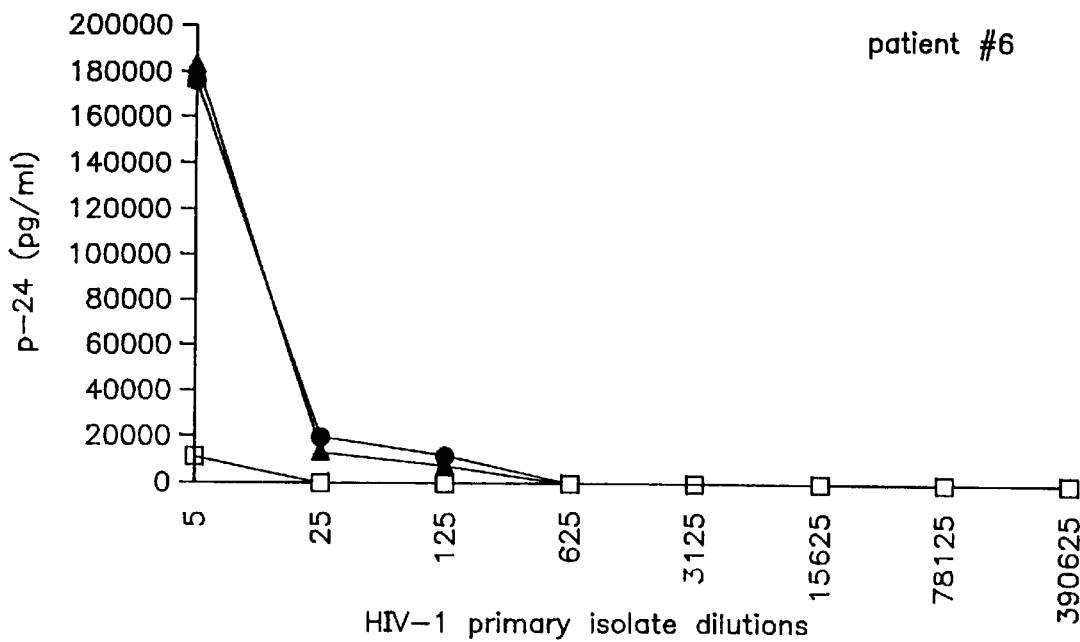
Figure 14F:
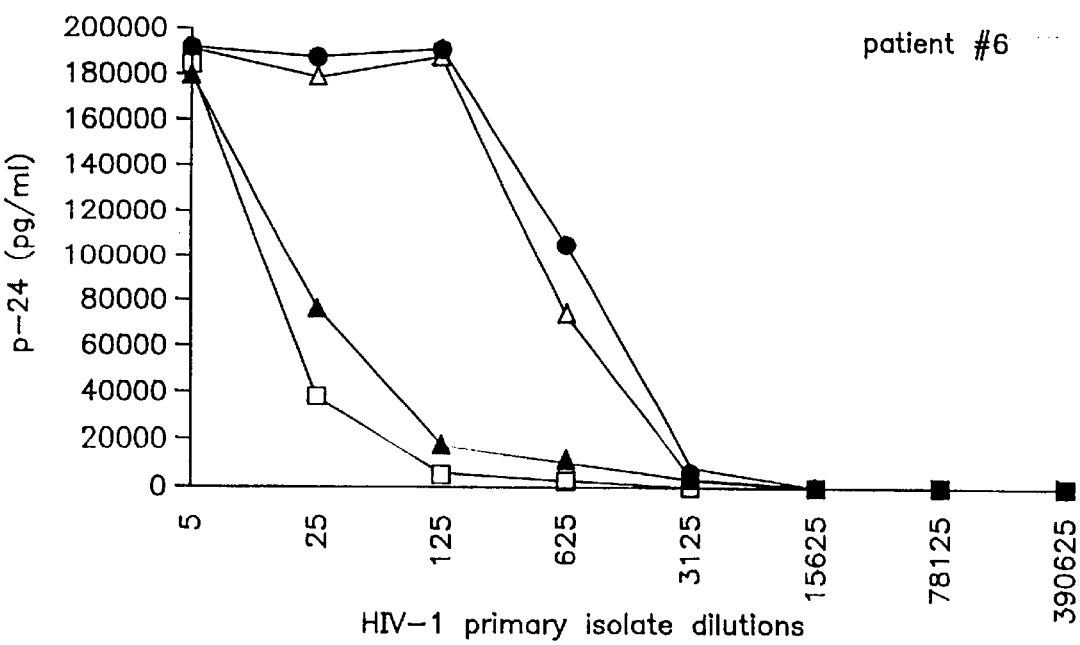
Figure 14G:
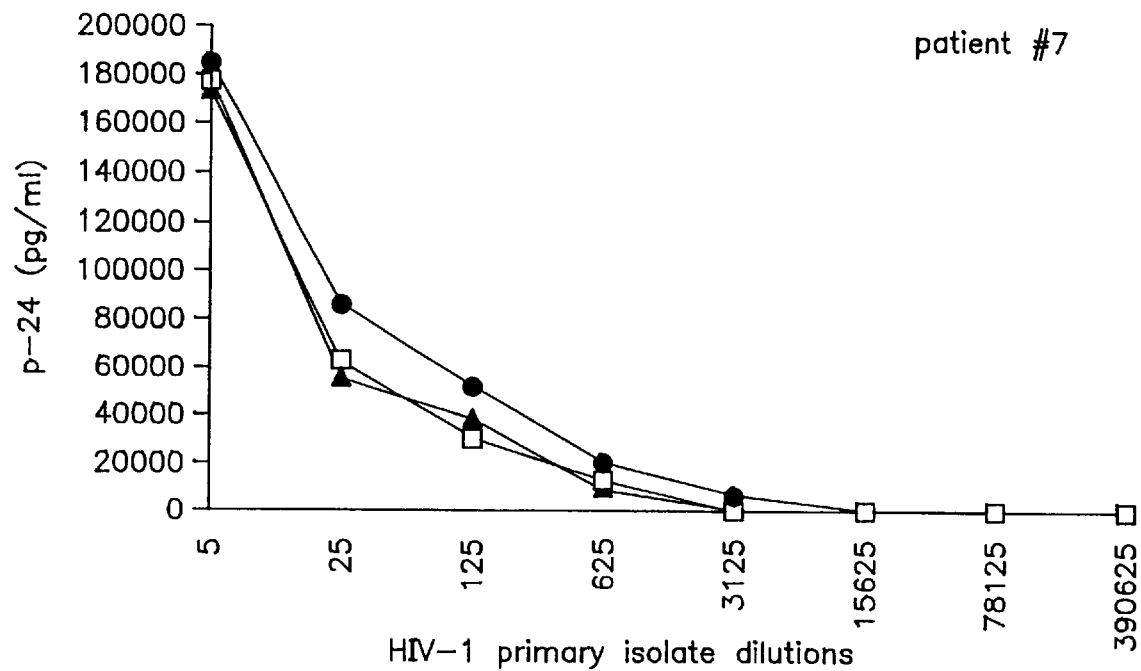

Similar to the results with the monovalent PPD-MN-PND vaccine in HIV-1 negative volunteers, we have also observed with the PPD-pentapeptide-PND immunization of HIV-1 infected individuals a marked increase in antibody affinity after 3 months (FIGS. 13A and 13B). The affinity increased with additional immunizations (FIG. 13A, patient #2). However, in patient #5 who received his last immunization at 6 months, the antibody affinity but not the antibody titer returned to baseline by 12 months. Six months after the loss of high affinity antibodies this patient also exhibited a rise in viral titers. In HIV-1 infection the spontaneously occurring antibody response requires 8–18 months to reach avidity maturation (Thomas H U, et al. *Clin Exp Immunol* 1996; 103: 185–91) which is characteristic of many T-dependent responses. Using the vaccine described herein, this response occurred much earlier, within 3 months (FIGS. 13A and 13B). The level of in vitro neutralization of primary isolates by monoclonal antibodies for the V₃ loop was shown to correlate with the affinity of the antibody (Zolla-Pazner S, et al. *AIDS* 1992; 6: 1235–47) and a correlation has been shown of antibody affinity with HIV-1 maternofetal transmission. (Rubinstein A, et al. *AIDS* 1995; 9: 243–51; Devash Y, et al. *Proc Natl Acad Sci USA* 1991; 87: 345–49). The enhancement of antibody affinity maturation by our vaccine may thus be of clinical significance.

In primary HIV-1 infection, neutralizing antibodies to autologous virus usually develop slowly and peak after the decrease of viremia. (Koup RA, et al. *J Virol* 1994; 68: 4650–5). Promoting the induction of such antibodies in primary infection or at any time during HIV-1 disease may decelerate the virus induced pathology. It is of note that in all the vaccinees there was. an increase in serum neutralization of autologous and of primary isolates starting at 3 months and peaking at 36–172 fold increase at 12 months (Table 37; FIGS. 14A–14G). So far no other vaccine has induced such a potent neutralization of autologous and of primary isolates in the HIV-1 log reduction assay or in the resting cell assay. (Zolla-Pazner S, et al. *AIDS Res Hum Retrov* 1995; 11: 1449–58). The neutralization did, however, appear to be dependent on continuous boosters of the vaccine. In patient #7, for example, the neutralization titer dropped 9 months after the last vaccine boost.

Long term survivors have a lower virus load (Saag M S, Holodniy M, et al. *Nat Med* 1996; 625–29; Mellors J W, et al. *Ann Intern Med* 1995; 122: 573–79; Mellors J W, et al. *Science* 1996; 272: 1167–70; Ho. D D, et al. *Science* 1996; 272: 1124–5) and several studies have shown a dose dependent effect of maternal plasma viremia on the rate of HIV-1 transmission to the baby. (Weiser B, et al. *Proc Natl Acad Sci USA* 1994; 91: 8037–41; Dickover K, et al. *Cell Biochem* 1995; S21B, 233). We have shown a maintenance of an undetectable viral load or a decrease of viral loads in all vaccinees (FIGS. 15A–15G). In two patients with the shortest course of immunization a decrease of viral load to undetectable levels was followed 6 months, respectively, 9 months after the last vaccine boost by an increase in viral load. This renewed viremia was documented to be associated with the loss of antibody affinity (FIGS. 13A and 13B & 15A–15G).

In principal, subunit vaccines have been more effective in inducing antibody responses, while non HIV-1 live vaccine expressing HIV-1 epitopes induced cytotoxic Tcells (CTLs) but did not elicit high titers of neutralizing antibodies. (Abimiku A G, et al. *Nature Medicine* 1995; 1: 321–29; Perales M A, et al. *J. AIDS & Human Retrov* 1995; 10: 27–35. The breadth of the immune responses enhanced by our vaccine including high affinity and neutralizing immunity to autologous and primary isolates and the reduction in plasma viremia suggest that irrespective of the mechanism of action, this vaccine has a favorable influence on parameters associated with improved prognosis.

All publications mentioned hereinabove are hereby incorporated in their entirety.

While the foregoing invention has been described in some detail for purposed of clarity and understanding, it will be appreciated by one skilled in the art from a reading of the disclosure that various changes in form and detail can be made without departing from the true scope of the invention in the appended claims.

What is claimed is:

1. A method for treating a mammal at risk for HIV infection comprising administering to said mammal a peptide composition comprising peptides KRIHIGPGRAFYT (SEQ ID NO:1), RSIHIGPGRAFYA (SEQ ID NO:6), KSITKGPGRVIYA (SEQ ID NO:7), KGIAIGPGRTLYA (SEQ ID NO:8) and SRVTLGPGRVWYT (SEQ ID NO:9), wherein each peptide is coupled to a PPD carrier, and wherein the peptide composition is administered to said mammal in an amount effective to reduce the level of HIV titers in said mammal upon subsequent HIV infection.

2. The method of claim 1, wherein the composition is administered intradermally.

3. The method of claim 1, wherein a PPD carrier is conjugated to each peptide via glutalderhyde.

* * * * *